US012613236B2

(12) United States Patent
Tata et al.

(10) Patent No.: US 12,613,236 B2
(45) Date of Patent: Apr. 28, 2026

(54) LUNG FIBROSIS MODEL AND METHODS OF USING THE SAME

(71) Applicant: DUKE UNIVERSITY, Durham, NC (US)

(72) Inventors: Purushothama Rao Tata, Durham, NC (US); Aleksandra Tata, Durham, NC (US); Arvind Konkimalla, Durham, NC (US); Yoshihiko Kobayashi, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 834 days.

(21) Appl. No.: 17/763,991

(22) PCT Filed: Sep. 28, 2020

(86) PCT No.: PCT/US2020/053164
§ 371 (c)(1),
(2) Date: Mar. 25, 2022

(87) PCT Pub. No.: WO2021/062412
PCT Pub. Date: Apr. 1, 2021

(65) Prior Publication Data
US 2022/0341915 A1      Oct. 27, 2022

Related U.S. Application Data

(60) Provisional application No. 62/975,294, filed on Feb. 12, 2020, provisional application No. 62/906,241, filed on Sep. 26, 2019.

(51) Int. Cl.
*G01N 33/50* (2006.01)
*C12N 5/071* (2010.01)

(52) U.S. Cl.
CPC ....... *G01N 33/5023* (2013.01); *C12N 5/0688* (2013.01); *G01N 33/5088* (2013.01); *C12N 2501/135* (2013.01); *C12N 2502/27* (2013.01)

(58) Field of Classification Search
None
See application file for complete search history.

(56) References Cited

U.S. PATENT DOCUMENTS

2018/0066231 A1     3/2018   Ikeyama et al.

FOREIGN PATENT DOCUMENTS

WO          2016143803 A1      9/2016
WO          2019005528 A1      1/2019

OTHER PUBLICATIONS

Barkauskas et al, "Type 2 alveolar cells are stem cells in adult lung" J Clin Invest (Year: 2013).*

Barkauskas et al. "lung organoids: current uses and future promises" Development (Year: 2017).*
Shimuzu et al., "thrombin stimulates the expression of PDGF in lung epithelial cells" Am J Physiol Lung Cell Mol Physiol (Year: 2000).*
Cunningham et al., "Identification of benzodiazepine Ro 5-3335 as an inhibitor of CBF leukemia through quantiative high throughput screen against RUNX1-CBFbeta" Proc Natl Acad Sci USA (Year: 2012).*
U.S. Appl. No. 62/975,294, inventors Tata; Purushothama Rao et al., filed Feb. 12, 2020.
Vu B.T., et al., "Optimization of Culture Medium for the Isolation and Propagation of Human Breast Cancer Cells From Primary Tumour Biopsies," Biomedical Research and Therapy, Feb. 22, 2015, vol. 2, No. 2, pp. 207-219.
Zacharias W. J., et al., "Regeneration of the Lung Alveolus by an Evolutionarily Conserved Epithelial Progenitor," Nature, 2018, vol. 555, No. 7695, pp. 251-255.
Zepp J. A., et al., "Distinct Mesenchymal Lineages and Niches Promote Epithelial Self-Renewal and Myofibrogenesis in the Lung," Cell, 2017, vol. 170, No. 6, pp. 1134-1148.
Zhang M., et al., "Chop Deficiency Prevents UUO-Induced Renal Fibrosis by Attenuating Fibrotic Signals Originated from Hmgb1/ TLR4/NF?B/IL-1ß Signaling," Cell Death & Disease, Nature, 2015, vol. 6, No. 8:e1847, 11 pages.
Ziegler C. G. K., et al., "SARS-CoV-2 Receptor ACE2 Is an Interferon-Stimulated Gene in Human Airway Epithelial Cells and Is Detected in Specific Cell Subsets across Tissues," Cell, 2020, vol. 181, No. 5, pp. 1016-1035.
International Search Report and Written Opinion mailed Feb. 8, 2021 for PCT/US2020/053164 filed Sep. 28, 2020 (Applicant— Duke University // Inventor—Purushothama Rao Tata) (11 pages).
Adams T.S., et al., "Single Cell RNA-Seq Reveals Ectopic and Aberrant Lung Resident Cell Populations in Idiopathic Pulmonary Fibrosis," bioRxiv 759902, 2019, 17 pages.
Barkauskas C.E., et al., "Lung Organoids: Current uses and Future Promise," The Company of Biologists, Development, Mar. 2017, vol. 144, No. 6, pp. 986-997.
Barkauskas C.E., et al., "Type 2 Alveolar Cells are Stem Cells in Adult Lung," Journal of Clinical Investigation, Jul. 2013, vol. 123, No. 7, pp. 3025-3036.
Barrat F. J., et al., "Interferon Target-Gene Expression and Epigenomic Signatures in Health and Disease," Nature Immunology, 2019, vol. 20, No. 12, pp. 1574-1583.
Bartee E., et al., "Tumor Necrosis Factor and Interferon: Cytokines in Harmony," Current Opinion in Microbiology, 2008, vol. 11, No. 4, pp. 378-383.

(Continued)

*Primary Examiner* — Tracy Vivlemore
*Assistant Examiner* — John David Moore
(74) *Attorney, Agent, or Firm* — Polsinelli PC

(57) ABSTRACT

The present disclosure provides a newly-identified transitional cell state in alveolar regeneration, models to ablate lung alveolar type-1 cells that leads to lung fibrosis and emphysema, a scalable, an ex vivo lung fibrosis model that uses co-cultured lung fibroblasts and pre-alveolar type-1 transitional cell state (PATS) for the use of disease modeling and drug screening, and methods of using same.

15 Claims, 45 Drawing Sheets

(56)                  References Cited

OTHER PUBLICATIONS

Beers M. F., et al., "When Is an Alveolar Type 2 Cell an Alveolar Type 2 Cell? A Conundrum for Lung Stem Cell Biology and Regenerative Medicine," American Journal of Respiratory Cell and Molecular Biology, 2017, vol. 57, No. 1, pp. 18-27.

Blanpain C., et al., "Stem Cell Plasticity. Plasticity of Epithelial Stem Cells in Tissue Regeneration," Science, 2014, vol. 344, No. 6189:1242281, 23 pages.

Bolger M. E., et al., "Plant Genome Sequencing—Applications for Crop Improvement," Current Opinion in Biotechnology, 2014, vol. 26, pp. 31-37.

Bost P., et al., "Host-Viral Infection Maps Reveal Signatures of Severe COVID-19 Patients," Cell, 2020, vol. 181, No. 7, pp. 1475-1488, e12.

Cheng D. S., et al., "Airway Epithelium Controls Lung Inflammation and Injury through the NF-Kappa B Pathway," Journal of Immunology, 2007, vol. 178, No. 10, pp. 6504-6513.

Chung K. P., et al., "Mitofusins Regulate Lipid Metabolism to Mediate the Development of Lung Fibrosis," Nature Communications, 2019, vol. 10, No. 1:3390, 17 pages.

Chung M. I., et al., "Niche-Mediated BMP/SMAD Signaling Regulates Lung Alveolar Stem Cell Proliferation and Differentiation," Development, 2018, vol. 145, No. 9:dev163014, 10 pages.

Da Silva A. L., et al., "Evaluation of DNA Damage in COPD Patients and its Correlation with Polymorphisms in Repair Genes," BMC Medical Genetics, 2013, vol. 14, No. 93, 8 pages.

Didonato J. A., et al., "NF-κB and the Link between Inflammation and Cancer," Immunological Reviews, 2012, vol. 246, No. 1, pp. 379-400.

Frank D. B., et al., "Emergence of a Wave of Wnt Signaling that Regulates Lung Alveologenesis by Controlling Epithelial Self-Renewal and Differentiation," Cell Reports, 2016, vol. 17, No. 9, pp. 2312-2325.

Habermann A. C., et al., "Single-Cell RNA Sequencing Reveals Profibrotic Roles of Distinct Epithelial and Mesenchymal Lineages in Pulmonary Fibrosis," Science Advances, 2020, vol. 6, No. 28:eaba1972, 16 pages.

Hafemeister C., et al., "Normalization and Variance Stabilization of Single-Cell RNA-seq Data Using Regularized Negative Binomial Regression," Genome Biology, 2019, vol. 20, No. 1:296, 15 pages.

Hou Y. J., et al., "SARS-CoV-2 Reverse Genetics Reveals a Variable Infection Gradient in the Respiratory Tract," Cell, 2020, vol. 182, No. 2, pp. 429-446.e14.

Huang C., et al., "Clinical Features of Patients Infected with 2019 Novel Coronavirus in Wuhan, China," The Lancet, 2020, vol. 395, No. 10223, pp. 497-506.

International Search Report and Written Opinion mailed Feb. 25, 2021 for corresponding International Patent Application No. PCT/US2020/053158, 13 pages.

Karin M., "NF-KappaB as a Critical Link between Inflammation and Cancer," Cold Spring Harbor Perspectives in Biology, 2009, vol. 1, No. 5:a000141, 15 pages.

Katsura H., et al., "IL-1 and TNF alpha Contribute to the Inflammatory Niche to Enhance Alveolar Regeneration," Stem Cell Reports, Apr. 9, 2019, vol. 12, No. 4, pp. 657-666.

Kim D., et al., "Graph-Based Genome Alignment and Genotyping with HISAT2 and HISAT-Genotype," Nature Biotechnology, 2019, vol. 37, No. 8, pp. 907-915.

Koerner I., et al., "Protective Role of Beta Interferon in Host Defense against Influenza A Virus," Journal of Virology, 2007, vol. 81, No. 4, pp. 2025-2030.

Kropski J. A., et al., "Genetic Studies Provide Clues on the Pathogenesis of Idiopathic Pulmonary Fibrosis," Disease Models & Mechanisms, 2013, vol. 6, No. 1, pp. 9-17.

Kuleshov M. V., et al., "Enrichr: A Comprehensive Gene Set Enrichment Analysis Web Server 2016 Update," Nucleic Acids Research, 2016, vol. 44(W1), pp. W90-W97.

Lacanna R., et al., "Yap/Taz Regulate Alveolar Regeneration and Resolution of Lung Inflammation," Journal of Clinical Investigation, 2019, vol. 129, No. 5, pp. 2107-2122.

Lee J. H., et al., "Lung Stem Cell Differentiation in Mice Directed by Endothelial Cells via a BMP4-NFATc1-Thrombospondin-1 Axis," Cell, 2014, vol. 156, No. 3, pp. 440-455.

Lee J. H., et al., "Surfactant Protein-C Chromatin-Bound Green Fluorescence Protein Reporter Mice Reveal Heterogeneity of Surfactant Protein C-Expressing Lung Cells," American Journal of Respiratory Cell and Molecular Biology, 2013, vol. 48, No. 3, pp. 288-298.

Li H., et al., "The Sequence Alignment/Map format and SAMtools," Bioinformatics, 2009, vol. 25, No. 16, pp. 2078-2079.

Liao M., et al., "Single-Cell Landscape of Bronchoalveolar Immune Cells in Patients with COVID-19," Nature Medicine, 2020, vol. 26, No. 6, pp. 842-844.

Liao Y., et al., "Featurecounts: an Efficient General Purpose Program for Assigning Sequence Reads to Genomic Features," Subread manual 1.5. 0-p1, Bioinformatics, 2014, vol. 30, pp. 923-930.

Lipson K. E., et al., "CTGF is a Central Mediator of Tissue Remodeling and Fibrosis and its Inhibition can Reverse the Process of Fibrosis," Fibrogenesis Tissue Repair, 2012, vol. 5(Suppl 1):S24, 8 pages.

Love M I., et al., "Moderated Estimation of Fold Change and Dispersion for RNA-seq Data with DESeq2," Senome Biology, 2014, vol. 15:550, 21 pages.

Martin M., "Cutadapt Removes Adapter Sequences from High-Throughput Sequencing Reads," EMBnet.journal, 2011, vol. 17, No. 1, pp. 10-12.

Mason R. J., et al., "Phospholipid Composition and Ultrastructure of A549 Cells and Other Cultured Pulmonary Epithelial Cells of Presumed Type II Cell Origin," Biochimica et Biophysica Acta, 1980, vol. 617, No. 1, pp. 36-50.

Mccauley K.B., et al., "Single-Cell Transcriptomic Profiling of Pluripotent Stem Cell-Derived SCGB3A2+ Airway Epithelium," Stem Cell Reports, May 8, 2018, vol. 10, No. 5, pp. 1579-1595.

Mcconnell A. M., et al., "p53 Regulates Progenitor Cell Quiescence and Differentiation in the Airway," Cell Reports, 2016, vol. 17, No. 9, pp. 2173-2182.

Mcgregor A. L., et al., "Squish and Squeeze—The Nucleus as a Physical Barrier during Migration in Confined Environments," Current Opinion in Cell Biology, 2016, vol. 40, pp. 32-40.

Menachery V.D., et al., "Pathogenic Influenza Viruses and Coronaviruses Utilize Similar and Contrasting Approaches to Control Interferon-Stimulated Gene Responses," mBio, 2014, vol. 5, No. 3:e01174-14, 11 pages.

Osada N., et al., "The Genome Landscape of the African Green Monkey Kidney-Derived Vero Cell Line," DNA Research, 2014, vol. 21, No. 6, pp. 673-683.

Riemondy K. A., et al., "Single-Cell RNA Sequencing Identifies TGF-ß as a Key Regenerative cue Following LPS-Induced Lung Injury," The Journal of Clinical Investigation, 2019, vol. 4, No. 8, 18 pages.

Sauler M., et al., "Cell Death in the Lung: The Apoptosis-Necroptosis Axis," Annual Review of Physiology, 2019, vol. 81, pp. 375-402.

Sauler M., et al., "The DNA Repair Transcriptome in Severe COPD," European Respiratory Journal, 2018, vol. 52, No. 4:1701994, 12 pages.

Schwartz D. A., "Idiopathic Pulmonary Fibrosis Is a Genetic Disease Involving Mucus and the Peripheral Airways," Annals of the American Thoracic Society, 2018, vol. 15(Suppl 3), pp. S192-S197.

Shimizu S., et al., "Thrombin Stimulates the Expression of PDGF in Lung Epithelial Cells," American Journal of Physiology Lung Cellular and Molecular Physiology, Sep. 2000, vol. 279, No. 3, pp. L503-L510.

Stuart T., et al., "Integrative Single-Cell Analysis," Nature Reviews Genetics, 2019, vol. 20, No. 5, pp. 257-272.

Syedbasha M., et al., "Interferon Lambda: Modulating Immunity in Infectious Diseases," Frontiers in Immunology, 2017, vol. 8, No. 119, 13 pages.

(56)          References Cited

OTHER PUBLICATIONS

Takashima S., et al., "T Cell-Derived Interferon-γ Programs Stem Cell Death in Immune-Mediated Intestinal Damage," 2019, Science Immunology, vol. 4, No. 42:eaay8556, 28 pages.

U.S. Appl. No. 62/906,241, inventors Tata; Purushothama Rao et al., filed Sep. 26, 2019.

Sucre, J.M.S. et al "Successful Establishment of Primary Type II Alveolar Epithelium with 3D Organotypic Coculture" Am. Jour. Respir. Cell Mol. Biol., American Thoraci Society, 2018, 59 (2), pp. 158-166.

Kobayashi, Y. et al. "Persistence of a regeneration-associated, transitional alveolar epithelial cell state in pulmonary fibrosis", bioRxiv, Cold Spring Harbor Laboratory, Nov. 25, 2019 <<https://www.biorxiv.org/content/10.1101/855155v1.full>>.

Barkauskas, C.E. et al. "Type 2 alveolar cells are stem cells in adult lung" J. Clin. Invest, 2013, 123 (7) pp. 3025-3036.

Kobayashi Y. et al. (Nov. 25, 2019) BioRxiv pre-print available at https://www.biorvix.org/content/10.1101/055155v1.full.pdf.

Choi J. et al. (2020) Cell Stem Cell, 27(3):366-382.

* cited by examiner

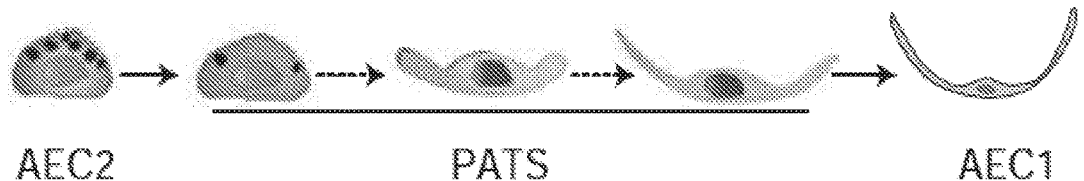
AEC2                        PATS                        AEC1
FIG. 5F
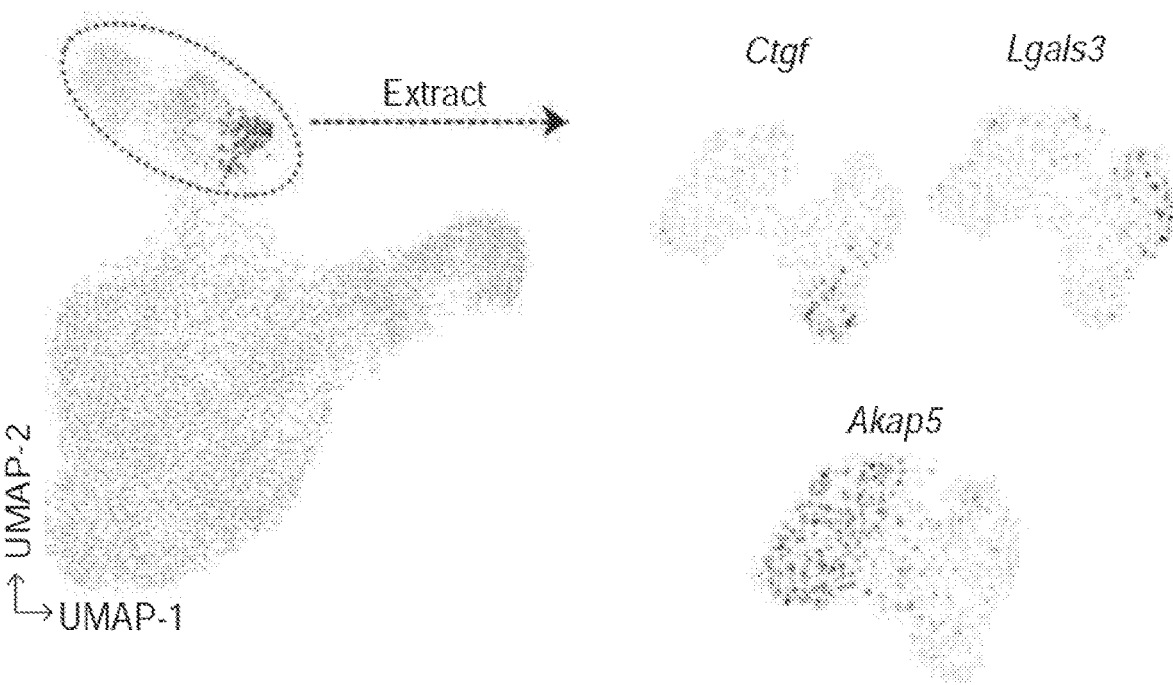
FIG. 6A                                    FIG. 6B

Control

Bleomycin day 12

Control    Bleomycin Day 10

CDKN1A *Sftpc*-tdt AGER DAPI

Control    DT day 6

CDKN1A LGALS3 AGER DAPI

*Sftpc*-GFP     γH2AX     AGER     Overlay + DAPI

Day 2

Day 5

Tmx    PBS or bleomycin    DMSO or Nutlin-3a    Tissue collection and analysis

~2 weeks    Day 0    Day 8    Day 18    Day 20

*Sftpc-CreER; R26R-tdTomato*

AEC1 genes (no enrichment of TP53)

AEC2 genes (no enrichment of TP53)

*Ager-CreER;R26R-DTR*

LUNG FIBROSIS MODEL AND METHODS OF USING THE SAME

CROSS REFERENCE TO RELATED APPLICATIONS

This application is a national phase application of International Application No. PCT/US2020/053164 filed Sep. 28, 2020, which claims priority to U.S. Provisional Patent Application Ser. No. 62/975,294, filed Feb. 12, 2020 and U.S. Provisional Patent Application Ser. No. 62/906,241, filed Sep. 26, 2019, the contents of each of which are hereby incorporated by reference in their entirety.

STATEMENT REGARDING FEDERALLY SPONSORED RESEARCH OR DEVELOPMENT

This invention was made with government support under HL127181 and HL153375. The government has certain rights in this invention.

BACKGROUND

Field

The present disclosure provides the identification of a transitional cell state in alveolar regeneration, a model to ablate lung alveolar type-1 cells that leads to lung fibrosis and emphysema, a scalable, ex vivo lung fibrosis model that uses co-cultured lung fibroblasts and pre-alveolar type-1 transitional cell state (PATS) cells for the use of disease modeling, drug discovery, and/or drug screening, and methods of using same.

Description of the Related Art

Adult stem cells undergo dynamic changes in response to tissue damage. These changes include resurgence from a quiescent or poised state, onset of proliferation, activation of new gene expression and a return to homeostasis. In many cases, repair also involves changes in epithelial cell shape, for example, through transient stretching and expansion to cover areas of damage or denudation. Studies of stem cell regeneration usually focus on understanding how cells select new differentiation programs in response to signals from the niche. However, much less is known about the significance of changes in parameters such as cell shape and spreading and whether they involve the transient and tightly controlled expression of genes usually associated with pathological states including DNA repair and senescence.

In the lung, the maintenance of the alveolar epithelium at homeostasis and its regeneration after injury are fueled by cuboidal surfactant-producing type-2 alveolar epithelial cells (AEC2s), which can self-renew and differentiate into very large thin type-1 alveolar epithelial cells (AEC1s), specialized for gas exchange. Recent studies have identified a subset of AEC2s that are enriched for active Wnt signaling and have higher 'sternness' compared with Wnt-inactive AEC2s. Such differences in alveolar progenitor cell subsets have been attributed to differences in microenvironmental signals; in this case, to the vicinity of PDGFRα-expressing fibroblasts, which produce ligands to activate Wnt signaling in AEC2s. Recent studies have also implicated other signaling pathways—including BMP, Notch, TGFβ, YAP and NF-κB—in the proliferation and differentiation of AEC2s, both at steady state and in response to alveolar injury. However, the precise mechanisms by which the cuboidal AEC2s orchestrate their dramatic changes in cell shape, structure and mechanical properties as they convert into thin flat AEC1s, remain elusive. In addition, the cellular mechanisms that drive AEC2s to express genes associated with cell senescence, a feature commonly observed in most progressive pulmonary diseases, remain unknown.

Here, using organoid cultures and single-cell transcriptome studies, previously unknown, distinct cell states encompassing the transition between AEC2s and AEC1s were uncovered. Moreover, murine lineage tracing, coupled with injury-repair models, has revealed the existence of similar transition states in vivo. The study reveals signaling pathways that control these transition states. As described herein, these transitional states exhibit DNA-damage responses and express senescence-related genes en route to AEC1. Mechanistically, the use of genetic loss of function, pharmacological gain of function and genomic binding assays revealed a direct transcriptional control of PATS by TP53 signaling. Importantly, these transitional states correlate with abnormal epithelial cells associated with defective fibrotic foci in human lungs with progressive pulmonary fibrosis.

BRIEF SUMMARY OF THE DISCLOSURE

The present disclosure is based, in part, on the discovery by the inventors that a transitional cell state exists in alveolar regeneration, which lends itself to models for the use for understanding lung disease, drug discovery, and/or drug screening.

One aspect of the present disclosure provides a method of generating a lung injury organoid model, the method comprising: i) providing a co-culture of cells in a culture medium adapted for the culture of said cells, wherein the co-culture comprises pre-alveolar type-1 transitional cell state (PATS) cells and alveolar fibroblasts; ii) contacting the culture medium with one or more agents; and iii) analyzing the biological effect of the agent on at least one expression marker of the PATS cells and/or the alveolar fibroblasts relative to a control cell culture medium that has not been contacted by the agent.

In some embodiments of the disclosure, the PATS cells are isolated from diseased tissue. In some embodiments of the disclosure, the diseased tissue is chronic obstructive pulmonary disease (COPD) lung tissue, pulmonary fibrosis lung tissue, idiopathic pulmonary fibrosis lung tissue, emphysema lung tissue, lung cancer tissue, Sarcoidosis lung tissue, interstitial pneumonia lung tissue, sepsis lung tissue, lung tissue having viral and bacterial infections, acute respiratory distress syndrome lung tissue, or bronchopulmonary dysplasia lung tissue.

In some embodiments of the disclosure, the PATS cells are generated by exposing lung epithelial cells to an injury-causing agent (e.g., bleomycin, diphtheria toxin (DT), tamoxifen, irradiation, a virus, a bacterium, or a fungus) in vivo or in vitro.

In some embodiments of the disclosure, the alveolar fibroblasts are lipofibroblasts.

In other embodiments of the disclosure, the alveolar fibroblasts have disease-state characteristics. In some embodiments of the disclosure, the disease-state characteristic comprises lipofibroblast cells that express ACTA2, the presence of myofibroblast cells, and/or cell changes from a sellate shape to a banded shape.

In some embodiments of the disclosure, the culture medium comprises a platelet-derived growth factor receptor (PDGFR) ligand.

In some embodiments, the culture medium comprises an agent that is capable of maintaining or modulating PDGFR expression.

Another aspect of the disclosure provides a method of generating an ex vivo model for lung fibrosis, the method comprising: i) providing a culture of AEC1 cells that have undergone ablation in vivo in a culture medium adapted for the culture of said cells; ii) contacting the culture medium with one or more agents; and iii) analyzing the biological effect of the agent on at least one expression marker of the AEC1 cells relative to a control cell culture medium that has not been contacted by the agent.

In some embodiments, the AEC1 cells have undergone at least one round of ablation. In other embodiments, the AEC1 cells have undergone ablation alone or in combination with other injury models. In some embodiments, the AEC1 cells have undergone repeated ablation, for example, over the course of about three days to about two weeks.

In some embodiments of the disclosure, the AEC1 cells have undergone ablation by being exposed to bleomycin, diphtheria toxin (DT), asbestos, chemical toxic agents, tamoxifen, a virus, a bacterium, or a fungus.

In some embodiments, the AEC1 cells express aSMA and/or ACTA2. In some embodiments, the AEC1 cells exhibit characteristics of a fibromyocyte cell.

Yet another aspect of the disclosure provides a method of identifying pre-alveolar type-1 transitional cell state (PATS) cells or PATS-like cells, the method comprising: i) obtaining alveolar cells; and ii) screening the cells for one or more markers, wherein the presence of the one or more markers indicates the presence of PATS cells or PATS-like cells.

In some embodiments of the disclosure, the alveolar cells are selected from the group consisting of tracheal basal cells, bronchiolar secretory cells (also known as club cells or Clara cells), club variant cells, alveolar epithelial progenitor (AEP) cells, clara variant cells, distal lung progenitors, p63+ Krt5– airway cells, lineage negative epithelial progenitors, bronchioalveolar stem cells (BASCs), Sox9+ p63+ cells, neuroendocrine progenitor cells, distal airway stem cells, submucosal gland duct cell, induced pluripotent stem cell-derived lung stem cells and alveolar type 2 epithelial (AEC2) cells.

In some embodiments of the disclosure, the alveolar cells are obtained from the lung of a patient suffering from chronic obstructive pulmonary disease (COPD), pulmonary fibrosis, idiopathic pulmonary fibrosis, emphysema, lung cancer, Sarcoidosis, interstitial pneumonia, sepsis, a viral infection, a bacterial infection, a fungal infection, acute respiratory distress syndrome, and/or bronchopulmonary dysplasia.

In some embodiments of the disclosure of identifying pre-alveolar type-1 transitional cell state (PATS) cells or PATS-like cells further comprises contacting the alveolar cells with an agent (e.g., bleomycin, diphtheria toxin (DT), tamoxifen, a virus, a bacterium, or a fungus).

Yet another aspect of the present disclosure provides a method of generating an in vivo tissue fibrosis model, the method comprising: i) introducing a genetic loss of PDGF ligands and/or PDGF receptor (PDGFR) signaling in a subject; and/or ii) administering an agent to a subject that can modulate PDGF-PDGFR signaling; and iii) analyzing cells from the subject to determine the biological effect of genetic loss of PDGF ligands and/or PDGF receptor (PDGFR) signaling and/or the biological effect of the agent that can modulate PDGF-PDGFR signaling relative to a control subject.

In some embodiments, the agent that can modulate PDGF-PDGFR signaling comprises a PDGFR inhibitor, a PDGFR agonist, a PDGF inhibitor, or a PDGF agonist.

Yet another aspect of the disclosure provides a method of generating an in vivo tissue fibrosis model, the method comprising: i) introducing a genetic loss of RUNX1, RUNX2, RUNX3, or CBFb in a subject; and/or ii) administering to the subject a RUNX1, RUNX2, RUNX3, or CBFb inhibitor; and iii) analyzing cells from the subject to determine the biological effect of the genetic loss of RUNX1, RUNX2, RUNX3, or CBFP and/or the biological effect of the RUNX1, RUNX2, RUNX3, or CBFP inhibitor relative to a control subject.

In some embodiments, the inhibitor is Ro 5-3335, AI-10-49, or a neutralizing antibody against RUNX1, RUNX2, RUNX3, and/or CBFP.

In some embodiments, the in vivo model is a mouse model.

In some embodiments, the in vivo model is a disease model for fibrosis in the lung, liver, kidney, skin, intestines, or bone marrow.

BRIEF DESCRIPTION OF THE DRAWINGS

FIG. 1A is a schematic of the alveolar organoid culture utilized for scRNA-seq. FIG. 1B show a Pearson correlation plot visualizes the number of genes per cell (nGene) and unique molecular identifier (nUMI) in total cells derived from alveolar organoids (left panel, 10,948 cells). UMAP shows major cell populations including epithelial cells (5,163 cells), fibroblasts (5,686 cells), and some minor populations such as endothelial cells (66 cells) and macrophages (33 cells) in alveolar organoids (right panel). FIG. 1C is an integrated UMAP showing cells derived from alveolar organoids (4,787 cells), in vivo homeostatic mouse lung (1,878 cells) and LPS-treated mouse lung (14,323 cells) (left). Expression of indicated genes in the integrated UMAP (right). FIG. 1D is a UMAP visualization of the epithelial populations in cultured alveolar organoids (n=4,573 cells): AEC2s (n=3,303 cells); AEC2-proliferating, proliferating AEC2s (n=696 cells); AEC1s (n=262 cells) and new cell states—Lgals3+(n=184 cells) and Ctgf+ cells (n=128 cells). FIG. 1E are UMAP plots showing the expression of the indicated genes in epithelial populations in cultured alveolar organoids. FIG. 1F are UMAP plots showing the expression of indicated genes in AEC2, AEC2-proliferating, AEC1, and novel alveolar epithelial cell state in alveolar organoid scRNA-seq dataset (4,573 cells) and LPS treated or control lungs (13,204 cells). FIG. 1G is a volcano plot showing specific genes enriched in the Ctgf+(n=128 cells) and Lgals3+(n=184 cells) transitional cell states. A Wilcoxon rank-sum test was used for the statistical analysis. Data points indicate transcripts that fall below the set threshold for fold change (Log 2) and P value (Log 10). FIG. 1H is a schematic of alveolar organoid culture using fibroblasts and AEC2s. Tmx, tamoxifen.

FIG. 4A is a schematic showing the experimental design to ablate AEC1s in the Ager-CreER; R26R-DTR mouse model. The mice were administered tamoxifen, followed by DT, and tissues were collected on day 6. FIG. 4B is a graph showing proportion of elongated LGALS3+ cells in control and AEC1-ablated lungs. ***P<0.0008, two-tailed unpaired Student's t-test; n=3 mice.

FIGS. 5A-5F shows that PATS cells originate from alveolar stem cells after lung injury in vivo. FIG. 5A is a schematic showing an experimental workflow for the sequential administration of tamoxifen, followed by bleomycin injury and tissue collection for analysis using Sftpc-CreER; R26R-tdTomato mice. FIG. 5B show a time course of immunostaining for CLDN4, Sftpc-tdt and LGALS3 after bleomycin injury. Scale bars, 10 μm. Images are representative of three mice. FIG. 5C is a graph showing quantificationt of CLDN4+, CLDN4+LGALS3+ and LGALS3+ cells at different times after injury. n=3 mice. FIG. 5D is a graph showing cell length of CLDN4+, CLDN4+LGALS3+ and LGALS3+ cells. *P=0.049 (CLDN4+ versus CLDN4+LGALS3+) and 0.0235 (CLDN4+ versus LGALS3+), two-tailed unpaired Student's t-test; n=30 cells from three mice. FIG. 5E is a schematic showing the pneumonectomy injury model. FIG. 5F is a schematic showing transition from AEC2 to AEC1 through different PATS subtypes.

FIGS. 6A-6H show lineage tracing revealed that PATS cells generate AEC1s. FIG. 6A is a UMAP of the epithelial populations in cultured alveolar organoids (n=4,573 cells). The arrow indicates the select cell populations in the oval that are shown in FIG. 6B. FIG. 6B are UMAP plots showing the expression of the indicated genes in the selected populations (oval in FIG. 6A; n=574 cells). FIG. 6C is a schematic showing the experimental workflow for the sequential administration of bleomycin (injury) or PBS (control), followed by tamoxifen (to label Krt19-expressing cells) in Krt19-CreER; R26R-tdTomato mice. FIG. 6D are images showing immunostaining for SFTPC, Krt19-tdt and AGER. The white arrows indicate AGER+Krt19-tdt+ cells. Scale bars, 30 μm. Images are representative of three mice, repeated independently with similar results. FIG. 6E are images showing co-staining for SFN, Krt19-tdt and AGER. The white arrows indicate SFN+Krt19-tdt+ cells. Scale bars, 50 μm. Images are representative of three mice, repeated independently with similar results. FIG. 6F is a graph showing quantification of AGER+Krt19-tdt+ cells in total Krt19-tdt+ cells p=0.0318 (one-tailed, Mann-Whitney). n=3 mice. FIG. 6G are images showing immunostaining for CLDN4, Krt19-tdt and LGALS3. The arrows indicate CLDN4+Krt19-tdt+ cells. Scale bars, 50 μm. Images are representative of three mice, repeated independently with similar results. The arrowheads indicate a LGALS3+Krt19-tdt+ cell. FIG. 6H is a graph showing quantification of KRT8+Krt19-tdt+ cells in total Krt19-tdt+ cells. p=0.0318, (one-tailed, Mann-Whitney). n=3 mice.

FIG. 7A is a graph showing KEGG analysis reveals pathways enriched in PATS. The web-based tool EnrichrScale was used to determine the log 2-transformed combined score values. FIG. 7B is a heatmap that shows expression of known target genes of indicated signalling pathways in AEC2, proliferating AEC2 (AEC2pro), PATS and AEC1 in alveolar organoids (n=4,573 cells) and LPS-treated murine lung (n=13,204 cells). Scale indicates z-score. FIG. 7C are violin plots for senescence (top) and DNA-damage-response pathways (bottom) in the indicated cell populations from the LPS-injury model in vivo (n=13,039 cells). The black dots represent cells. The violin bodies indicate the distribution of the cells.

FIG. 8A are images showing staining for β-galactosidase activity in bleomycin-injured (right) and control (left) lungs. Scale bars, 100 μm. FIG. 8B are images showing immunostaining for CDKN1A, Sftpc-tdt and AGER in control (top) and bleomycin-injured (bottom) lungs. The arrowheads indicate CDKN1A+ cells. The white dotted lines indicate AEC1s and the dotted lines outline tdt+ cells. Scale bars 50 μm. FIG. 8C are images showing immunostaining for λH2AX, Sftpc-tdt and AGER in control (top) and bleomycin-injured (bottom) lungs. Scale bars 50 μm. FIG. 8D is a graph showing the proportion of the total λH2AX+Sftpc-tdt+ cells in control and bleomycin-injured mice on day 10 that are LGALS3+. *P<0.0318, one-tailed Mann-Whitney test; n=3 mice. FIG. 8E are images showing staining for β-galactosidase activity in DT-treated and control lungs. Scale bars, 100 μm. FIG. 8F are images showing immunostaining for CDKN1A, LGALS3 and AGER in control (top) and DT-treated lungs (bottom). The arrowheads indicate CDKN1A+ cells. Scale bars 20 μm. FIG. 8G is a graph showing the proportion of the total λH2AX+ cells in control and DT-treated lungs that are LGALS3+. *P=0.0318, one-tailed Mann-Whitney test; n=3 mice. FIG. 8H is a schematic of 2D culture of AEC2s. FIG. 8I are images showing immunostaining for Sftpc-GFP, λH2AX and AGER in 2D culture of AEC2s. The white arrows indicate cells with DNA-damage marker. Scale bars 20 μm. Images are representative of three mice, repeated independently with similar results. DAPI stains nuclei.

FIG. 9A is a schematic showing an experimental workflow for the sequential administration of tamoxifen followed by PBS or bleomycin (day 0) administration, Nutlin-3a or DMSO treatment (days 8-18) and tissue collection (day 20) for analysis using Sftpc-CreER; R26R-tdTomato mice. FIG. 9B is a graph showing the proportion of the total Sftpc-tdt+ cells mice treated with PBS+Nutlin-3a, bleomycin+DMSO, and bleomycin+Nutlin-3a that are AGER+. *P=0.0201, two-tailed unpaired Student's t-test; n=3 mice. FIG. 9C is a schematic of alveolar organoid culture treated with Nutlin-3a. FIG. 9D are images showing immunostaining for Ki67 (green) and AGER (grey) in control or Nutlin-3a treated alveolar organoids. Scale bar: 30 μm. FIG. 9E is a schematic showing the experimental workflow for the sequential administration of tamoxifen to delete TP53 in AEC2s, followed by bleomycin injury (day 0) in Sftpc-CreER; R26R-tdTomato; Trp53fl/fl or control mice (Sftpc-CreER; R26R-tdTomato; Trp53+/+). FIG. 9F is a graph showing the proportion of the total Sftpc-tdt+ cells from for SFTPC, Sftpc-tdt and AGER, and CLDN4, Sftpc-tdt and LGALS3 in control and Trp53-knockout mice that are AGER+. **P<0.0001, two-tailed unpaired Student's t-test; n=3 mice. FIG. 9G is a graph showing the proportion of CLDN4+, CLDN4+LGALS3+ and LGALS3+ cells (bars from left to right, respectively) in bleomycin-treated lungs. P=0.048 (CLDN4) and 0.0013 (LGALS3), two-tailed unpaired Student's t-test; n=3 mice. FIG. 9H is a graph showing the proportion of the total Sftpc-tdt+ cells from Sftpc-tdt and SFN in control and Trp53-knockout mice treated with bleomycin that are p21+. ***P<0.0001, two-tailed unpaired Student's t-test; n=3 mice.

FIG. 10A is a graph showing the distribution of H3K4me3 peaks in PATS marker gene loci in PATS (upper line) and homeostatic AEC2s (lower line). FIG. 10B is a schematic showing the experimental workflow for bleomycin-induced lung injury in Sftpc-CreER; R26R-td-Tomato; Ctgf-GFP mice, followed by PATS sorting and ChIP analysis. FIG. 10C is ChIP enrichment for TRP53, H3K4me3 (active promoter) and H3K27ac (active enhancer) shown in IGV. FIG. 10D IGV tracks does not show enrichment for TP53 binding in genomic loci corresponding to known targets of AEC1 gene loci. FIG. 10E IGV tracks does not show enrichment for TP53 binding in genomic loci corresponding to known targets of AEC2 gene loci.

FIG. 11A is a UMAP that shows scRNA-seq data from AECs in healthy and IPF lungs (n=11,725 cells). FIG. 11B are UMAP plots that indicate the expression of genes in scRNA-seq data for healthy and IPF lungs. FIG. 11C shows Hematoxylin and Eosin staining on IPF lung tissue sections. Representative image depicting fibrotic (right side square box) and non-fibrotic (left side square box) regions in IPF lung. Scale bar indicates 200 μm. FIG. 11D are images showing immunostaining for ACTA2, SFN and SFTPC in healthy human lungs (left), and non-fibrotic (middle) and severe-fibrotic (right) regions of lungs from patients with IPF. FIG. 11E is a graph showing the proportion of SFTPC+, SFTPC+SFN+ and SFN+ cells in healthy lungs, and non-fibrotic and fibrotic regions of IPF lungs; n=3 human samples. FIG. 11F are images showing immunostaining for SFN, CLDN4 and AGER in a fibrotic region of an IPF lung. FIG. 11G is a graph showing the proportion of the total SFN+ cells in non-fibrotic and severe-fibrotic regions of IPF lungs that are CLDN4+. *P=0.0218, one-tailed Mann-Whitney test; n=3 human samples. FIG. 11H are images showing immunostaining for SFN, KRT17 and TP63 in a region of an IPF lung with severe fibrosis (arrowheads indicate SFN+ KRT17+TP63+ cells). FIG. 11I is a graph showing the proportion of total SFN+ cells that are KRT17+ or KRT17+ TP63+ in non-fibrotic regions compared with regions of severe fibrosis in IPF lungs. *P=0.0318, one-tailed Mann-Whitney test; n=3 human samples. FIG. 11J are UMAP plots from scRNA-seq data show enrichment of candidate signaling pathways in healthy and IPF lungs (n=11,725 cells). FIG. 11K are violin plots showing expression of IPF-relevant genes in the indicated cell types/states in control and IPF lungs (n=11,725 cells). The violin plots indicate the cell distributions in healthy and IPF lungs. FIG. 11L is a graph showing the proportion of total SFN+ cells that are CDKN1A+. *P=0.0318, one-tailed Mann-Whitney test; n=3 human samples. FIG. 11M is a graph showing the proportion of total SFN+ cells that are λH2AX+. *P=0.0218, one-tailed Mann-Whitney test; n=3 healthy and 4 IPF human samples. Insets: single-channel images of the region in a white box.

DETAILED DESCRIPTION

Figure 1A:
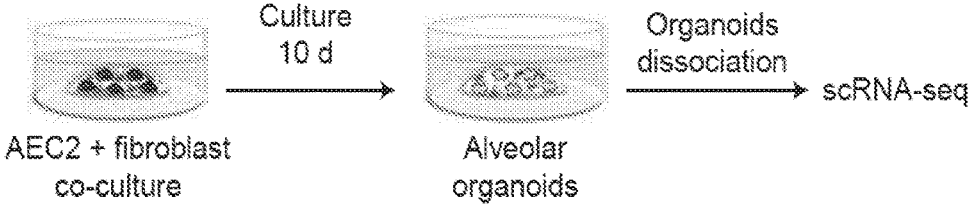
FIGS. 1A-1H Previously unknown alveolar epithelial cell states in ex vivo organoids revealed by scRNA-seq.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Definitions

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The term "disease" as used herein includes, but is not limited to, any abnormal condition and/or disorder of a structure or a function that affects a part of an organism. It may be caused by an external factor, such as an infectious disease, or by internal dysfunctions, such as cancer, cancer metastasis, and the like.

The term "effective amount" or "therapeutically effective amount" refers to an amount sufficient to effect beneficial or desirable biological and/or clinical results.

As used herein, "treatment" or "treating" refers to the clinical intervention made in response to a disease, disorder, or pathogen infection manifested by a patient or to which a patient may be susceptible. The aim of treatment includes the alleviation or prevention of symptoms, slowing or stopping the progression or worsening of a disease, disorder, disease causative agent (e.g., bacteria, viruses, a chemotherapeutic agent, radiation), or condition and/or the remission of the disease, disorder or condition.

Unless otherwise defined, all technical terms used herein have the same meaning as commonly understood by one of ordinary skill in the art to which this disclosure belongs.
PATS Stem cells undergo dynamic changes in response to injury to regenerate lost cells. However, the identity of transitional states and the mechanisms that drive their trajectories remain understudied. Using lung organoids, multiple in vivo repair models, single-cell transcriptomics and lineage tracing, the inventors have found that alveolar type-2 epithelial cells undergoing differentiation into type-1 cells acquire pre-alveolar type-1 transitional cell state (PATS) en route to terminal maturation. The inventors have further found that transitional cells undergo extensive stretching during differentiation, making them vulnerable to DNA damage. The inventors have determined that cells in the PATS show an enrichment of TP53, TGFβ, DNA-damage-response signaling and cellular senescence. As described in the examples, gain and loss of function as well as genomic binding assays revealed a direct transcriptional control of PATS by TP53 signaling. The inventors have also found that accumulation of PATS-like cells in human fibrotic lungs was observed, suggesting persistence of the transitional state in fibrosis. The results described in the example section herein thus implicate a transient state associated with senescence in normal epithelial tissue repair and its abnormal persistence in disease conditions.

Using a novel alveolar epithelial type-1 cell (also known as pneumocyte type-I) ablation model, the inventors established a first genetic model that develops lung fibrosis. In addition, the inventors have developed an ex vivo lung fibrosis models that uses co-culture of above described novel transitional cell state (PATS) and alveolar fibroblasts. These novel in vivo and ex vivo fibrosis models are scalable and allows for disease modeling and drug screening. These features are often found in progressive lung disease and one can observe enrichment of cells in a PATS-like state in human fibrotic lungs, indicating persistence of the transitional state in fibrosis. The studies provided herein thus implicate a transient state associated with senescence in normal epithelial tissue repair and its abnormal persistence in disease conditions.

As used herein, the term "organoid" refers to self-organized three-dimensional (3D) structures or entities that are derived from stem cells grown in culture. Organoids cultures can replicate the complexity of an organ or can express selected aspects of an organ, such as by producing only certain types of cells. Alternatively, at certain stages before differentiation, they can be comprised only of stem cells.

Stem cells are cells that have the ability to both replicate themselves (self-renew) and give rise to other cell types. When a stem cell divides, a daughter cell can remain a stem cell or become a more specialized type of cell, or give rise to other daughters that differentiate into one or more specialized cell types. Two types of mammalian stem cells are: pluripotent embryonic stem cells that are derived from undifferentiated cells present in blastocyst or pre-implantation embryos, and adult stem cells that are found in adult tissues or organs. Adult stem cells can maintain the normal turnover or regeneration of the tissue or organ and can repair and replenish cells in a tissue or organ after damage.

As used herein, the term "stem cell" refers to an undifferentiated cell that is capable of proliferation and self-renewal and of giving rise to progenitor cells with the ability to generate one or more other cell types, or to precursors that can give rise to differentiated cells. In certain vases the daughter cells or progenitor or precursor cells that can give rise to differentiated cells. In certain cases the daughter cells or progenitor or precursors cells can themselves proliferate and self-renew as well as produce progeny that subsequently differentiate into one or more mature cell types.

A progenitor cell refers to a cell that is similar to a stem cell in that it can either self-renew or differentiate into a differentiated cell type, but a progenitor cell is already more specialized or defined than a stem cell.

Stems cells of the present disclosure can be derived from any animal, including but not limited to, human, mouse, rat, rabbit, dog, pig, sheep, goat, and non-human primates.

The stem cells that can be used in the methods and models of the present disclosure can be normal (e.g., cells from healthy tissue of a subject) or abnormal cells (e.g., transformed cells, established cells, or cells derived from diseased tissue samples).

In some embodiments, the cells used in the methods and models of the present disclosure can be derived from lung stem cells. Division of lung stem cells can promote renewal of the lung's structure. Examples of lung stem cells include, but are not limited to tracheal basal cells, bronchiolar secretory cells (also known as club cells or Clara cells), club variant cells, alveolar epithelial progenitor (AEP) cells, clara variant cells, distal lung progenitors, p63+ Krt5– airway cells, lineage negative epithelial progenitors, bronchioalveolar stem cells (BASCs), Sox9+p63+ cells, neuroendocrine progenitor cells, distal airway stem cells, submucosal gland duct cell, induced pluripotent stem cell-derived lung stem cells and alveolar type 2 epithelial (referred to herein as AEC2 or AT2) cells.

In some embodiments, the cells used in the methods and models of the present disclosure can be derived from basal stem cells from organs including, skin, mammary gland, esophagus, bladder, prostate, ovary, and salivary glands.

Methods and Models

Accordingly, one aspect of the present disclosure provides the identification of a newly-identified transitional cell state (PATS) in alveolar regeneration. This transitional cell state induces lung fibroblasts conversion into pathological fibroblasts (myofibroblasts). Further, this transitional cell state is also found in human fibrotic (e.g., idiopathic lung fibrosis and interstitial lung diseases) lungs.

Another aspect of the present disclosure provides a model system to ablate lung alveolar type-I cells (also known as pneumocyte type-I) that leads lung fibrosis, emphysema (similar to the one observed in human combined pulmonary fibrosis and emphysema syndrome (CPFE)).

In some embodiments, the model system comprises an animal model. In one embodiment, the animal comprises a mouse. In some embodiments, the animal comprises any animal that has lungs.

Another aspect of the present disclosure provides a method of generating a lung injury organoid model, the method comprising, consisting of, or consisting essentially of: i) providing a co-culture of cells in a culture medium adapted for the culture of said cells, wherein the co-culture comprises pre-alveolar type-1 transitional cell state (PATS) cells and alveolar fibroblasts; ii) contacting the culture medium with one or more agents; iii) analyzing the biological effect of the agent on at least one expression marker of the PATS cells and/or the alveolar fibroblasts relative to a control cell culture medium that has not been contacted by the agent.

Alveolar fibroblasts are cells that are involved in the lung repair/fibrosis process in the lung. Alveolar fibroblasts can synthesize extracellular matrix and collagen and produce stroma in animal tissues. Examples of alveolar fibroblasts include but are not limited to, human fetal lung fibroblast cells (e.g., HFL1, MRC-5, 2BS, and WI38), Chinese hamster lung fibroblast (V-97) cell, C57BL/6 mouse primary lung fibroblasts, and CC-2512 cells.

In some embodiments, the alveolar fibroblasts are lipofibroblasts. In some embodiments, the alveolar fibroblasts have disease-state characteristics.

The term "disease-state characteristics" as used herein refers to phenotypic or genotypic properties of a cell that indicates the cell is a disease cell. These characteristics can be the expression of certain markers or morphological changes in the cell that indicate disease state. In some embodiments, disease-state characteristic of alveolar fibroblasts comprises lipofibroblast cells that express ACTA2, the presence of myofibroblast cells, and/or cell changes from a sellate shape to a banded shape.

In some embodiments, the PATS cells are isolated from diseased tissue.

The term "diseased tissue" refers to the tissue of subject (e.g., human or animal model) that is abnormal compared to healthy tissue. The diseased tissue can be obtained from the tissue of a living or deceased subject. Example of diseased tissue include, but are not limited to, chronic obstructive pulmonary disease (COPD) lung tissue, pulmonary fibrosis lung tissue, idiopathic pulmonary fibrosis lung tissue, emphysema lung tissue, lung cancer tissue, Sarcoidosis lung tissue, interstitial pneumonia lung tissue, sepsis lung tissue, ling tissue having viral and bacterial infections, acute respiratory distress syndrome lung tissue, and bronchopulmonary dysplasia lung tissue. In some embodiments, the PATS cells are isolated from pulmonary fibrosis lung tissue or idiopathic pulmonary fibrosis lung tissue.

Lung cancer cells can be isolated from a subject suffering from a lung cancer. The lung cancer cells can be isolated from a primary lung tumor or a secondary lung tumor (e.g., a cancer that starts in another tissue and metastasizes to the lungs). Examples of lung cancer cells include but are not limited to small cell lung cancer cells or non-small cell lung cancer cells, including but not limited to, small cell carcinoma, combined small cell carcinoma, adenocarcinoma, squamous cell carcinoma, large cell carcinoma, pancoast tumor cells, neuroendocrine tumor, or lung carcinoid tumor cells. Established lung cancer cell lines can also be used in the methods and models of the present disclosure. Lung cancer cell lines that can be used in the methods and models of the present disclosure can be found on the ATCC website. Examples of lung cancer cell lines include but are not limited to, EML4-ALK Fusion-A549 Isogenic cell line, NCI-H838 [H838], HCC827, SK-LU-1, HCC2935, HCC4006, NCI-H1819 [H1819], NCI-H676B [H676B], Hs 618.T, HBE4-E6/E7 [NBE4-E6/E7], NCI-H1666 [H1666, H1666], NCI-H23 [H23], NCI-H1435 [H1435], NCI-H1563 [H1563], 703D4, and NCI-H1688 [H1688], NCI-H187 [H187], NCI-H661 [H661], NCI-H460 [H460], NCI-H1299, NCI-H1155 [H1155], DMS 114, NCI-H69 [H69], DMS 79, DMS 53, SW 1271 [SW1271, SW1271], SHP-77, NCI-H209 [H209], NCI-H146 [H146], NCI-H345 [H345], NCI-H1341 [H1341], DMS 153, NCI-H82 [H82], NCI-H1048 [H1048], NCI-H128 [H128], NCI-H446 [H446], NCI-H128 [H128], NCI-H510A [H510A, NCI-H510], H69AR. HLF-a, Hs 913T, GCT [Giant Cell Tumor], SW 900 [SW-900, SW900], LL/2 (LLC1), HBE135-E6E7, Tera-2, NCI-H292 [H292], sNF02.2, NCI-H1703 [H1703], NCI-H2172 [H2172], NCI-H2444 [H2444], NCI-H2110 [H2110], NCI-H2135 [H2135], NCI-H2347 [H2347], NCI-H810 [H810], NCI-H1993 [H1993], and NCI-H1792 [H1792].

In some embodiments, the PATS cells are isolated from healthy tissue (e.g., normal lung tissue).

The term "tissue" as used herein refers to an aggregate of cells that can be of a particular kind together with their intercellular substance that form the structural material of the subject from which the tissue is obtained. In some embodiments of the disclosure, the PATS cells can be isolated and purified from the tissue.

In some embodiments of the disclosure, the PATS cells can be generated by exposing lung epithelial cells (e.g., AEC2s or AEC1s) to an injury-causing agent in vivo or in vitro.

The term "injury-causing agent" as used herein refers to an agent that is capable of converting or transitioning a healthy cell to a diseased-cell state. The term "injury-causing agent" as used herein also refers to an agent that is capable of ablating a normal cell such that a disease-state cell arises.

The injury-causing agent can be, for example, a chemotherapy agent (e.g., bleomycin, tamoxifen, actinomycin-D, mitomycin, taxanes, and gemcitabine), an exotoxin (e.g., diphtheria toxin (DT)), a virus, a bacterium, a fungus, asbestos, chemical toxic agents, or irradiation.

In some embodiments, the injury-causing agent can be a pathogen (e.g., a bacterium, virus, or fungus) that is capable of infecting lung tissue of humans or any animal with lungs.

Bacteria that can infect lungs include, but are not limited to *Bordetella pertussis, Streptococcus pneumonia, Haemophilus influenza, Staphylococcusaureus, Moraxellacatarrhalis, Streptococcuspyogenes, Pseudomonas aeruginosa, Neisseriameningitidis, Klebsiellapneumoniae.*

Viruses that can infect lungs include, but are not limited to, 229E (alpha coronavirus), NL63 (alpha coronavirus), OC43 (beta coronavirus), HKU1 (beta coronavirus), MERS-CoV (the beta coronavirus that causes Middle East Respiratory Syndrome, or MERS), SARS-CoV (the beta coronavirus that causes severe acute respiratory syndrome, or SARS), or SARS-CoV-2 (the novel coronavirus that causes coronavirus disease 2019, or COVID-19), an influenza-A virus (e.g., H1N1, H7N9, low pathogenic avian flu, high pathogenic avian flu, or H5N1), an influenza-B virus, respiratory syncytial virus (RSV), or an enterovirus (e.g. enterovirus 71). In some embodiments, the virus is SARS-CoV-2.

Fungus that can infect lungs include, but are not limited to, Aspergillosis.

In some embodiments, the culture medium and/or subjects (e.g., mice) used in the methods and models of the disclosure comprise a platelet-derived growth factor receptor (e.g., platelet-derived growth factor receptor-A, platelet-derived growth factor receptor-B, or platelet-derived growth factor receptor-AB).

In some embodiments, the culture medium and/or subjects (e.g., mice) used in the methods and models of the disclosure comprises a platelet-derived growth factor receptor (PDGFR) ligand. In some embodiments, the PDGFR ligand is platelet-derived growth factor (PDGF). PDGF is a growth factor that can regulate cell growth and division. In some embodiments, the PDGFR ligand is platelet-derived growth factor subunit A (PDGF-A), platelet-derived growth factor subunit B (PDGF-B), platelet-derived growth factor subunit C (PDGF-C), platelet-derived growth factor subunit D (PDGF-D), and/or platelet-derived growth factor subunit AB (PDGF-AB). Human genes that encode proteins that belong to the PDGF family include FIGF, PDGFA, PDGFB, PDGFC, PDGFd, PGF, VEGF, VEGF41, VEGFB, and VEGFC.

In some embodiments, the methods and models of the present disclosure comprise the use of PDGF signaling peptides, PDGF receptors, PDGF agonists, PDGFR agonists, PDGF antagonists, PDGFR antagonists, or any agent that is capable of modulating the PDGF-PDGFR signaling pathway. In other embodiments, the methods and models of the present disclosure comprise the use of a pharmacological blockade of PDGF ligands and/or PDGFR receptors.

Modulators of the PDGF-PDGFR signaling pathway include substrates, inhibitors, activators, neurotransmitters, agonists, antagonists, inverse agonists, inverse antagonists, partial agonists, and partial antagonists. Modulators of the PDGF-PDGFR signaling pathway include, but are not limited to, PDGF isoform antagonists, PDGFR activation blockers, agents capable of increasing or decreasing the expression of PDGF and/or PDGFR in a cell, chemical compounds, such as endogenous metabolites, non-endogenous metabolites, synthetic chemical compounds, polypeptides, amino acid residues, nucleic acids, siRNA, and antibodies (e.g., neutralizing antibodies).

Examples of modulators of the PDGF-PDGFR signaling pathway include but are not limited to, fibronectin peptides, Ras-GAP, tyrosine phosphatases (e.g., PTP1B, TC-PTP, PTPRJ/DEP-1), SHP-2, integrins, the low density lipoprotein receptor-related protein, hyaluronan receptor CD44, sorafenib, nilotinib, pazopanib, regorafenib, AG1295 and AG1296, celecoxib, etoricoxib and DFU, cyclooxygenase-2 (COX-2) inhibitors (coxibs), pazopanib HCl, pazopanib, radotinib, AZD2932, toceranib phosphate, TAK-593, crenolanib, toceranib, SU14813, SU14813 maleate, orantinib, SU 4312, Sunitinib Malate, Linifanib, KG 5, N-Desethyl Sunitinib, CP-673451, VEGFR2 Kinase Inhibitor II, VEGFR2 Kinase Inhibitor II, AC710 Mesylate, AC710, DMPQ dihydrochloride, ripretinib, lenvatinib, nintedanib, regorafenib, sunitinib, pnatibib, sunitnib malate, TG 100572, ilorasertib, imatinib, axitinib, imatinib mesylate, pazopanib, crenolanib, SU 5402, avapritinib, ripretinib, cediranib, CP 673451, dovitinib, TAK 593, toceranib, PDGFRa kinase inhibitor-1, SU16f, agonistic human monoclonal autoantibodies targeting PDGFRα, and non-agonistic human monoclonal autoantibodies targeting PDGFRα, and or derivatives thereof.

As used herein, the term "agonist" refers to a modulator that binds to a receptor (e.g., PDGFR) or protein (e.g., PDGF) and activates the receptor or protein to produce a biological response.

As used herein, the term "antagonist" refers to a modulator or ligand that blocks, impedes, or dampens a biological response by binding to and blocking a receptor or protein rather than activating it.

As used herein, the term "inverse agonist" refers to a modulator or ligand that binds to the same receptor as an agonist but induces a biological response opposite to that agonist.

As use herein, the term "partial antagonist" refers to a modulator or ligand that can bind to a receptor but does not completely block the receptor's effects, but rather decreases the maximum potential of the receptor.

In some embodiments, the culture medium used in the methods and models comprises an agent that is capable of maintaining PDGFR (e.g., PDGFR-A, PDGFR-B, or PDGFR-AB) expression in a cell. In some embodiments, the agent capable of maintaining PDGFR-A expression in a cell is Ro 5-3335 or AI-10-49.

In some embodiments, the agent capable of maintaining PDGFRA expression in a cell is any molecule that can modulate RUNX (e.g., RUNX1, RUNX2, or RUNX3) or core binding factor (CBF) related family of proteins (e.g., CBF-β).

Examples of molecules that regulate RUNX or CBF related proteins can be RUNX and/or CBF substrates, inhibitors, activators, neurotransmitters, agonists, antagonists, inverse agonists, inverse antagonists, partial agonists, and partial antagonists.

Molecules that modulate RUNX and/or CBF can be molecules that interfere with the protein-protein interaction between RUNX and CBF. These modulators can be inhibitors of RUNX (e.g., RUNX1, RUNX2, or RUNX3) or inhibitors CBF-β. Examples of RUNX or CBF modulators include, but are not limited to, Ro 5-3335, AI-10-49, CADD522, muramyl dipeptide, L-quebrachitol, L-ascorbic acid 2-phosphate, ascorbic acid 2-phosphate magnesium, 2-pyridyl benzimidazole AI-4-57, RUNX1/MTG8 fusion protein, and a neutralizing antibody against RUNX1, RUNX2, RUNX3, and/or CBFb, and/or derivatives thereof, An "agent" as used herein refers to a small molecule, protein, peptide, gene, compound, or other pharmaceutically active ingredient. In some embodiments, the agent can be used for the treatment, prevention, or mitigation of a disease (e.g., lung fibrosis).

PATS cell expression markers refer to gene transcripts that are expressed on PATS cells or PATS-like cells. In some embodiments, PATS markers are unique to the PATS cell state and are not typically expressed on related cell states (e.g., AEC2s or AEC1s). PATS cell markers can comprise CLDN4, KRT19, SFN, LGALS3, SOX4, S100A2, PTGS2, KRT17, KRT8, CALS1, MMP7, PRSS2, IGFBP7, COL1A1, MDK, TAGLN, GDF15, TM4SF1 TP63, and/or CTSE.

In some embodiments, the PATS markers can comprise a marker signature of two or more markers that are co-expressed. In some embodiments, the PATS marker signature is CLDN4, LGALS3, and LGALS3. In some embodiments, the PATS marker signature is CLDN4, KRT19, and SFN. In some embodiments, the PATS marker signature is CALD1, PRSS2, MMP7, and S100A2.

In some embodiments, the PATS marker signature is TP63, KRT17 and COL1A1.

In some embodiments, the PATS marker signature is AREG, TGFβ1, TGFβ2 and TIMP1.

Alveolar fibroblasts expression markers refer to gene transcripts that are expressed on alveolar fibroblasts cells. Alveolar fibroblasts can comprise Pdgfra.

Another aspect of the present disclosure provides a method of generating an ex vivo model for lung fibrosis, the method comprising: i) providing a culture of alveolar cells (e.g. AEC1 cells) that have undergone ablation in vivo in a culture medium adapted for the culture of said cells; ii) contacting the culture medium with one or more agents; iii) analyzing the biological effect of the agent on at least one expression marker the alveolar cells (e.g. AEC1 cells) relative to a control cell culture medium that has not been contacted by the agent.

The term "ablation" as used herein refers to the removal or destruction of a tissue or cell, or their function. Ablation can be caused by surgery, hormones, drugs, radiofrequency, heat, or other methods that cause destruction of the tissue or cell.

In some embodiments, the alveolar cells (e.g. AEC1 cells) have undergone at least one round of ablation (e.g., at least one, two, three, four, five, six, seven, eight, nine, or ten rounds of ablation). In some embodiments, the alveolar cells (e.g. AEC1 cells) have undergone between one and five rounds of ablation. In some embodiments, the cells have undergone ablation alone or in combination with other injury models described herein.

In some embodiments, the alveolar cells (e.g. AEC1 cells) have undergone repeated ablation. In some embodiments, the repeated ablation can occur over the course of about three days to about two weeks. In some embodiments, the repeated ablation can occur over the course of about three days to about one year.

In some embodiments, the alveolar cells (e.g. AEC1 cells) have undergone ablation by being exposed to an injury-causing agent. In some embodiments, the injury-causing agent is bleomycin, diphtheria toxin (DT), tamoxifen, a virus, a bacterium, or a fungus.

In some embodiments, the ablated cells express aSMA and/or ACTA2. In some embodiments, the ablated cells exhibit characteristics of a fibromyocyte cell.

Yet another aspect of the present disclosure provides, a method of identifying pre-alveolar type-1 transitional cell state (PATS) cells, the method comprising: i) obtaining lung cells; and ii) screening the cells for one or more markers, wherein the presence of the one or more markers indicates the presence of PATS cells.

In some embodiments, the lung cells can be selected from the group consisting of tracheal basal cells, bronchiolar secretory cells (also known as club cells or Clara cells), club variant cells, alveolar epithelial progenitor (AEP) cells, clara variant cells, distal lung progenitors, p63+ Krt5– airway cells, lineage negative epithelial progenitors, bronchioalveolar stem cells (BASCs), Sox9+p63+ cells, neuroendocrine progenitor cells, distal airway stem cells, submucosal gland duct cell, induced pluripotent stem cell-derived lung stem cells and alveolar type 2 epithelial (AEC2) cells.

In some embodiments, the lung cells can be selected from the group consisting of AEC2 cells, AEC1 cells, or alveolar macrophages.

In some embodiments, the lung cells are obtained from the lung of a patient suffering from chronic obstructive pulmonary disease (COPD), pulmonary fibrosis, idiopathic pulmonary fibrosis, emphysema, lung cancer, Sarcoidosis, interstitial pneumonia, sepsis, a viral infection, a bacterial infection, a fungal infection, acute respiratory distress syndrome, and/or bronchopulmonary dysplasia.

In some embodiments, the method of identifying pre-alveolar type-1 transitional cell state (PATS) cells further comprises contacting the alveolar cells with an injury-causing agent. In some embodiments, the agent is bleomycin, diphtheria toxin (DT), tamoxifen, a virus, a bacterium, or a fungus.

Another aspect of the present disclosure provides an ex vivo lung fibrosis model that uses co-culture of above described novel transitional cell state (PATS) and alveolar fibroblasts that is scalable and allows for disease modeling and drug screening.

Another aspect of the present disclosure provides a method of generating an in vivo model of generating fibrosis in lung and other tissues. Like the in vitro and ex vivo models of the present disclosure, the in vivo models can be used, for example, to test the ability for therapeutic agent to treat or prevent disease. The in vivo models of present disclosure can utilize a variety of animal subjects (e.g., mouse, rat, rabbit, monkey, or pig or any animal that is capable of modeling fibrosis).

An in vivo model refers to the use of a whole living animal to investigate the effect of an agent and to study the biological processes of disease (e.g., lung fibrosis).

Another aspect of the present disclosure provides a method of generating an in vivo model of generating fibrosis in lung and other tissues, the method comprising: i) introducing a genetic loss of PDGF ligands and/or PDGF receptor (PDGFR) signaling in a subject; and/or ii) administering an agent to a subject that can modulate (e.g., block, enhance, increase, or decrease) PDGF-PDGFR signaling; and iii) analyzing cells from the subject to determine the biological effect of the genetic loss of PDGF ligands and/or PDGF receptor (PDGFR) signaling and/or the biological effect of the agent that can modulate (e.g., block enhance, increase, or decrease) PDGF-PDGFR signaling relative to a normal control subject.

In some embodiments, the agent that can block PDGF-PDGFR signaling comprises a PDGFR inhibitor, neutralizing antibodies against PDGF ligands and/or PDGF receptor (PDGFR).

Another aspect of the present disclosure provides a method of generating an in vivo model of generating fibrosis in lung and other tissues, the method comprising: i) introducing a genetic loss of RUNX1, RUNX2, RUNX3, or CBFP in a subject; and/or ii) administering an agent to a subject that can modulate (e.g., inhibit) RUNX1, RUNX2, RUNX3, or CBFP; and iii) analyzing cells from the subject to determine the biological effect of genetic loss of RUNX1, RUNX2, RUNX3, or CBFP and/or the biological effect of modulating RUNX1, RUNX2, RUNX3, or CBFP relative to a normal control subject.

In some embodiments, the RUNX1, RUNX2, RUNX3, or CBFP modulator is a small molecule inhibitor are a neutralizing antibody against RUNX1, RUNX2, RUNX3, and/or CBFβ.

In some embodiments, the models of the present disclosure are fibrosis models of lung fibrosis, cardiac fibrosis, liver fibrosis, kidney fibrosis, intestinal fibrosis, skin fibrosis, and/or bone marrow fibrosis. In some embodiments, the models of the present disclosure are lung fibrosis models that can model the impact of lung fibrosis on other tissues in the body, such as cardiac, liver, kidney, intestinal, skin, and/or bone marrow tissues.

In some embodiments, the cells of the models of the present disclosure are lung, heart, kidney, liver, intestine, skin, or bone marrow.

The following Examples are provided by way of illustration and not by way of limitation.

EXAMPLES

Materials and Methods

Mice.

Both male and female mice aged between 8-16 weeks were used for experiments. All of the mice were C57BL/6 unless otherwise indicated. The following mice were used for experiments: Sftpctm1(cre/ERT2)Blh (Sftpc-CreER), Krt19tm1(cre/ERT)Ggu/J (Krt19-CreER), Rosa26R-CAG-lsl-tdTomato (crossed with Sftpc-CreER), B6.Cg-Gt(ROSA)26Sortm14(CAG-tdTomato)Hze/J (R26R-tdTomato) (crossed with Krt19-CreER), Tg(SFTPC-GFP)#Heat (Sftpc-GFP)51, B6.Cg-Agertm2.1(cre/ERT2) Blh/J (Ager-CreER), B6-Gt(ROSA)26Sortm1(HBEGF)Awai/J (R26R-DTR), Mki67tm1.1Cle/J (Mki67-RFP), Tg(Ctgf-EGFP) FX156Gsat (Ctgf-GFP)15 and TP53fl/fl (mixed background). For lineage tracing with Sftpc-CreER; R26R-tdTomato mice, 3-5 doses of 2 mg tamoxifen (Sigma-Aldrich) per 20 g of body weight were given via oral gavage or intraperitoneal injection. For lineage tracing using Krt19-CreER; R26R-tdTomato, one dose of 1 mg tamoxifen per 20 g body weight was given via intraperitoneal injection 7 d after bleomycin injury or PBS administration. The animal experiments were approved by the Duke University Institutional Animal Care and Use Committee in accordance with US National Institutes of Health guidelines.

Bleomycin Injury.

For bleomycin-induced lung injury, 2.5 U kg-1 bleomycin was administered intranasally 2 weeks after the tamoxifen injection and the mice were monitored daily. Mice that were administered PBS served as controls. The mice were killed at different times after bleomycin injury.

Administration of DT.

Two weeks before DT administration, Ager-CreER; R26R-DTR mice received tamoxifen via intraperitoneal injection. One dose of 3 μg DT (Millipore, 322326) was administered via intraperitoneal injection and the mice were killed 6 d later for tissue collection and analysis.

Mouse Lung Dissociation and FACS.

Lung dissociation and FACS were performed as described previously11. Briefly, the lungs were intratracheally inflated with 1 ml enzyme solution (dispase, 5 U ml-1, Corning, 354235; DNase I, 0.33 U ml-1; and collagenase type I, 450 U ml-1, Gibco, 17100-017) in DMEM/F12 medium. The separated lung lobes were diced and incubated with 3 ml enzyme solution for 25 min at 37° C. with rotation. The reaction was quenched with an equal amount of medium containing 10% fetal bovine serum (FBS) and filtered through a 100-μm strainer. The cell pellet was resuspended in red-blood-cell lysis buffer (155 mM NH4Cl, 12 mM NaHCO$_3$ and 0.1 mM EDTA), incubated for 2 min and then filtered through a 40-μm strainer. The cell pellet was resuspended in DMEM/F12+2% BSA and stained with the following antibodies: EpCAM (eBioscience, G8.8), PDGFRa (BioLegend, APA5) and Lysotracker (Thermo Fisher, L7526) as described previously56. Sorting was performed using a BD FACS Vantage SE, SONY SH800S or Beckman Coulter MoFlo Astrios EQ system.

Alveolar Organoid Culture.

Alveolar organoid culture was performed as described previously (Barkauskas et al., 2013, J. Clin. Invest. 123: 1118-1123). Briefly, lineage-labeled AEC2s (1-3×10$^3$) from Sftpc-GFP or Sftpc-CreER; R26R-tdTomato mice treated with Tmx were sorted by FACS, and PDGFRα+(5×10$^4$) fibroblasts were resuspended in MTEC/Plus and mixed with an equal amount of growth-factor-reduced Matrigel (Corning, 354230). The medium was changed every other day.

Nutlin-3a Treatment.

For in vivo studies, Sftpc-CreER; R26R-tdTomato mice were injected with one dose of tamoxifen and rested for 2 weeks, followed by bleomycin or PBS administration. Nutlin-3a (Selleckchem, S8059) or DMSO (control) were administered by intraperitoneal injection 8 d after injury at a concentration of 20 mg kg-1 d-1 for ten consecutive days and samples were collected 20 d after the bleomycin administration. For ex vivo studies, alveolar organoids were cultured for 7 d, followed by Nutlin-3a (2 μm) treatment for 8 d before being harvested.

Droplet-Based scRNA-Seq.

Organoids embedded in Matrigel were incubated with Accutase solution (Sigma, A6964) at 37° C. for 20 min, followed by incubation with 0.25% trypsin-EDTA at 37° C. for 10 min. The trypsin was inactivated using DMEM/F12 Ham medium supplemented with 10% FBS and the cells were then resuspended in PBS supplemented with 0.01% BSA. After filtration through a 40-μm strainer, the cells were run through microfluidic channels at 3,000 μl h-1 at a concentration of 100 cells μl h-1 together with mRNA-capture beads at 3,000 μl h-1 and droplet-generation oil at 13,000 μl h-1. The DNA polymerase for the pre-amplification step (one cycle of 95° C. for 3 min; 15-17 cycles of 98° C. for 15 s, 65° C. for 30 s and 68° C. for 4 min; and one cycle of 72° C. for 10 min) was replaced by Terra PCR direct polymerase (Takara, 639271). The other processes were performed as described in the original droplet-based scRNA-seq protocol. The libraries were sequenced using a HiSeq X system with 150-bp paired-end sequencing.

Computational Analysis of scRNA-Seq.

Analysis of the scRNA-seq of alveolar organoids was performed by processing FASTQ files using dropSeqPipe v0.3 (https://hoohm.github.io/dropSeqPipe) and mapped on the GRCm38 genome reference with annotation version 91. Unique molecular identifier (UMI) counts were then further analysed using the R package Seurat v3.1.1 (ref. 58). The UMI count matrix of murine lungs treated with LPS (GSE130148)14 was obtained from Gene Expression Omnibus (GEO). The UMI counts were normalized using SCTransform. The cell barcodes for the clusters of interest were extracted and utilized for the velocyto run command in velocyto.py v0.17.15 (ref. 18) as well as to generate RNA velocity plots using velocyto.R v0.6 in combination with the R package SeuratWrappers v0.1.0 (https://github.com/satijalab/seurat-wrappers). Twenty-five nearest neighbours in slope calculation smoothing was used for the RunVelocity command. After excluding duplets, specific cell clusters were isolated based on enrichment for Sftpc, Sftpa1, Sftpa2, Sftpb, Lamp3, Abca3, Hopx, Ager, Akap5, Epcam, Cdh1, Krt7, Krt8, Krt18, Krt19, Scgb1a1 and Scgb3a1 as well as negative expressions of Vim, Acta2, Pdgfra and Pdgfrb in UMAP plots. The Rds files for control and idiopathic pulmonary fibrosis (IPF) lungs were obtained from GEO (GSE135893)29. Cell clusters of AEC2s, AEC1s, transitional AEC2s and KRT5-KRT17+ cells were extracted and analysed. Markers for each cluster, obtained using the FindAllMarkers command in Seurat, were utilized for identifying specific signalling pathways and gene ontology through Enrichr59. Z-scores were calculated based on the combined score in Kyoto Encyclopedia of Genes and Genomes (KEGG) to compare enrichment of signalling and ontology across different cell clusters. The results were displayed in heatmap format, generated using the R package pheatmap v1.0.12. Scaled data in Seurat object were extracted and the mean values of the scaled score of the gene members in each pathway were calculated and shown in UMAP as enrichment of signaling pathways. The gene-member lists of the utilized pathways were obtained from KEGG pathways60 and AmiGO61. The log 2 fold change and P values for each gene, extracted using the FindMarkers command in Seurat with the Wilcoxon rank-sum test, were shown in a volcano plot using the R package EnhancedVolcano v1.3.1 (https://github.com/kevinblighe/EnhancedVolcano) to show specific markers for Ctgf+ cells.

Mint-ChIP-Seq.

For the ChIP analysis of histone marks, PATS (CD31-CD45-CD140a-CD326+Ctgf-GFP+) cells were sorted from Ctgf-GFP mice on day 12 post bleomycin-induced lung injury. AEC2s (CD31–CD4 5–CD326+Lysotracker+Mki67–RFP– cells) were sorted from Mki67-RFP homeostatic mice. Mki67 mice were used to eliminate any cells that were undergoing cell division by negatively gating out RFP+ cells. The Mint-ChIP protocol was described previously62. For TP53 ChIP sequencing (ChIP-seq), PATS (CD31-CD45-Sftpc-tdTomato+Ctgf-GFP+ cells) were sorted from Sftpc-CreER; R26R-tdTomato; Ctgf-GFP mice on day 8 post bleomycin administration. In this case, we used a modified Mint-ChIP (version 3) protocol as described previously (https://tinyurl.com/udqksct). Following cell lysis, the chromatin was digested with 300 units of MNase (New England Biolabs, M0247S) at 37° C. for 10 min. T7 adaptor ligation was performed for 2 h and the samples then were split to give approximately 7,000 cells per antibody for histone-modification ChIP-seq. For TP53, we used approximately 40,000 cells for each replicate sample. The samples were incubated with histone H3 (H3; 1 µl; Active Motif, 39763), histone H3 µlysine 36 trimethylation (H3K36me3; 1 µl; Active Motif, 61101), histone H3 µlysine 4 trimethylation (H3K4me3; 1 µl; Abcam, ab8580), histone H3 µlysine 27 acetylation (H3K27ac; 1 µl; Active Motif, 39133) or TP53 (5 µl; Cell Signaling Technology, 2524T) antibodies overnight at 4° C. DNA was purified followed by T7-RNA polymerase mediated in vitro transcription at 37° C. for 3 h. Reverse transcription was performed as described in the original protocol, followed by library preparation using Terra direct PCR polymerase (TaKaRa, 639271). Two experimental replicates were performed for each cell population. The libraries were sequenced (at least 5×106 reads of 150-bp paired-ends per sample) using the Hiseq X or NovaSeq 6000 systems.

Computational Analyses of Mint-ChIP.

FASTQ files were generated using Bcl2fastq. Additional demultiplexing for Mint-ChIP FASTQ files were performed using Je63. Low-quality reads were trimmed out from the FASTQ files using trimmomatic v0.38. The reads were mapped on the mm10 genome reference using BWA65. The packages were run through a pipeline called MintChIP (https://github.com/jianhong/MintChIP). HOMER66 was used to generate bedGraph files to visualize peaks in Integrative Genomics Viewer (IGV). Peak calling for H3K4me3 was performed using the function getDifferentialPeaksReplicates.pl–region–size 1000–minDist 2000–C 0–L 50 of HOMER with normalization by H3. Motif analysis was performed using the findMotifsGenome.pl function of HOMER. A chart of called peaks for H3K4me3 was generated using deepTools68. Called peaks for each genomic locus from different cell populations were prepared in Affinity Designer.

Human Lung Tissue.

Excised sub-transplant-quality human lung tissues from donors without pre-existing chronic lung diseases and explanted fibrotic human lungs were procured through the BioRepository and Precision Pathology Center at Duke University in accordance with institutional procedures (Duke University Pro00082379-'Human Lung Stem Cells'; exempt research as described in 45 CFR 46.102(f), 21 CFR 56.102(e) and 21 CFR 812.3(p), which satisfies the Privacy Rule as described in 45CFR164.514). Samples of the IPF tissue used for scRNA-seq were obtained from lungs removed at the time of lung transplantation at two lung transplant centres (VUMC and NTI). Non-fibrotic control tissue samples were obtained from lungs declined for organ donation. For IPF lungs, diagnoses were determined according to ATS/ERS consensus criteria. All studies were approved by the local Institutional Review Boards (IRB; Vanderbilt IRB nos 060165 and 171657, and Western IRB no. 20181836). The diagnosis of IPF was evaluated by a surgical pathology team. The specimens were washed thoroughly in PBS before inflation and immersion in 4% paraformaldehyde at 4° C. overnight. The specimens were subsequently washed in PBS until the appearance of blood was minimal, followed by incubation in 30% sucrose at 4° C. The samples were then incubated with OCT compound at a 1:1 ratio for 1 h at 4° C. before embedding in OCT. Section with a thickness of 7-9 m were used for histological analysis.

Immunostaining.

Lungs and alveolar organoids were prepared as described previously. Briefly, the tissues were fixed with 4% paraformaldehyde at 4° C. for 4 h (for lungs) or at room temperature for 30 min (for organoids), and then embedded in OCT compound or paraffin. Sectioned samples (10 m) were utilized for staining following incubation at 95° C. for 10-15 min for antigen retrieval using 10 mM sodium citrate. Primary antibodies were as follows: pro-surfactant protein C (Millipore, ab3786, 1:500), AGER (R&D Systems, MAB1179, 1:250), KRT8 (DSHB, TROMA-I, 1:50), KRT17 (NSJ, V2176, 1:250), KRT19 (DSHB, TROMA-III, 1:50), tdTomato (ORIGENE, AB8181-200, 1:500), CLDN4 (Invitrogen, 36-4800, 1:200; Proteintech, 16165-1-AR, 1:500), GFP (Novus Biologicals, NB100-1770, 1:500), LGALS3 (Cedarlane, CL8942AP, 1:500), SOX4 (Invitrogen, MA5-31424, 1:250), SFN (Invitrogen, PA5-95056, 1:250; Proteintech, 66251-1-Ig, 1:500; Abcam, ab77187, 1:200), ACTA2 (Sigma, C6198, 1:500), γ-H2AX (R&D, 4418-APC, 1:500; Novus Biologicals, NB100-74435, 1:250), CDKN1A (Sigma, ZRB1141, 1:200; BD Biosciences, 556430, 1:200), COL1A1 (Proteintech, 67288-Ig, 1:1,000), YAP (Cell Signaling Technology, 4912S, 1:250).

X-Gal and Haematoxylin-and-Eosin Staining.

Paraformaldehyde-fixed frozen sections were incubated overnight with X-gal staining buffer containing 1 mg ml-1 X-gal (Thermo, R0941), 5 mM K3Fe(CN)6, 5 mM K4Fe (CN)6, 2 mM MgCl2, 0.01% sodium deocycholate and 0.02% NP-40 at 37° C. The sections were washed three times in PBS and mounted. For haematoxylin-and-eosin staining, 10-μm paraffin sections were submerged in Histoclear and a series of ethanol. Mayer's haematoxylin was used to stain the nuclei, followed by staining using 1% eosin Y.

Proximity Ligation In Situ Hybridization.

Proximity ligation in situ hybridization was performed as described previously69. Briefly, frozen mouse lung sections were fixed with 4.0% paraformaldehyde for 20 min, treated with 20 μg ml-1 proteinase K for 9 min at 37° C. and dehydrated with an up-series of ethanol. The sections were incubated with gene-specific oligos in hybridization buffer (1 M sodium trichloroacetate, 50 mM Tris pH 7.4, 5 mM EDTA and 0.2 mg ml-1 heparin) for 2 h at 37° C. Common-bridge and circle probes were added to the sections and incubated for 1 h, followed by a T4 DNA ligase reaction for 2 h. Rolling-circle amplification was performed using phi29 polymerase (Lucigen, 30221) for 12 h at 37° C. Fluorophore-conjugated detection probe was applied and incubated for 30 min at 37° C., followed by mounting in medium containing 4,6-diamidino-2-phenylindole (DAPI).

Image Acquisition, Processing and Quantification.

Images were captured using an Olympus FV3000 confocal microscope with a ×20, ×40 or ×60 objective, a Zeiss wide-field fluorescence microscope (X-gal staining) and a Zeiss Axio Imager wide-field fluorescence microscope (haematoxylin and eosin). The cells were manually counted based on immunohistochemistry markers and DAPI. For the determination of the average intersects per linear distance, a mean linear intercept analysis was conducted as previously described over the single-channel immunofluorescence stain of interest11. Images were processed using the Olympus CellSens application or ImageJ and figures were prepared using Affinity Designer.

Statistics and Reproducibility.

Experiments were performed on at least three biological replicates (except organoid scRNA-seq and ChIP-seq). The sample size was not pre-determined. Data are presented as the mean with the s.e.m. to indicate the variation within each experiment. Statistical analyses were performed in GraphPad Prism. Two-tailed and unpaired Student's t-tests were used for comparisons between two experimental conditions. The Mann-Whitney one-tailed test was used for comparisons between two conditions that showed non-normal distributions.

Figure 1B:
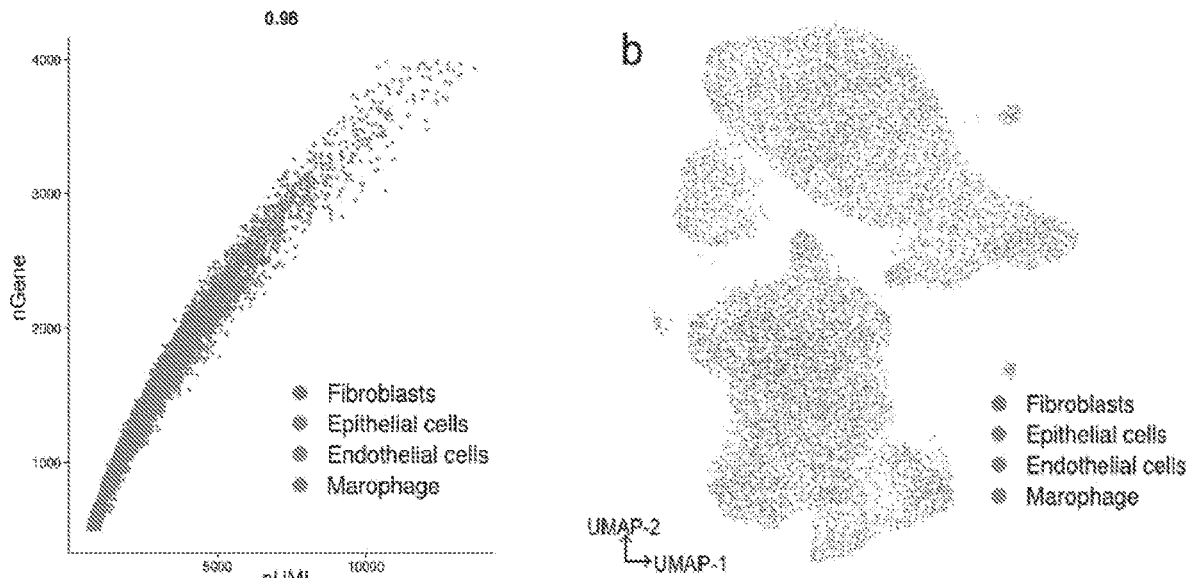
Figure 1C:
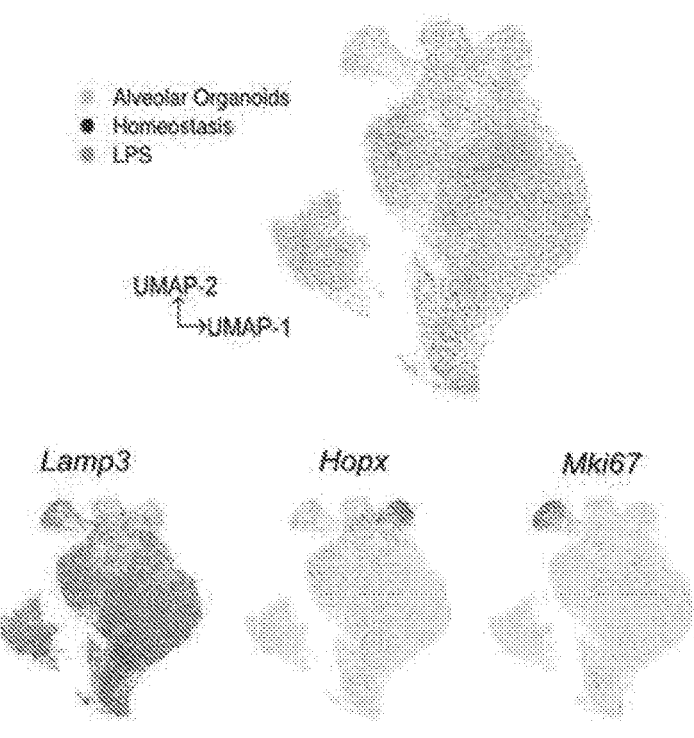

Example 1: Single-Cell Transcriptomics Reveals Previously Unknown Alveolar Epithelial Cell States in Ex Vivo Organoids Recent studies have shown that AEC2s proliferate and give rise to AEC1s in response to lung injury. Moreover, AEC2s spontaneously generate AEC1s in alveolar organoids. However, the molecular mechanisms and transitional cell states underlying the differentiation of AEC2 into AEC1 are poorly understood. To address these questions, we purified AEC2s and PDGFRα+ fibroblasts to set up alveolar organoids. Single-cell transcriptome analysis was performed on cells isolated from the day-10 organoid culture (FIG. 1A). Uniform manifold approximation and projection (UMAP) identified two major clusters, consisting of Epcam+ epithelial cells and Vim+Pdgfra+ fibroblasts (FIG. 1B). Next, we further deconvoluted and visualized epithelial cell populations and compared them with a publicly available single-cell RNA sequencing (scRNA-seq) dataset of lipopolysaccharide (LPS)-injured alveolar epithelial cells14. Organoid-derived epithelial cells overlapped with their in vivo counterparts, revealing transcriptional and cell-state similarities (FIG. 1C). We observed multiple sub-clusters among the organoid-derived epithelial cells: cells expressing Sftpc (a marker for AEC2), cells expressing Ager (a marker for AEC1) and Sftpc+Mki67+ proliferating AEC2s (FIG. 1D).

Figure 1D:
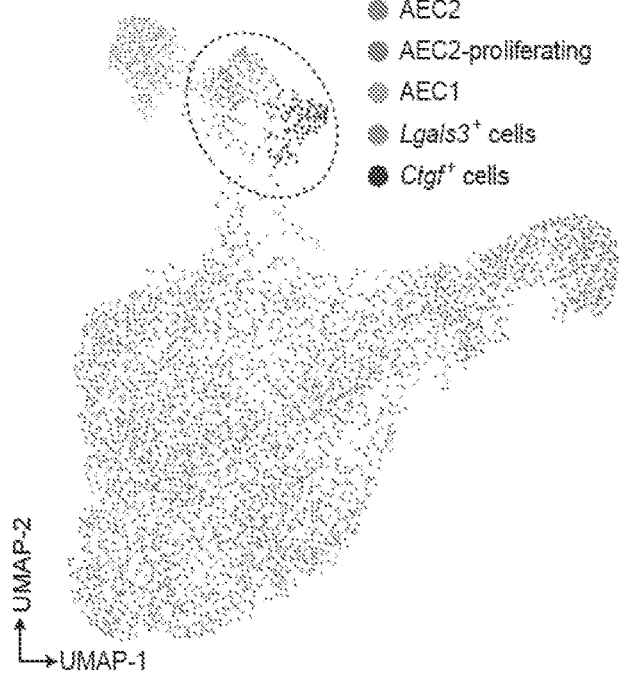
Figure 1E:
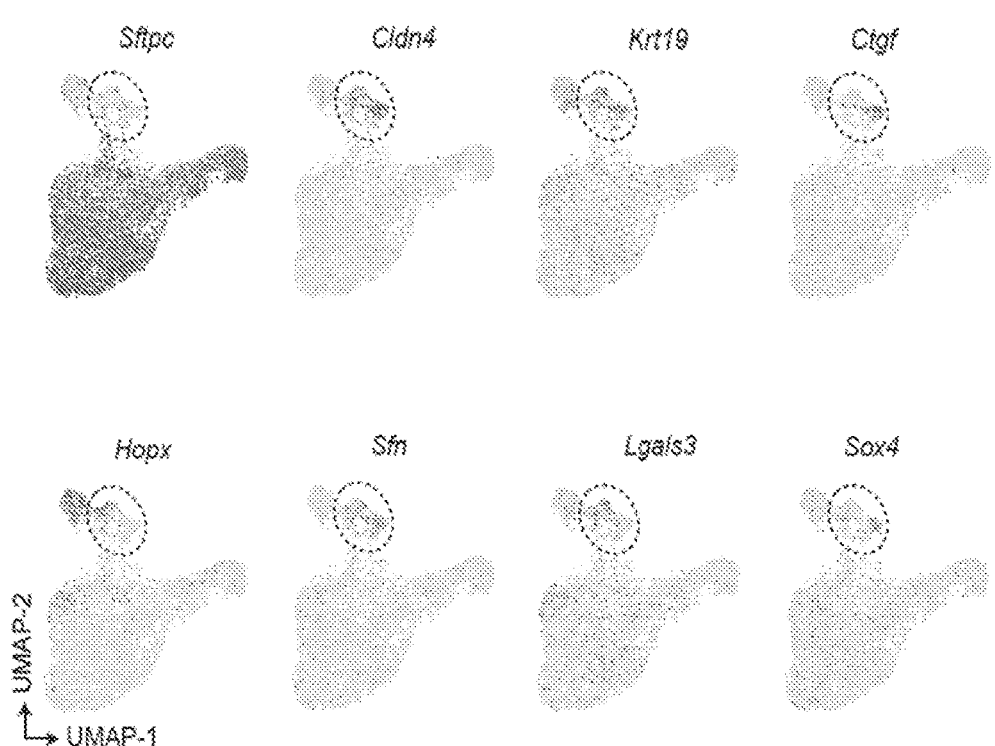
Figure 1F:
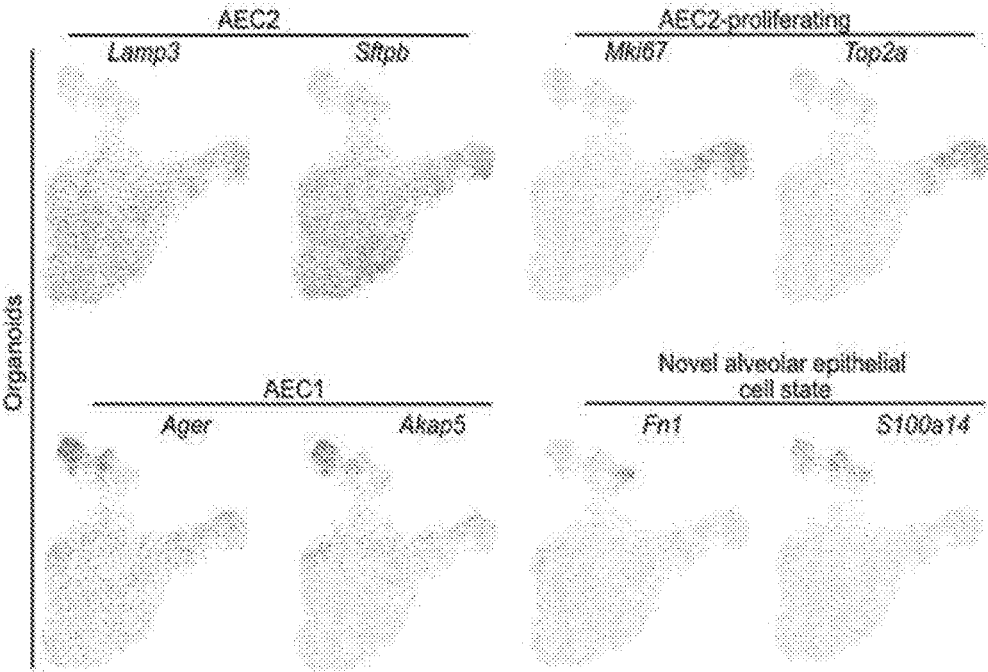
Figure 1G:
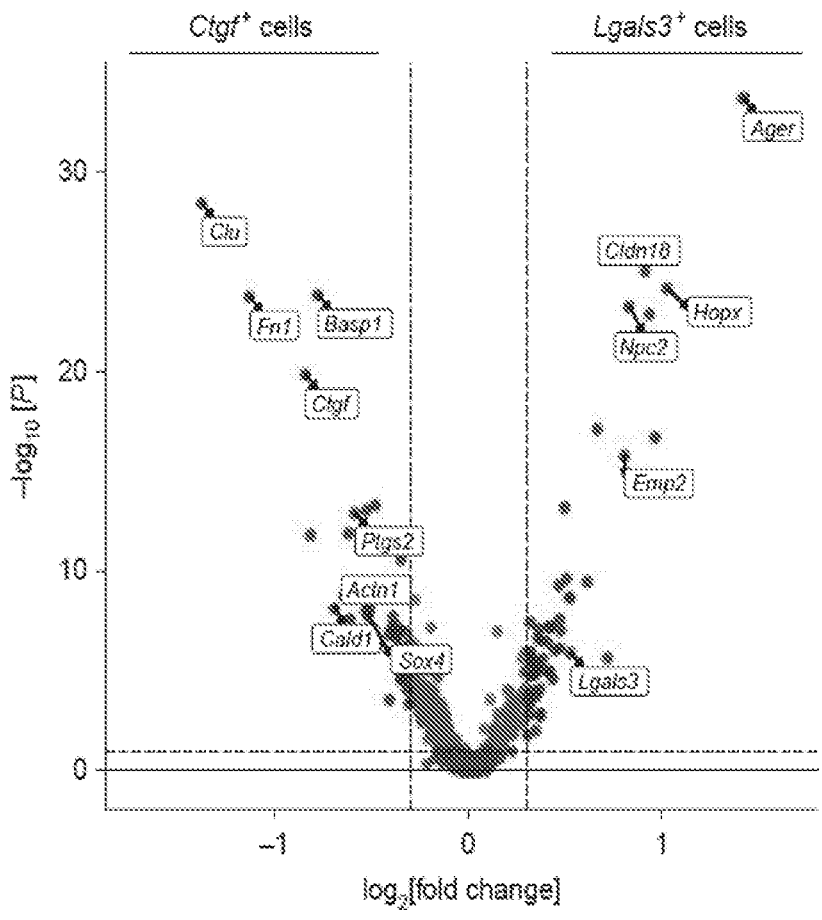
Figure 1H:
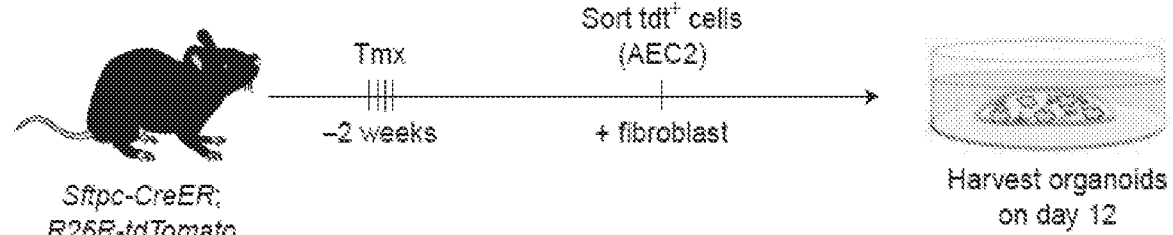
Figure 11A:
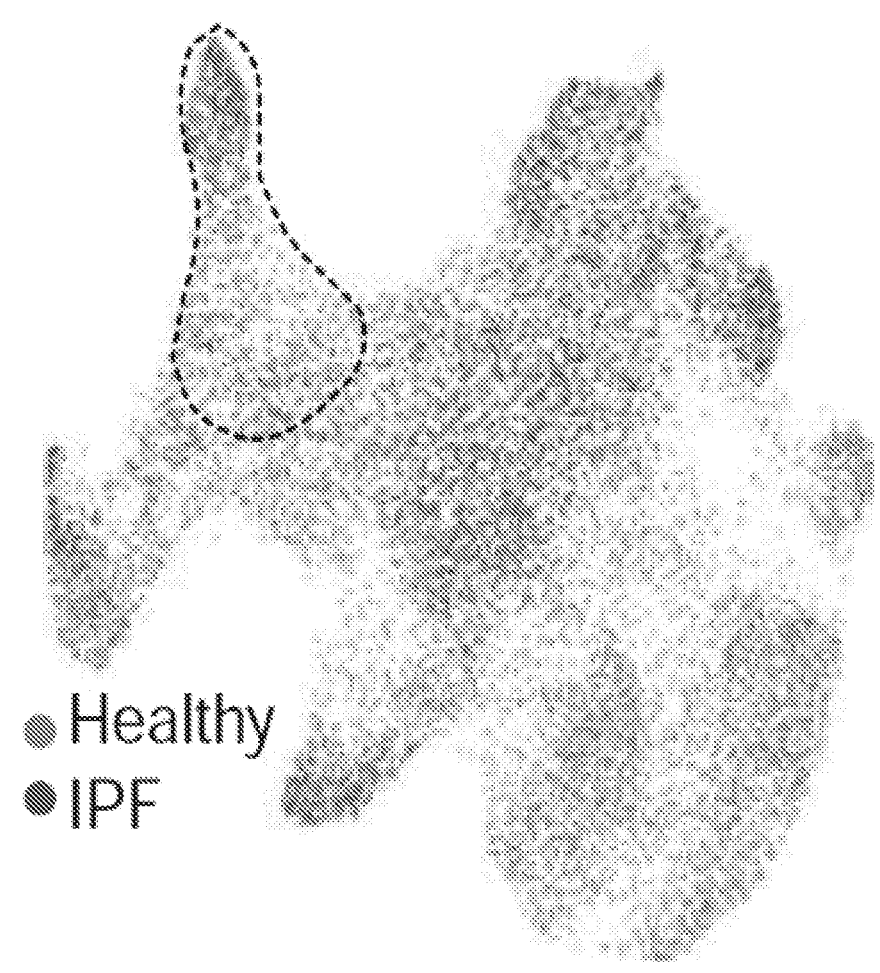
FIGS. 11A-11M show enrichment of PATS-like states in IPF suggests persistence of this state in pathological milieu.
Figure 11B:
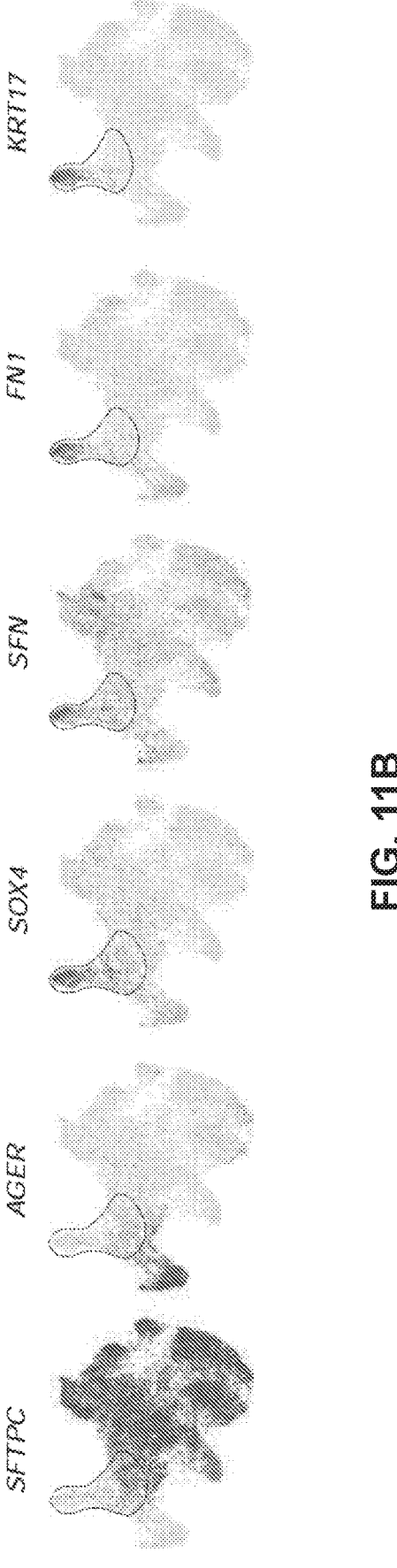
Figure 11C:
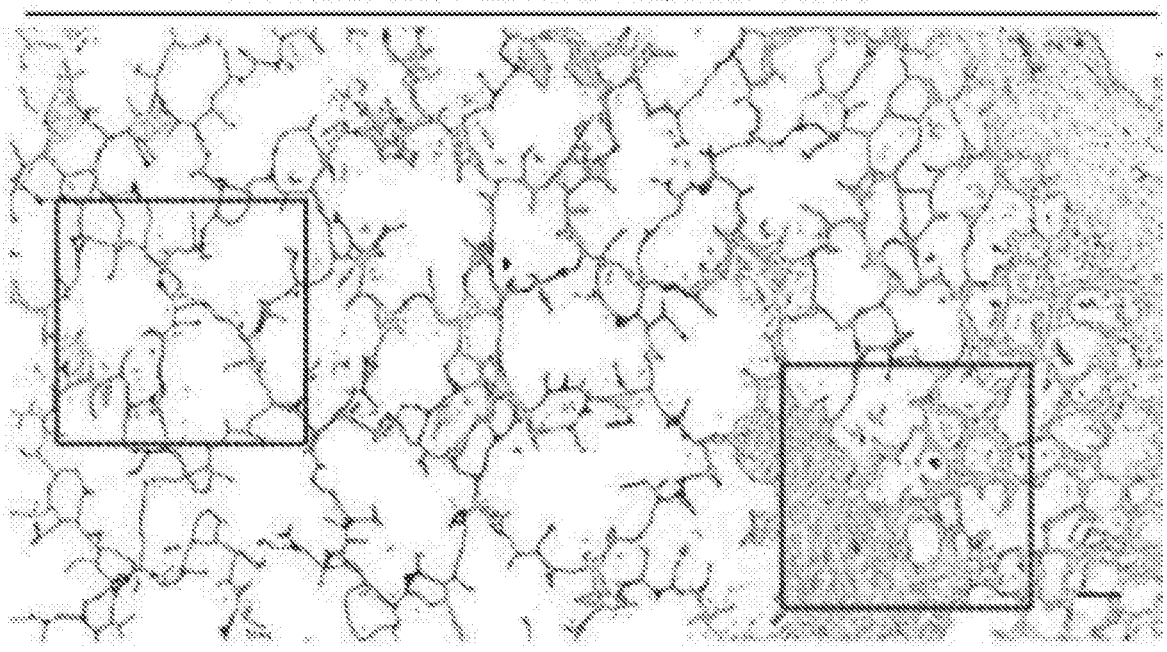
Figure 11D:
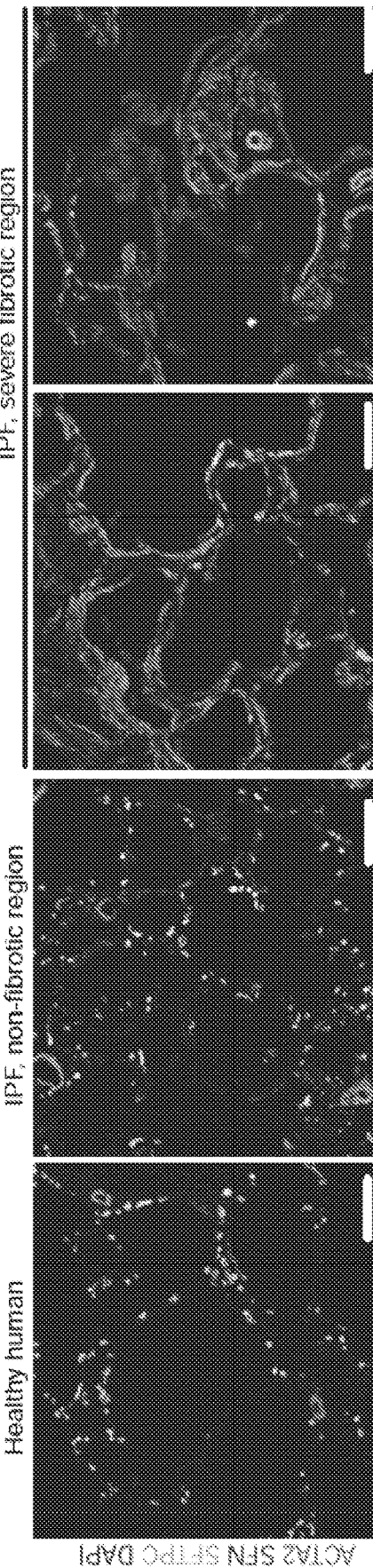
Figure 11E:
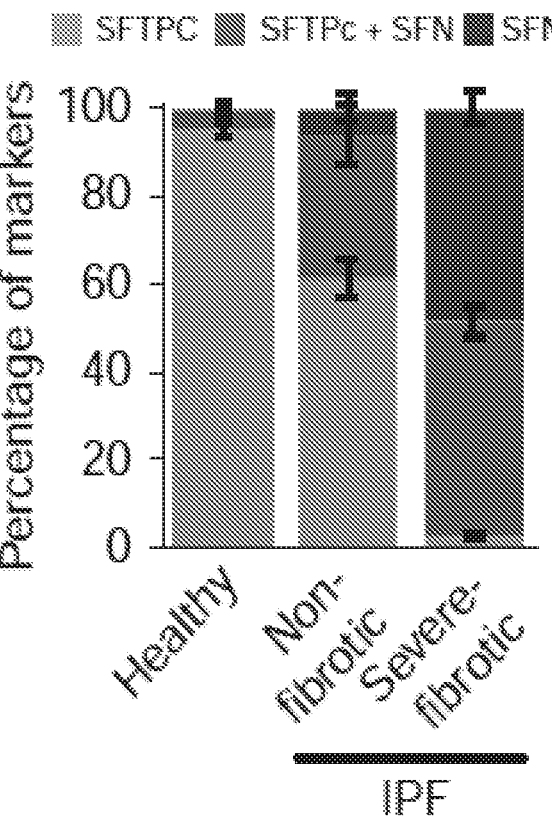
Figure 11F:
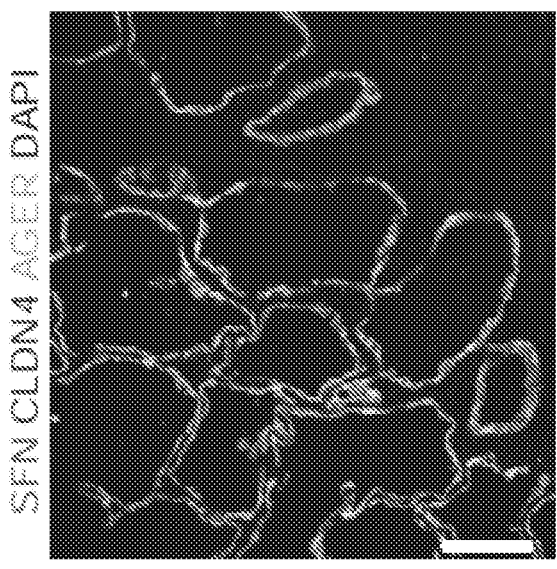
Figure 11G:
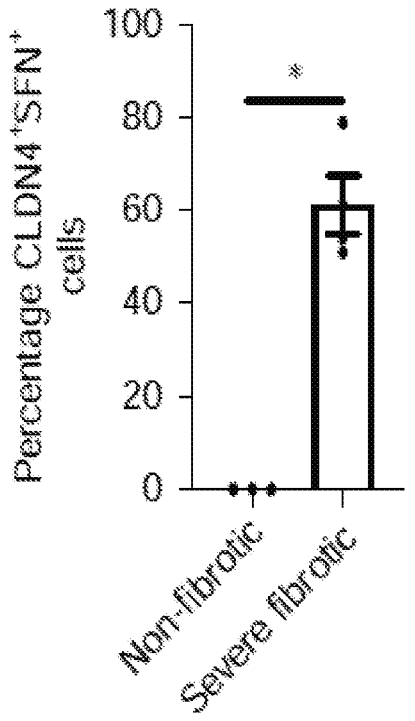
Figure 11H:
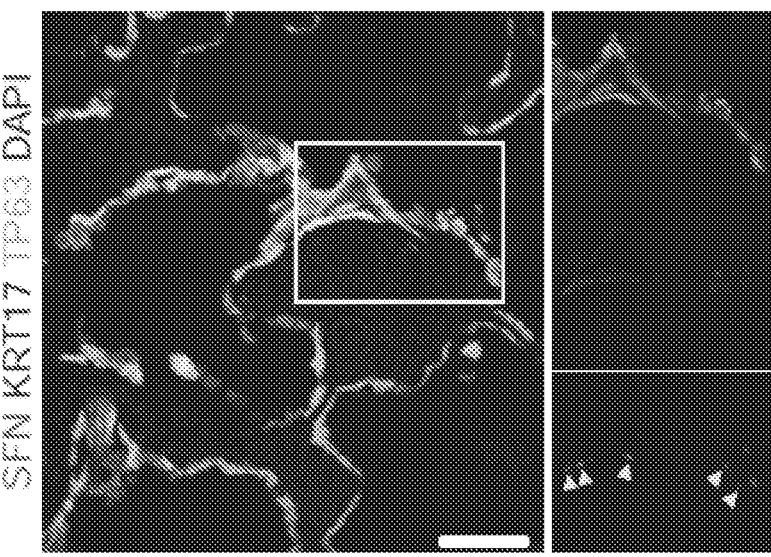
Figure 11I:
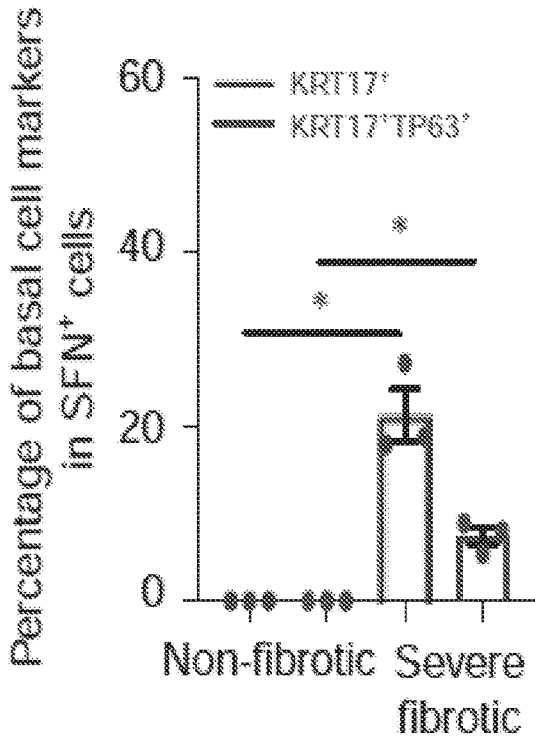

In addition, we identified a population of alveolar epithelial cells expressing Cldn4, Krt19 and Sfn (FIG. 1D, FIG. 1E, and FIG. 1F). The marker genes unique to this cluster showed two distinct patterns when visualized in UMAP and volcano plots (FIG. 1b-d). One subset (Ctgf+ cells) was enriched for Ctgf, Clu, Sox4 and Actn1, whereas the other (Lgals3+ cells) was enriched for Lgals3, Csrp1, S100a14 and Cldn18. Additional transcripts enriched in the Lgals3+ sub-cluster including Ager, Emp2 and Hopx (markers of AEC1s) suggest resemblances and a potential lineage hierarchy between Lgals3+ cells and AEC1s (FIG. 1G). These data suggest that the Cldn4+Krt19+Sfn+ population is an intermediate between AEC2 and AEC1. This population was termed "pre-alveolar type-1 transitional cell state" (PATS). We performed immunofluorescence for PATS markers on alveolar organoids to validate the single-cell data (FIG. 11I). Images were representative of 30 organoids from three mice. This confirmed the presence of cells expressing CLDN4, LGALS3 and SOX4 in alveolospheres. Together, these data identified unique cell states during alveolar epithelial stem cell differentiation in organoid cultures.

Example 2: PATS Cells Emerge In Vivo after Alveolar Injury

It was then investigated whether PATS cells can be observed in vivo in homeostatic and regenerating alveolar tissues. To test this, we rendered scRNA-seq data from LPS-treated and control mouse lungs in UMAP plots and found a population that is unique to LPS injury. UMAP plots showed the expression of genes in AEC2 (Lamp and Sftpb), AEC2-proliferating (Mki67 and Top2a), AEC1 (Ager and Akap5), and novel alveolar epithelial cell state in an alveolar organoid scRNA-seq dataset (4,573 cells) and LPS treated or control lungs (13,204 cells). Importantly, this population is enriched for genes expressed in PATS, including Cldn4, Sox4, Lgals3, S100a14, and Fn1.

Figure 2:
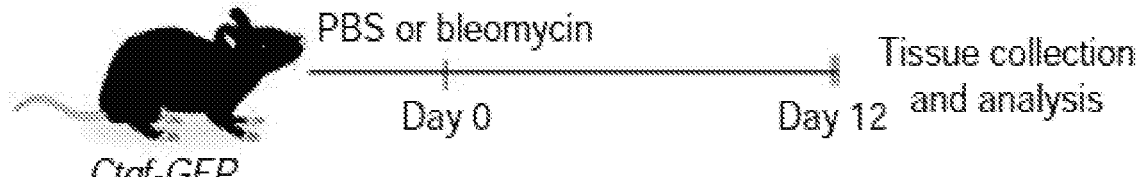
FIG. 2 is a schematic showing the experimental workflow of bleomycin-induced lung injury in Ctgf-GFP mice.

To further characterize PATS, a Ctgf-greenfluorescent protein (GFP) transgenic mouse line was utilized (Hall-Glennet al., 2012, PLoS ONE 7:e30562). Mice were exposed to to bleomycin, a drug that causes transient fibrosis, and collected the lungs of the mice on day 12 post injury (FIG. 2). Immunofluorescence for GFP in uninjured Ctgf-GFP mice revealed GFP signal specifically in fibroblasts and not in alveolar epithelial cells. In contrast, in bleomycin-injured lungs, GFP expression was found in epithelial cells co-labeled with PATS markers including CLDN4, LGALS3 and SFN. A small fraction of GFP+ cells co-expressing low levels of AEC2 marker was observed, probably due to perdurance of SFTPC protein as AEC2s transition to the PATS.

Figure 3:
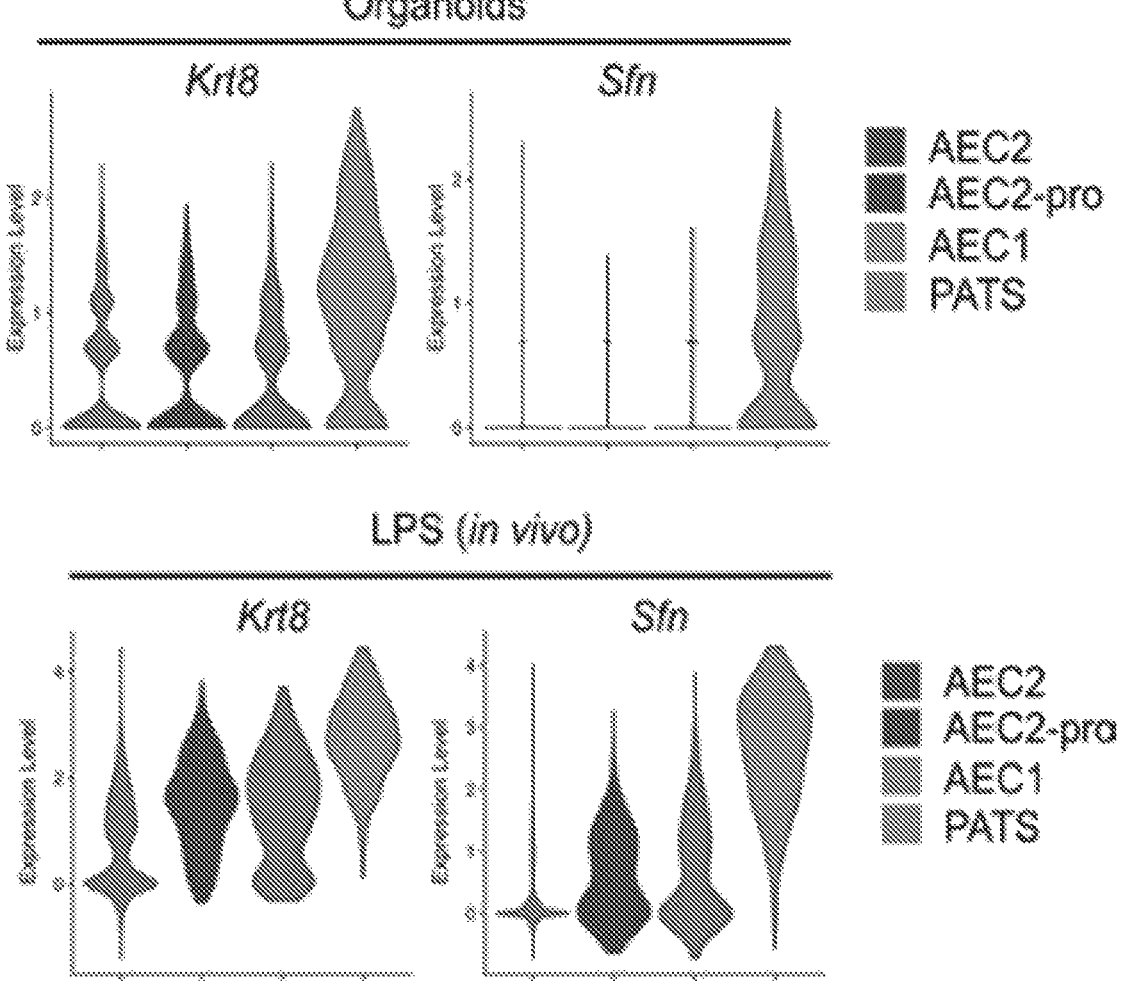
FIG. 3 are violin plots show the expression of Krt8 and Sfn in epithelial cell populations derived from alveolar organoid (top, n=4,573 cells) and LPS-injured lung scRNA-seq datasets (bottom, n=13,204 cells). Violin plots indicate distribution of the cells.

The expression of KRT8 in bleomycin-injured lungs was tested. A significant increase in overlap between KRT8- and Ctgf-GFP-expressing cells was found by immunostaining for Ctgf-GFP, KRT8, and SFTPC in control lung and bleomycin treated lungs on day-12. These data further corroborate with elevated levels of Krt8 expression in the scRNA-seq data from organoids and LPS injury (FIG. 3). Together, these data reveal that PATS cells emerge in alveoli after bleomycin injury in vivo.

Figure 4A:
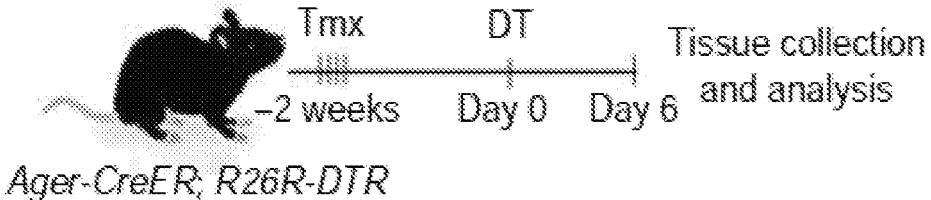
FIGS. 4A-4B shows that PATS cells emerge transiently from alveolar stem cells after lung injury in vivo.
Figure 4B:
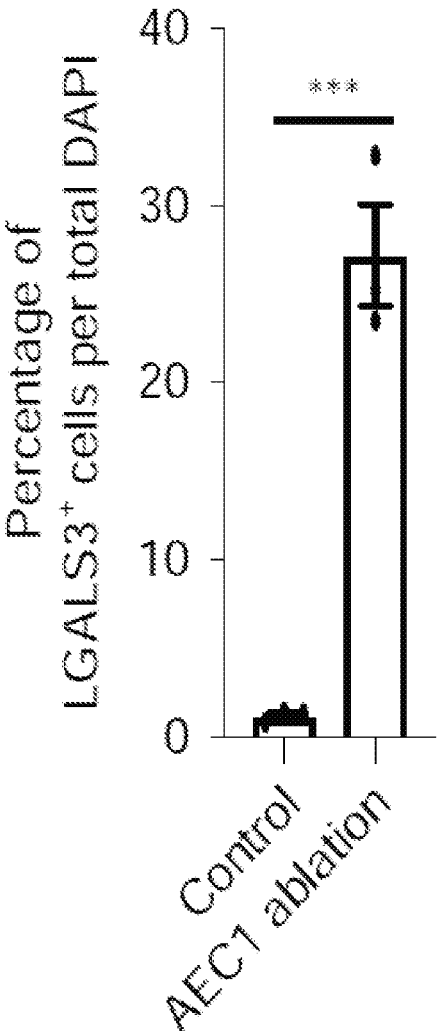

It was then tested whether PATS cells are specific to bleomycin injury or appear in other injury models. To test this, Ager-CreER; R26R-DTR mice were administered tamoxifen, followed by diphtheria toxin (DT), which resulted in selective ablation of AEC1s. We collected samples on days 6 and 28 after DT injection and performed immunostaining (FIG. 4A). Interestingly, cells expressing CLDN4, SFN, KRT19 and LGALS3 with elongated morphology in AEC1-ablated lungs on day 6 but not in the controls was observed (FIG. 4B). Low levels of SFTPC expression in the elongated cells that co-expressed PATS markers was also observed by immunostaining, probably due to perdurance of SFTPC during the transition of AEC2 to PATS. Note no PATS markers were observed by immunostaining in AEC1-ablated lungs on day 28, suggesting that PATS cells had matured into fully differentiated AEC1s. These data suggest that the emergence of the PATS is a general mechanism in alveolar regeneration.

Example 3: Lineage Tracing Reveals that PATS Cells Originate from AEC2s

Figure 5A:
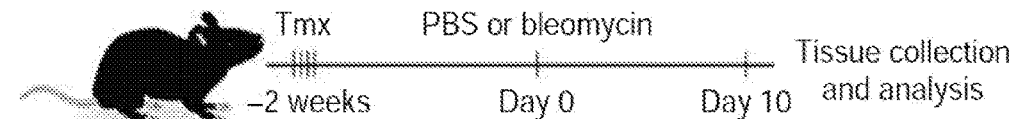
Figure 5B:
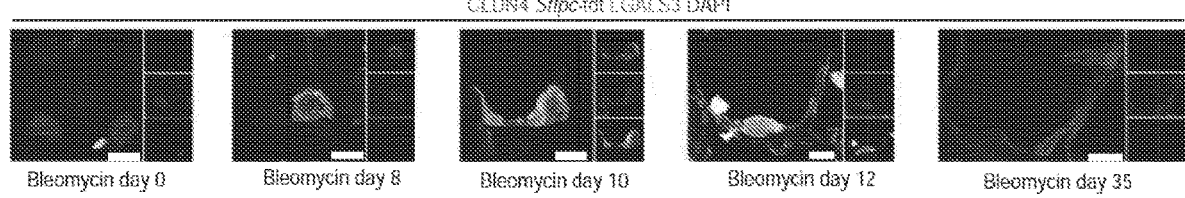
Figure 5C:
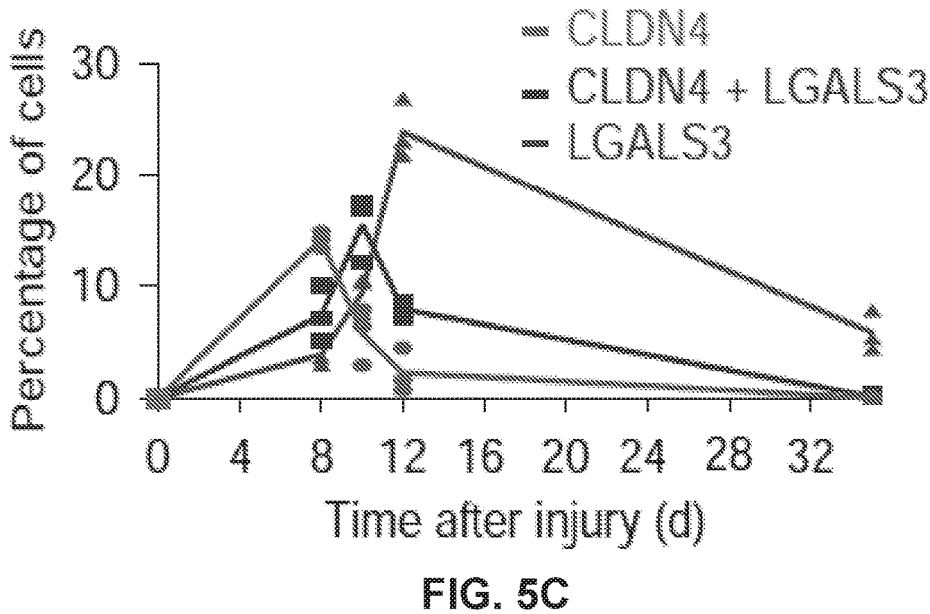
Figure 5D:
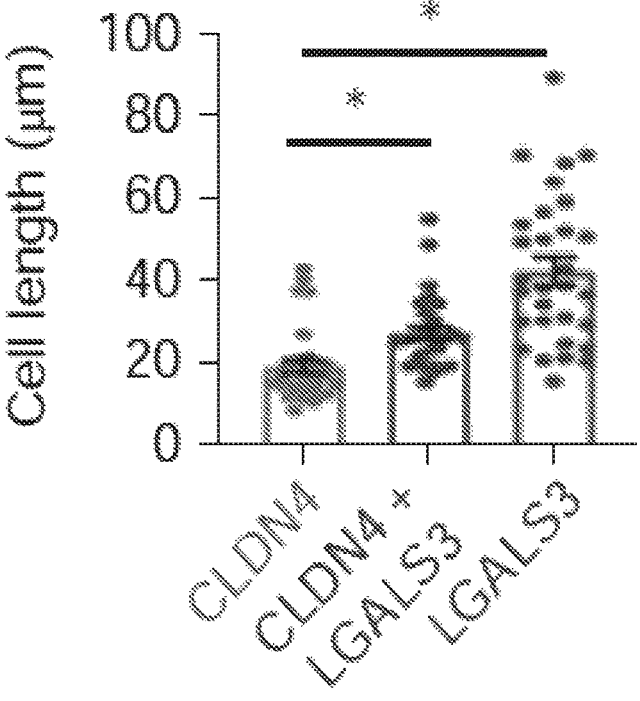
Figure 5E:
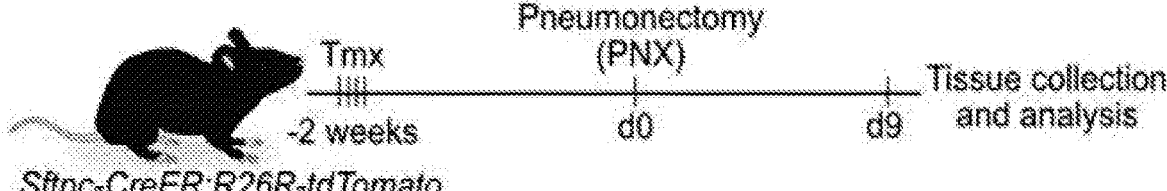

The data presented earlier from organoids and injury models suggested that PATS cells originate from AEC2s. To empirically test this hypothesis, we used a Sftpc-CreER; R26R-tdTomato (hereafter referred to as Sftpc-tdT+) mouse model, in which the administration of tamoxifen permanently induces tdTomato expression specifically in AEC2s and their descendants (FIG. 5A). On day 10 post bleomycin administration, lineage-labeled (tdTomato+, tdt+) cells co-expressing LGALS3, SFN and CLDN4 in damaged alveolar regions but not in control lungs was observed. Tdt+ cells co-expressing AGER displayed a flat, thin and elongated morphology at the later times, confirming that AEC2s transition to AEC1s. Interestingly, lineage-labeled cells co-expressing PATS markers-including SFN, CLDN4 and LGALS3-had distinct morphological features (rounded, 'stretched' and elongated) during the repair process (FIG. 5B). To quantify this, we scored the lineage-positive cells according CLDN4+ and/or LGALS3+ expression as well as their shape (FIG. 5C). Three distinct patterns of marker expression was observed, CLDN4+, CLDN4+LGALS3+ and LGALS3+, and found that these correlated with round, stretched and elongated morphologies, respectively (FIG. 5C and FIG. 5D). Moreover, we observed a substantial enrichment of CLDN4+ cells on day 8, CLDN4+LGALS3+ on day 10 and LGALS3+ on day 12 following bleomycin-induced injury (FIG. 2I). It was noticed CLDN4+ and CLDN4+LGALS3+ cell states in the scRNA-seq dataset but not a distinct LGALS3+ population. Similar PATS marker expression was detected in AEC2-lineage-labelled mice during pneumonectomy-induced 'physiological' regeneration (FIG. 5E). The discrepancy between the expression of LGALS3 in scRNA-seq versus immunostaining can be due to perdurance of LGALS3 protein in the terminal AEC1.

Together, this analysis revealed that the differentiation of AEC2 into AEC1 goes through two distinct states (FIG. 5F).

Example 4: Lineage-Tracing Analysis Reveals PATS Cells Generate AEC1s

Figure 6C:
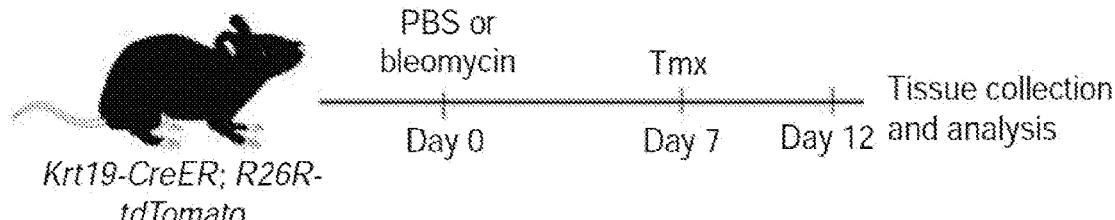

Multiple lines of data from the experiments presented earlier suggest that PATS cells are en route to AEC1. To test this, an algorithm tool called Velocyto18 was used, which allows the prediction of cell differentiation trajectories based on the ratios between spliced and unspliced messenger RNA. Strong RNA velocities (trajectory) originating from the PATS1 Ctgf+ population to AEC1 through the PATS2 Lgals3+ population was observed (FIG. 6A and FIG. 6B). A CreER allele of Krt19, a gene enriched in PATS, combined with R26R-tdTomato (Krt19-tdt) was then used to carry out lineage tracing after bleomycin injury to test whether the same trajectory occurs in regenerating alveoli in vivo. First, mice were injured with bleomycin and tamoxifen was administered 7 d later to label Krt19-expressing cells and their progeny (FIG. 6C). Immunofluorescence for AEC2, AEC1 and PATS markers was then performed.

Figure 6D:
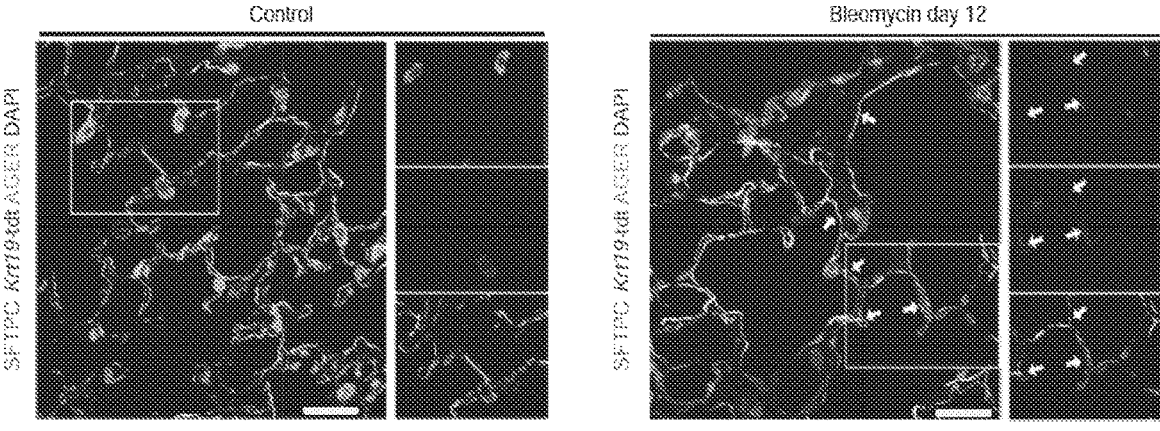
Figure 6E:
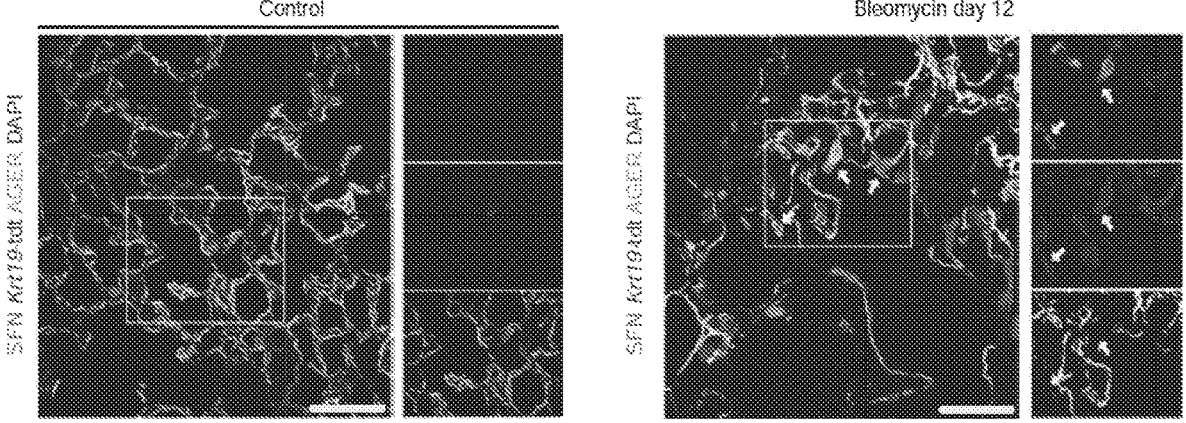
Figures 6F, 6G:
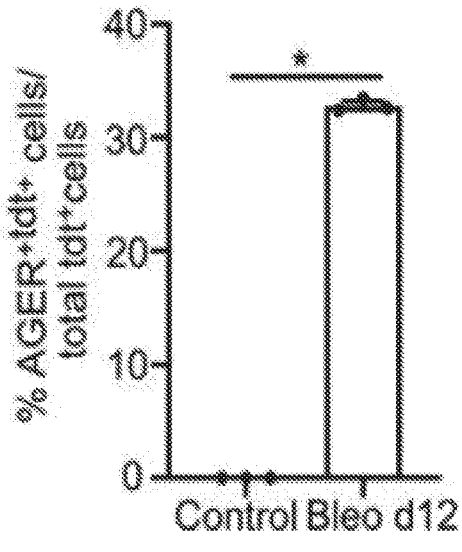
Figure 6H:
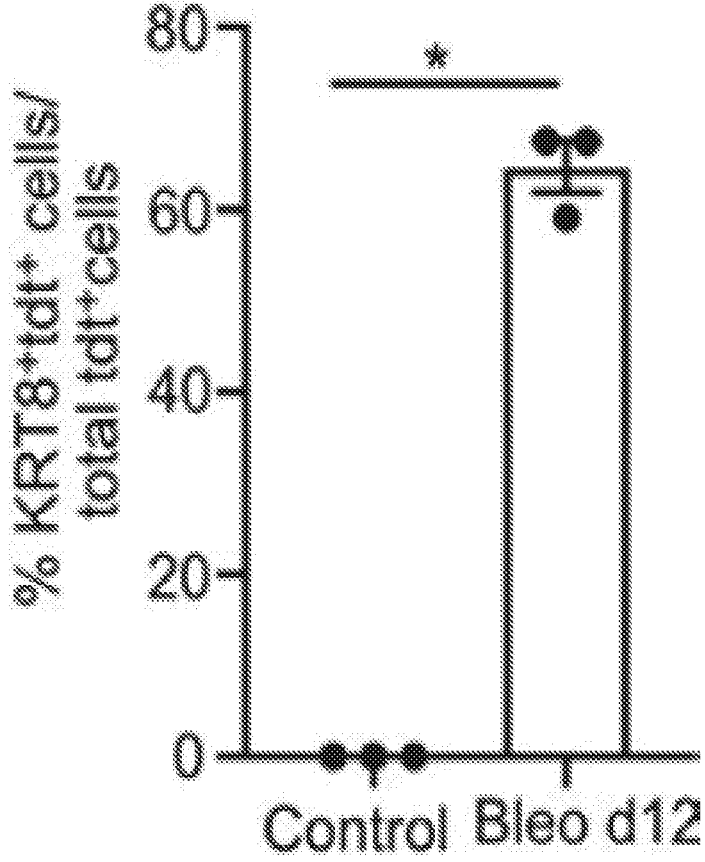

Numerous Krt19-tdt+ cells co-expressing AGER, a marker for AEC1, were found on day 12 post bleomycin administration (FIG. 6D, FIG. 6E, FIG. 6F). In uninjured lungs, we observed tdt expression in some LGALS3+ macrophages and rarely in AEC1s (FIG. 6G). We did not find Krt19-tdt+ cells co-expressing SFTPC in uninjured regions of bleomycin-treated mice, indicating that Krt19 expression is specifically activated in response to injury in the damaged regions and the conditions we tested are well suited for labelling and tracing PATS. Co-immunostaining revealed stretched tdTomato labelled cells co-expressing PATS markers including SFN, CLDN4 and LGALS3 in bleomycin-treated lungs but not in the controls (FIGS. 6D-6G, and FIG. 6I1). Thus, the combined RNA-velocity and lineage-tracing analyses reveal that the newly identified PATS traverse between AEC2 and AEC1.

Example 5: Conserved Transcriptional Programs and Pathways in PATS

Differentiation of AEC2s to AEC1s is associated with a dramatic change in the cell shape and structure, from cuboidal to flat and thin. Such a transition is typically accompanied by many changes in the expression of signaling and structural proteins. It was therefore thought that these changes occur in PATS cells. To determine whether these changes occur in PATS cells, scRNA-seq data from organoid cultures (4,573 cells) and LPS-induced injury models (13,204 cells) were analyzed. Numerous genes were conserved among PATS cells, including: genes in the TGFβ signaling pathway (Cdkn2b, Mapk3, Myc, Nbl1, Ppp2r1a, Rbx1, Rhoa, Skp1a, Tgfb1, Tgif1 and Thbs1), genes in the p53 signaling pathway (Bax, Casp8, Ccnd1, Ccnd2, Ccng1, Cdk4, Cdkn1a, Cycs, Ei24, Gadd45a, Gadd45b, Sesn3, Sfn, Shisa5, Thbs1 and Trp53), genes involved in cellular senescence (Calm1, Calm2, Capn2, Ccnd1, Ccnd2, Cdk4, Cdkn1a, Cdkn2b, Eif4ebp1, Ets1, Gadd45b, H2-D1, H2-K1, h2-Q4, H2-Q6, H2-Q7, H2-T22, H2-T23, Kras, Map2k2, Mapk13, Mapk3, Myc, Ppid, Ppp1ca, Ppp3ca, Rbbp4, Rheb, Rras, Sqstm1, Slc25a4, Tgfb2, Trp53, Vdac1, Vdac2, Vdac3 and Zfp36l1), tight junction signaling genes (Actb, Actg1, Actn1, Actn4, Actr3, Ccnd1, Cdc42, Cdk4, Cldn3, Cldn4, Cldn7, Cldrn18, cttn, Ezr, F11r, Hspa4, Itgb1, Jun, Msn, Myh9, Myl6, Myl9, Myl12a, Myl12b, Myn12a, Nedd4, Ocln, Ppp2r1a, Rac1, Rap1a, Rhoa, Slc9a3r1, Tuba1a, Tuba1b, Tuba1c and Vasp), and DNA-damage checkpoint genes (Ccnd1, Ccng1, Cdkn1a, Ddx39b, Ier3, Prpf19, Rpl26, Rps27L, Sox4, Syf2 and Trp53).

Figure 7A:
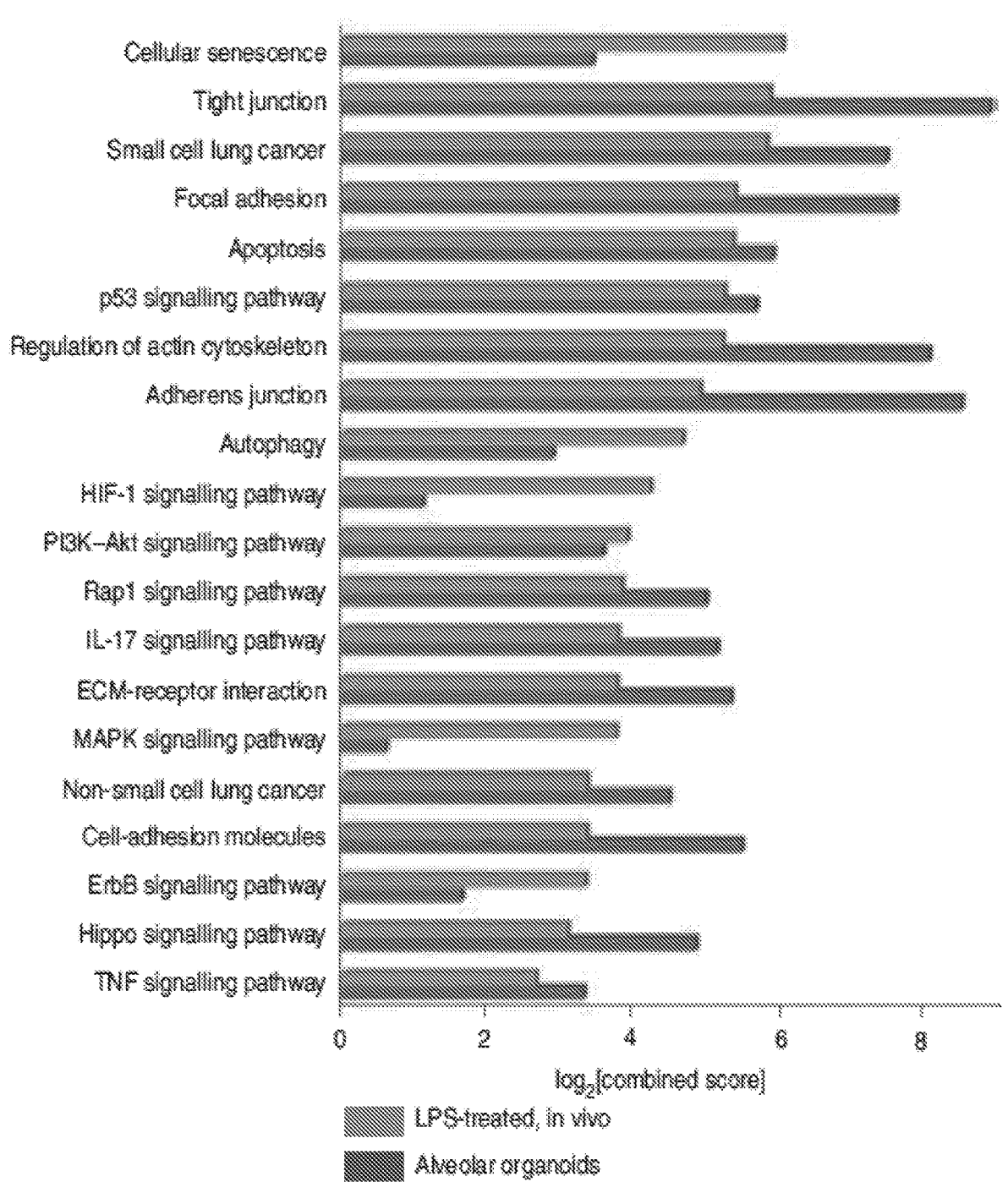
FIGS. 7A-7C show gene-expression signatures and signalling pathways enriched in PATS.
Figure 7B:
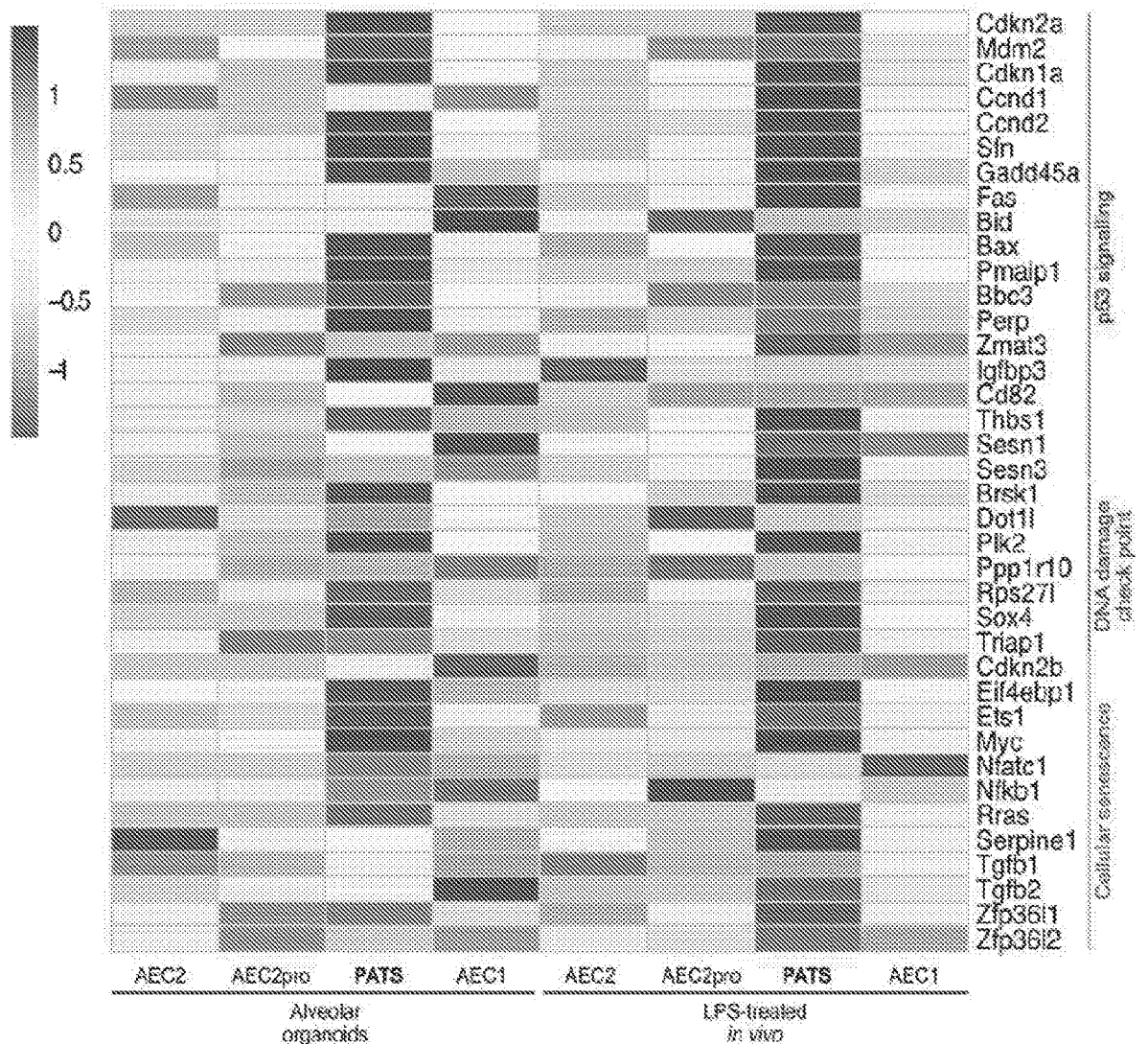
Figure 7C:
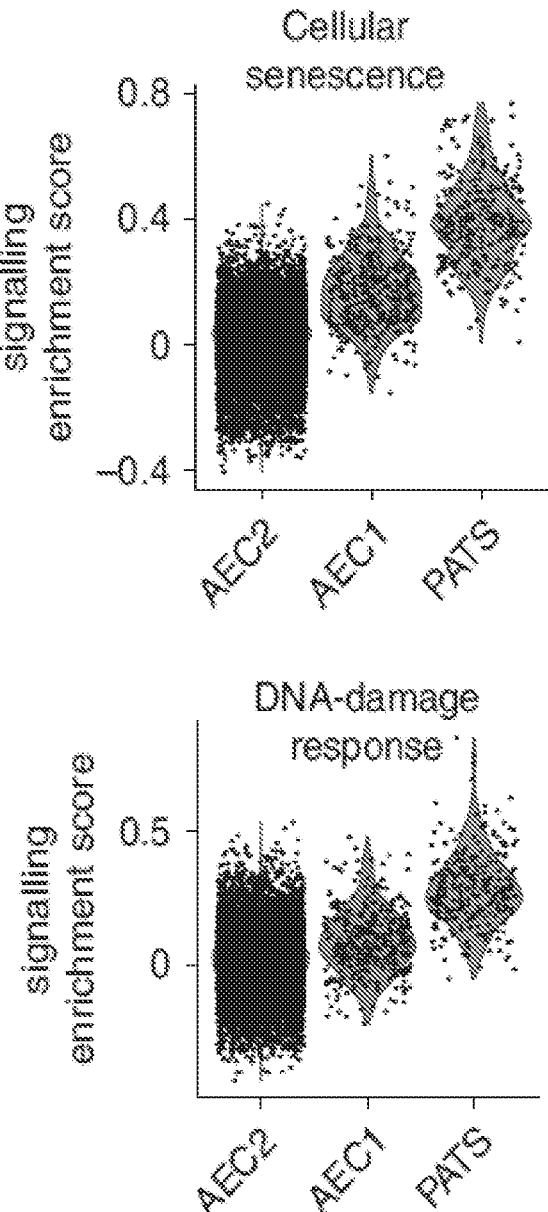

Pathway enrichment analysis revealed that TP53, TNF—NF-κB, ErbB, HIF1, Hippo-YAP, cell-cycle arrest, cytoskeletal dynamics, tight-junction and TGFβ signaling are activated in PATS cells compared with other populations (FIG. 7A and FIG. 7B). Substantial enrichment for genes representative of cellular senescence and DNA-damage-response pathways was unexpectedly found (FIG. 7C and FIG. 7B).

Figure 8A:
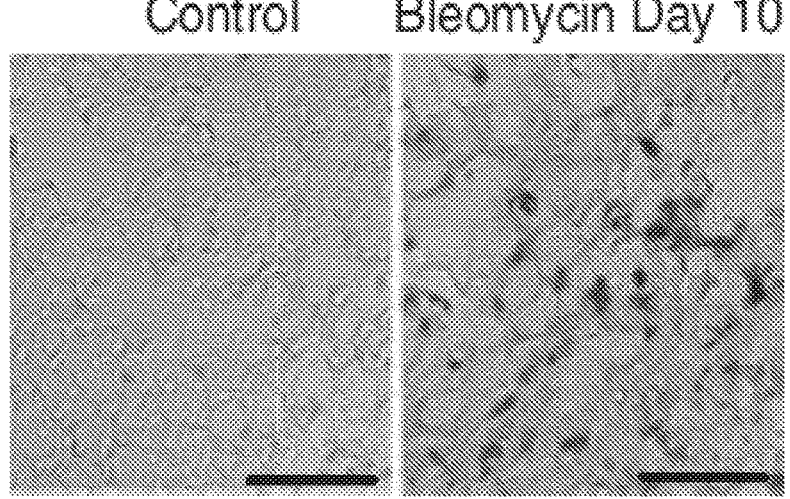
FIGS. 8A-8I shows that PATS cells undergo stretch-induced DNA damage and senescence in vivo and ex vivo.
Figure 8B:
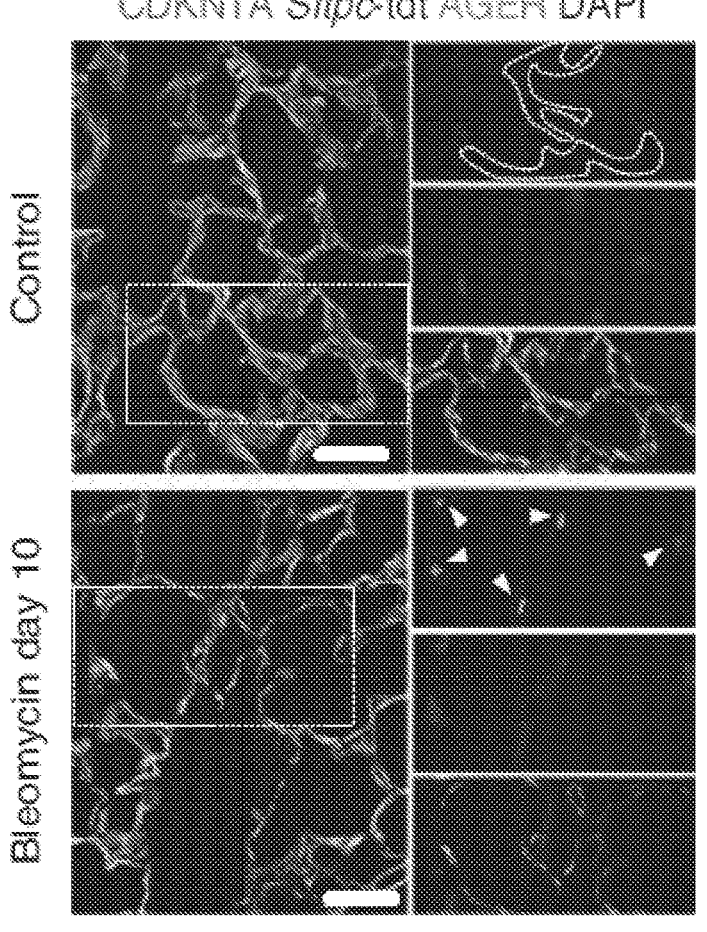
Figure 8C:
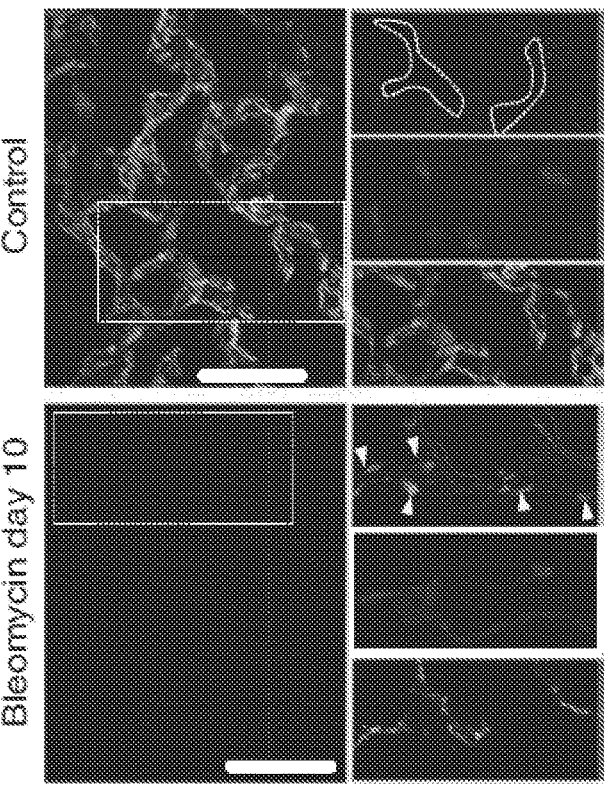
Figure 8D:
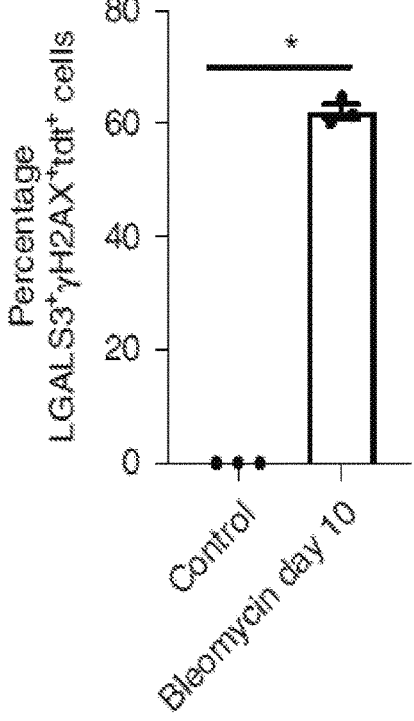

Example 6: PATS Cells Naturally Exhibit DNA Damage and Senescence During Alveolar Regeneration In Vivo These data indicated that DNA-damage- and senescence-associated genes are highly enriched in PATS. To validate these findings, the lungs of bleomycin- and PBS-treated mice were assayed after 10 days for β-galactosidase activity-which serves as a biomarker of senescent cells and λH2AX a marker of DNA damage. Interestingly, numerous β-galactosidase-active cells were detected, based on 5-bromo-4-chloro-3-indolyl-β-d-galactopyranoside (X-gal)-derived blue-colour deposition, in the bleomycin-injured but not control alveoli (FIG. 8A). This was further supported by the expression of the senescence marker CDKN1A (p21), specifically in bleomycin-treated lungs (FIG. 8B). CDKN1A expression was observed in stretched tdt+ cells but not in AGER+ cells, indicating that senescence is not observed in AEC1s (FIG. 8B). Similarly, an accumulation of λH2AX puncta was also detected in the nuclei of stretched Sftpc-tdt+ cells but not in AGER+ cells in bleomycin-treated lungs (FIG. 8C) Further analysis revealed a significant number of λH2AX+Sftpc-tdt+ cells co-expressing LGALS3 in bleomycin-injured lungs but not in controls, indicating that PATS cells undergo DNA damage during alveolar regeneration (FIG. 8D).

Figure 8E:
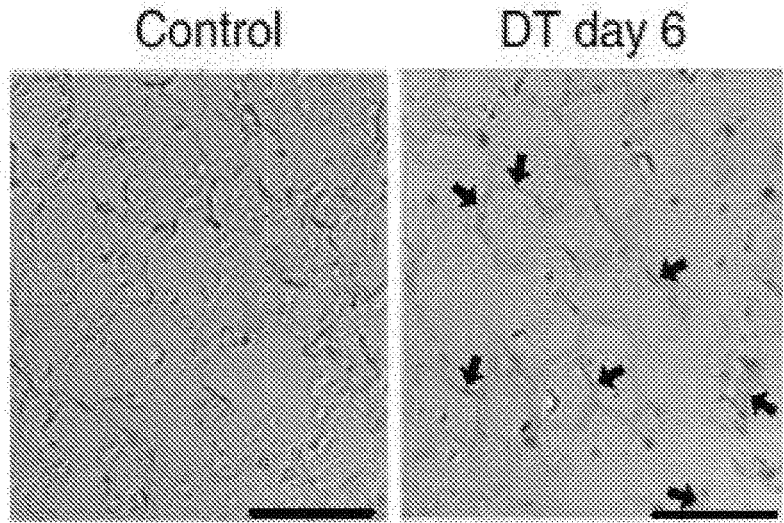
Figure 8F:
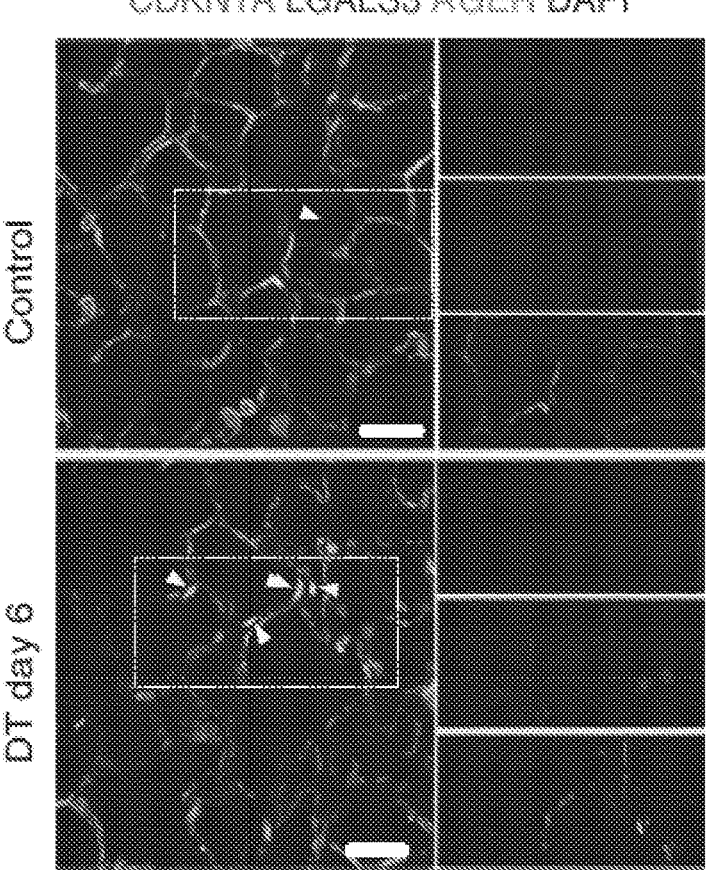
Figure 8G:
Figure 8H:
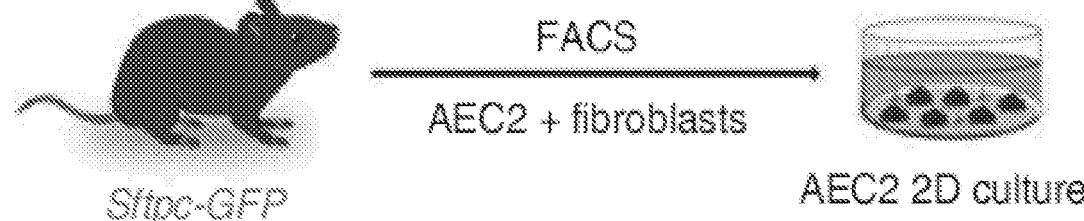

Bleomycin is known to induce DNA damage in cells. However, both scRNA-seq analysis and immunostaining revealed a strong enrichment of DNA-damage-repair signaling in PATS cells. To avoid any potential effects from bleomycin on senescence and DNA damage, marker analysis was performed on lungs from the AEC1-specific ablation model (FIG. 4A). Numerous X-gal+ cells detected and expression of CDKN1A or λH2AX in LGALS3+ cells in AEC1-ablated lungs but not in control alveoli was observed (FIG. 8E, FIG. 8F, and FIG. 8G).

Figure 8I:
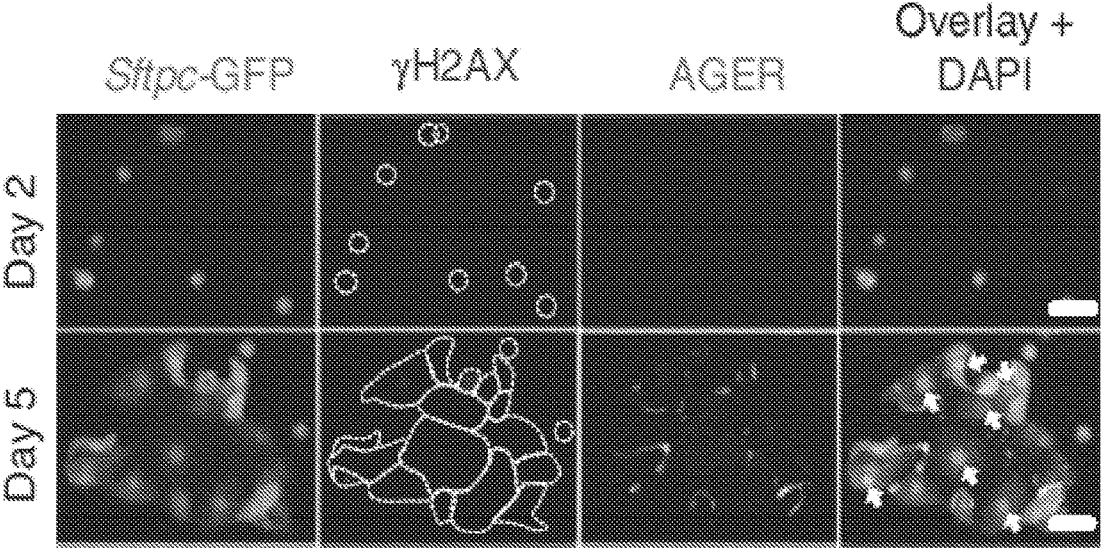

Example 7: PATS Cells are Vulnerable to Mechanical Stretch-Induced DNA Damage Previous studies have shown that ionizing radiation, oxidative stress and the mechanical forces that occur during cell migration and stretching can all cause DNA damage. Pathway analysis revealed an enrichment for genes involved in cytoskeletal changes but not oxidative stress. Given that AEC2 differentiation into AEC1 requires extensive cell spreading and cytoskeletal dynamics it was hypothesized that PATS cells experience mechanical stretching that can lead to DNA damage. To test this, AEC2s were purified from SFTPC-GFP mice and cultured them on a plastic surface (two-dimensional (2D) culture), conditions under which AEC2s spread and differentiate into AEC1s (FIG. 811b). Most of the AEC2s stretched and either lost (GFP-) or downregulated (GFPlo) GFP expression within 5 d following plating. These cells increased their surface area through stretching and began to express AEC1 markers. Interestingly, AGER+ cells were also positive for the DNA-damage marker λH2AX (FIG. 811 and FIG. 8I). Note that no DNA-damage markers were observed in cells on day 2 after plating (FIG. 8I). Together, these data show that cuboidal AEC2s that differentiate into large and thin AEC1s naturally experience DNA-damage repair and undergo transient senescence.

Figure 9A:
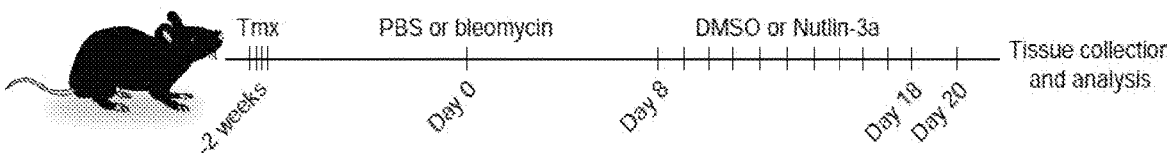
FIGS. 9A-9H show genetic and pharmacological modulation and genomic binding assays reveal transcriptional control of PATS by TP53 signalling.
Figure 9B:
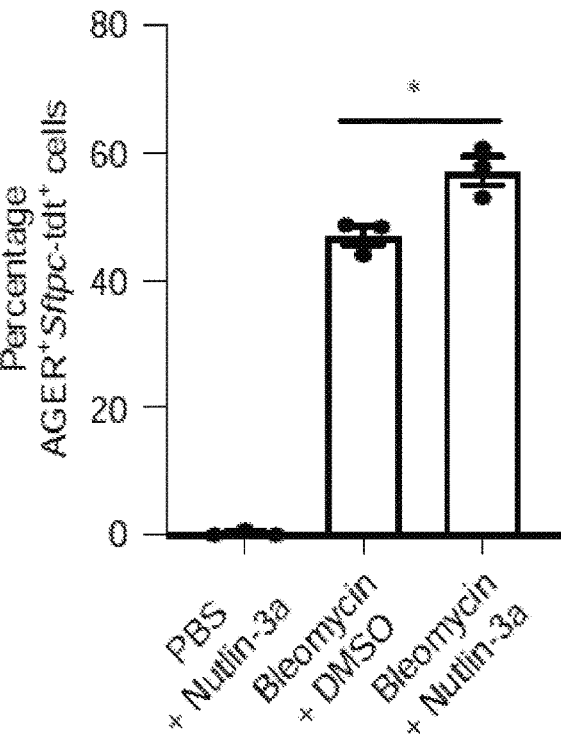
Figure 9C:
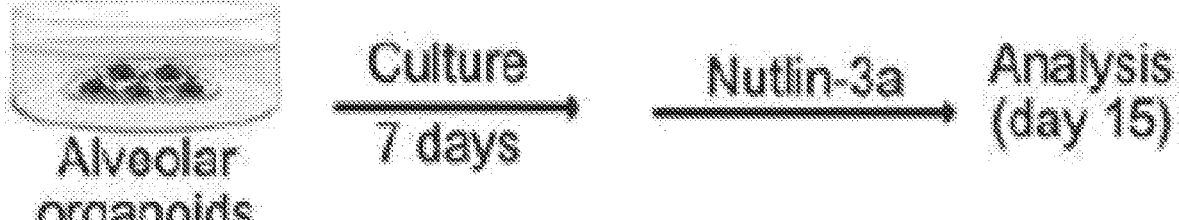
Figure 9D:
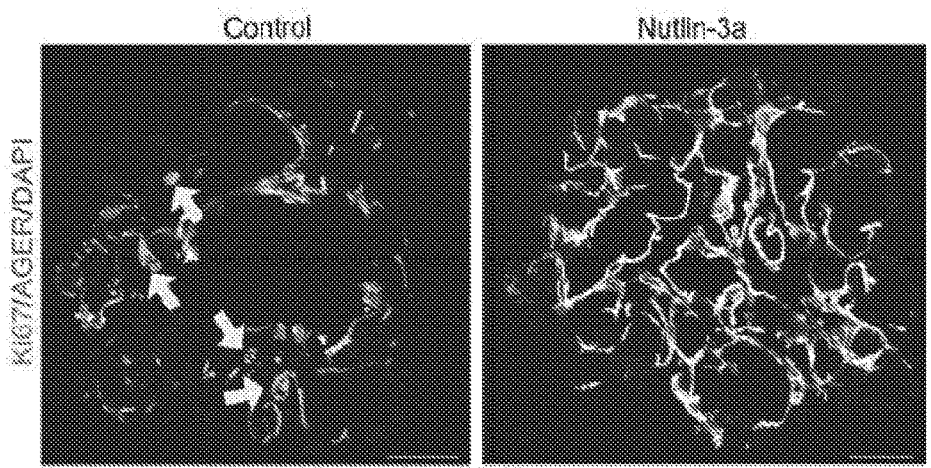

Example 8: Genetic Loss of Function and Pharmacological Activation of TP53 Signaling Dysregulates AEC2 to AEC1 Differentiation Via PATS During Alveolar Injury-Repair These data suggest that activation of TP53 signaling is associated with PATS in injured lungs. Previous studies in other tissues have suggested that TP53 signaling promotes differentiation and suppresses stem cell self-renewal. To determine whether enhanced activation of TP53 signaling increases AEC2 differentiation into AEC1 involving PATS after injury, bleomycin-induced injury in Sftpc-CreER; R26-tdTomato mice was performed, followed by Nutlin-3a (TP53 activator) or dimethylsulfoxide (DMSO; control) administration starting on day 8 after injury and tissue collection on day 20 (FIG. 9A). Immunostaining for AGER revealed that Nultin-3a treatment led to significantly higher differentiation of Sftpc-tdt+ cells into AEC1s compared with DMSO treatment (FIG. 9B). There were no AGER+Sftpc-tdt+ cells in uninjured lungs that received Nutlin-3a, observed suggesting that Nutlin-3a-induced TP53 activation alone is not sufficient to induce differentiation of AEC2s into AEC1s (FIG. 9B). In addition, the effect of Nutlin-3a on the AEC2s in alveolar organoids was tested. The organoids were treated with Nutlin-3a or DMSO starting on day 7 until harvest on day 15 (FIG. 9C). The organoids treated with Nutlin-3a showed an increase in the number and intensity of AGER+ cells as well as a decrease in the number of Ki67+ proliferating cells compared with the controls (FIG. 9D). These data further support that ectopic activation of TP53 signaling enhances AEC2 differentiation in vivo and ex vivo.

Figure 9E:
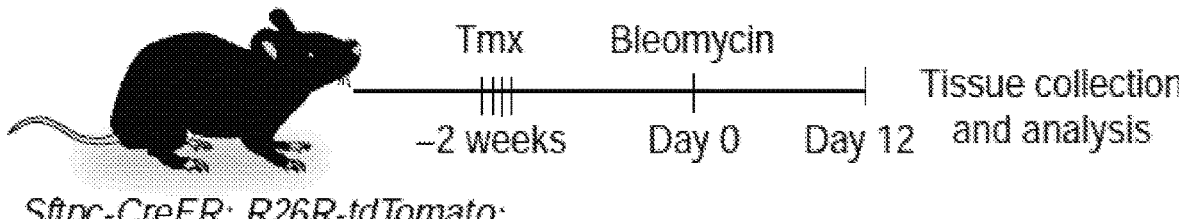
Figure 9F:
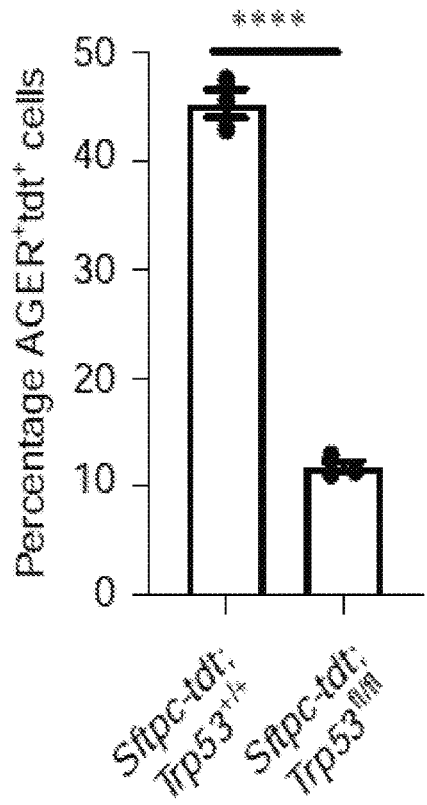
Figure 9G:
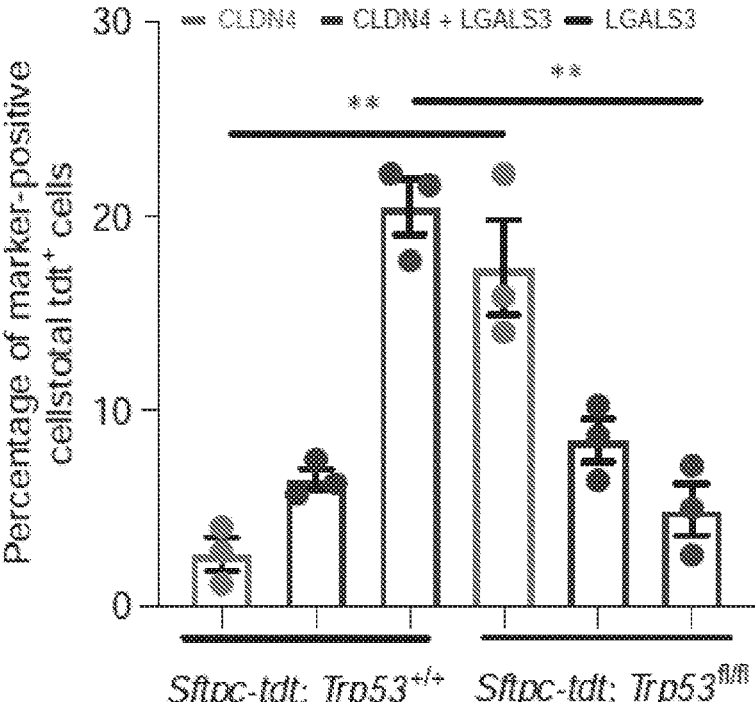
Figure 9H:
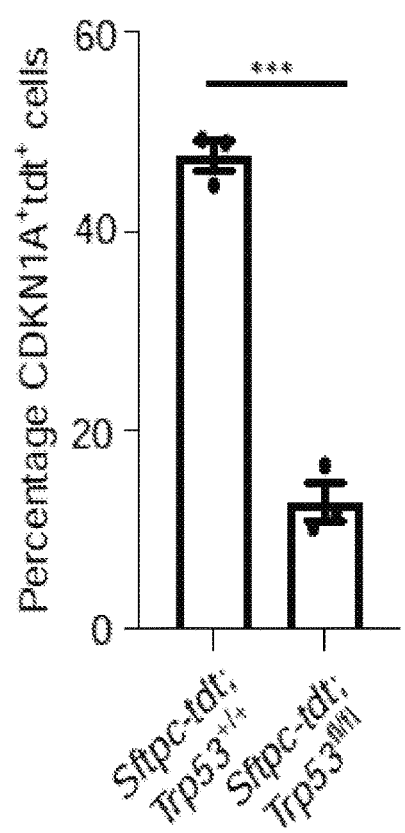

The data indicated that activation of TP53 signaling enhances AEC2 differentiation. To test whether TP53 is necessary for differentiation of AEC2s into AEC1s, the Sftpc-CreER; R 26-tdTomato; Trp53fl/fl mouse model was utilized, in which tamoxifen administration allows the deletion of TP53 and expression of tdTomato specifically in AEC2s. Bleomycin injury was performed, followed by tissue collection on day 12 (FIG. 9E). Sftpc-CreER; R26-tdTomato; Trp53+/+ mice were used as controls. Immunostaining revealed numerous stretched lineage-labeled cells co-expressing AGER in the bleomycin-treated control mice (FIG. 9F). In contrast, tdt+ cells in TP53-deficient lungs showed no AGER expression after bleomycin treatment and had an abnormal morphology (FIG. 9F). Note that the TP53-deficient AEC2s looked normal in the regions that did not have bleomycin-induced injury. Immunostaining and quantification revealed a significant increase in the number of CLDN4+Sftpc-tdt+ cells and fewer LGALS3+Sftpc-tdt+ cells in the lungs of TP53-mutant mice compared with controls following injury (FIG. 9G).

Expression analysis revealed a significant decrease in the levels of CDKN1A (a known target of TP53) in TP53fl/fl lungs compared with controls (FIG. 911). Immunostaining for cell-death marker revealed no difference between TP53 mutant and controls, indicating that the loss of TP53 did not affect cell death. Together, these data revealed that TP53 is essential for the differentiation of AEC2s into AEC1s, and TP53-deficient AEC2s are stuck in PATS and unable to progress to AEC1.

Figure 10A:
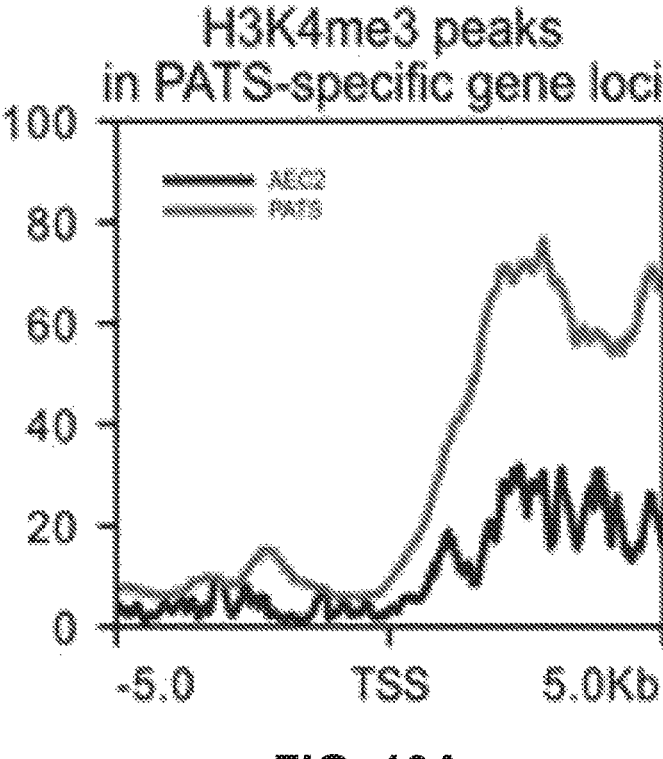
FIGS. 10A-10E shows transcriptional control of PATS by TP53 signaling.

Example 9: TP53 Binds to PATS-Associated Gene Loci and Controls their Expression To identify the transcription-factor modules that are potentially active in PATS cells, chromatin immunoprecipitation (ChIP) analysis was performed for the histones H3K4me3, H3K36me3 and H3K27ac to identify active promoters, transcribing genes and enhancers, respectively. PATS cells and AEC2s from bleomycin-treated Ctgf-GFP and control mice were isolated, respectively, and used for histone-marks analysis. H3K4me3 enrichment was found in genes corresponding to cell-type-specific promoters (Sftpc in AEC2 and Fn1 in PATS). Further analysis revealed enrichment of numerous H3K4me3 peaks overlapping with the transcriptional start sites and promoters of transcripts specific to PATS cells from bleomycin-damage-induced lungs compared with AEC2s from controls (FIG. 10A). Motif analysis of the H3K4me3 peaks predicted enrichment of binding sites for transcription factors, including TP53, ETS1, NF1, ATF3 and SOX4-all of which have been implicated in PATS-enriched pathways. Enrichment for H3K4me3, H3K27ac and H3K36me3 in known TP53 target gene loci (Fas and Mdm2) in PATS compared to AEC2s. Predicted binding sites were found for TP53 in the Mdm2 enhancer and Fas promoter, two well-known direct targets of TP53. Together, these data implicate a direct role for TP53 in the transcriptional control of PATS-specific genes.

Figure 10B:
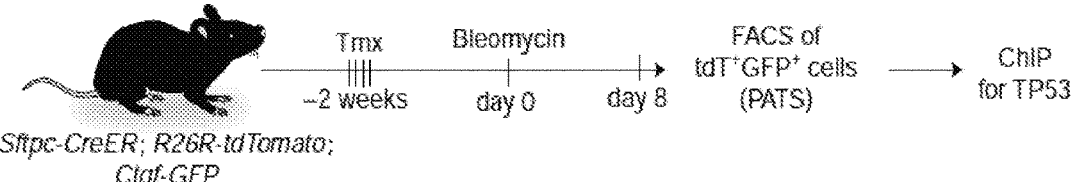
Figure 10C:
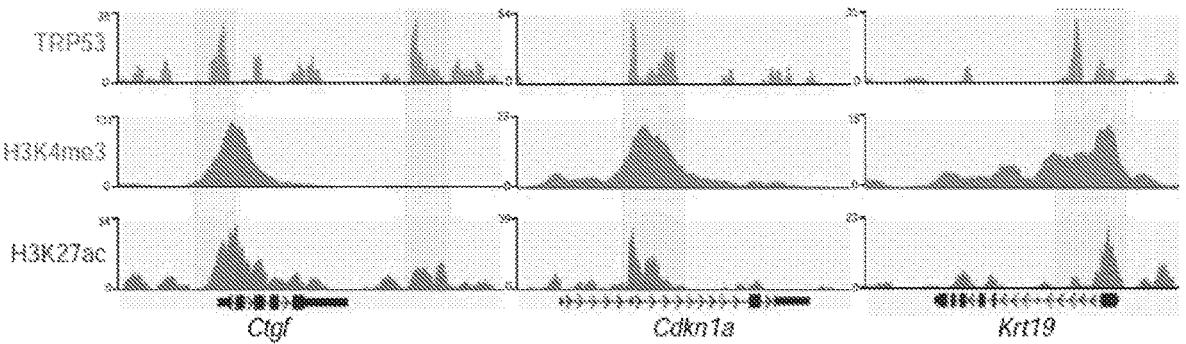
Figure 10D:
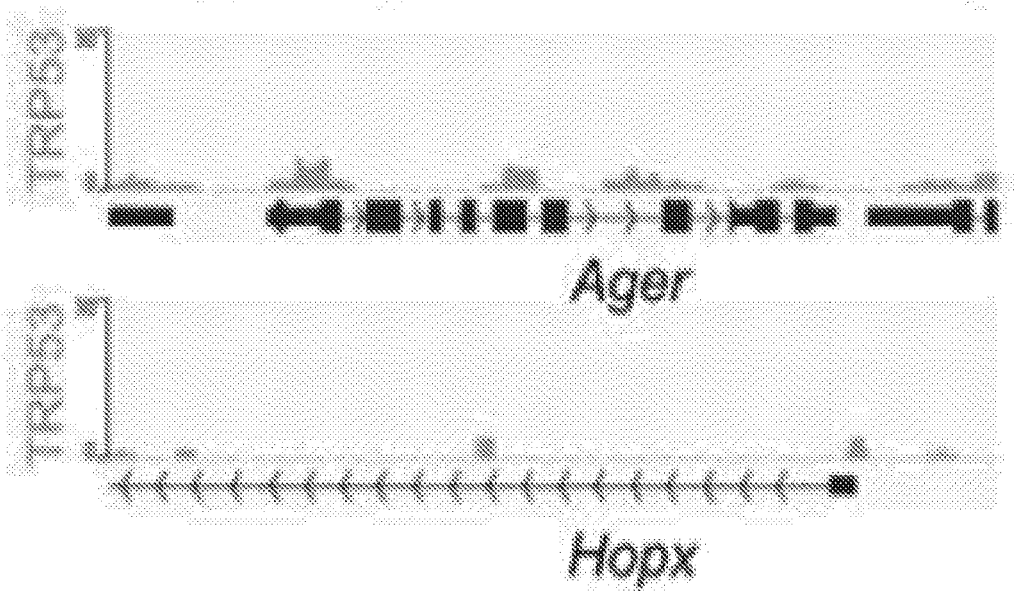
Figure 10E:
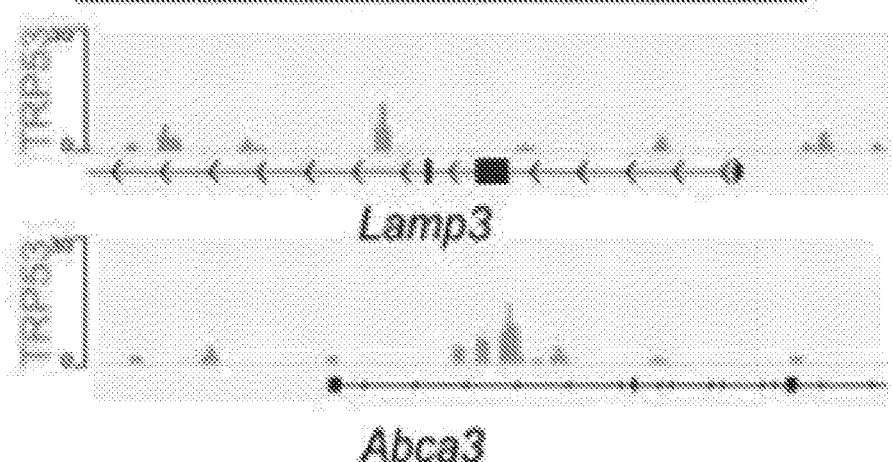

ChIP analysis was performed for TP53 in PATS cells to empirically test whether TP53 directly regulates transcriptional programs associated with PATS. Given that the scRNA-seq analysis revealed that TP53 signaling is highly enriched in the Ctgf+ subset of PATS, a Sftpc-CreER; R26R-tdTomato; Ctgf-GFP mouse model was generated to purify AEC2-lineage-derived PATS cells for ChIP analysis. PATS cells (tdt+GFP+) were purified from the lungs of Sftpc-CreER; R26R-tdTomato; Ctgf-GFP mice on day 8 post bleomycin administration and performed multiplexed indexed T7 ChIP (Mint-ChIP) analysis for TP53 (FIG. 10B). Data visualization on Integrative Genome Viewer (IGV) tracks revealed strong enrichment of TP53 on previously described targets including Mdm2, Trp53 and Basp1. More importantly, strong enrichment of TP53 was observed on many (22 of 28) PATS target genes that we analyzed including Fn1, Sfn, Actn1, Nupr1, Myl12a, Calm1, Ctgf, Cdkn1a and Krt19 (FIG. 10C). Note TP53 enrichment was not observed on AEC1 or AEC2 gene loci (FIG. 10D and FIG. 10E). In addition, overlap was also found between TP53-enrichment regions and H3K4me3 or H3K27ac marks, consistent with TP53 binding on the promoters and enhancers of the PATS-associated genes (FIG. 10C). Together, these data revealed that TP53 directly binds to PATS-enriched gene promoters and enhancers.

Figure 11J:
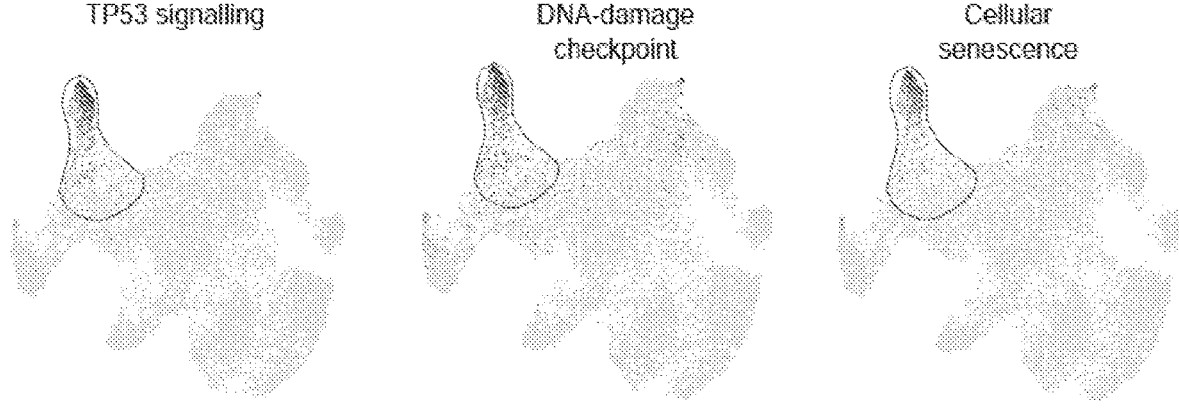
Figure 11K:
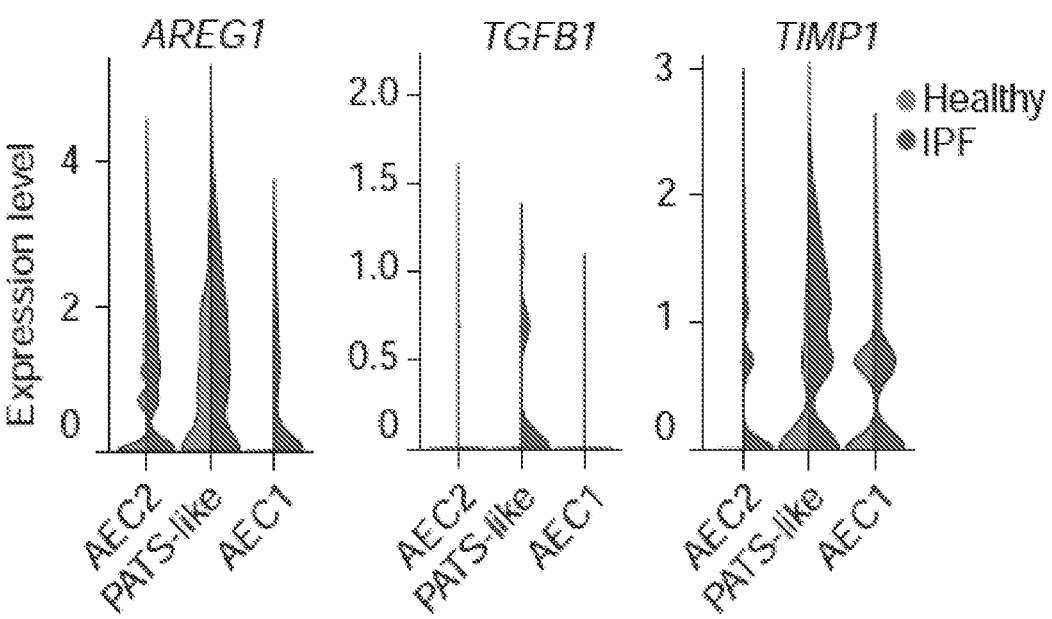
Figure 11L:
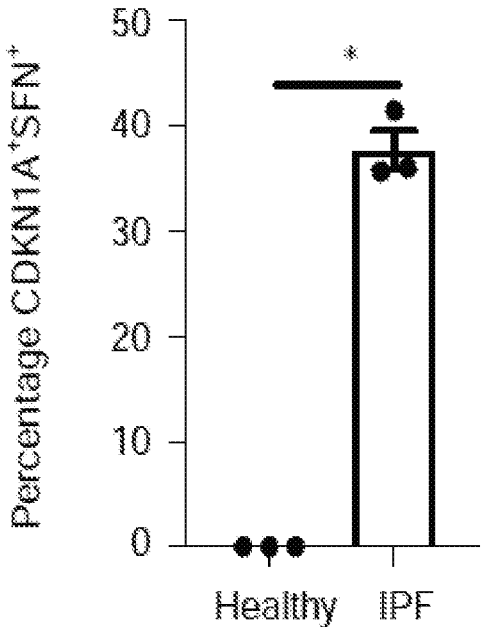
Figure 11M:
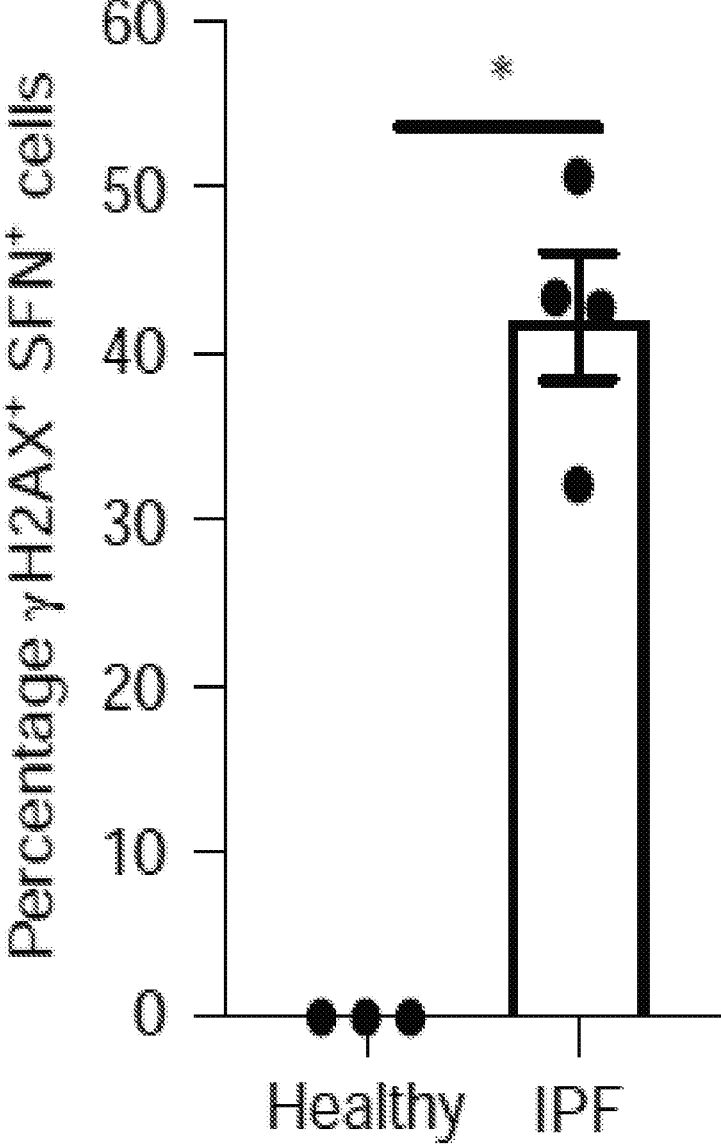

Example 10: PATS-Associated Gene-Expression Signatures and Signaling Pathways are Enriched in Human Fibrotic Lungs Recent studies suggested that the alveolar epithelial cells that line fibrotic foci in idiopathic pulmonary fibrosis (IPF) show features of senescence, growth arrest and differentiation blockade. To test whether alveolar progenitors stall their differentiation process in a PATS-like state in response to a non-permissive pathological microenvironment, a recently reported scRNA-seq dataset from the lungs of human patients with IPF29 was analyzed. First, all non-epithelial and airway cells were excluded from further analysis. Numerous AEC2s and AEC1s in both healthy and IPF lungs were observed, with apparent overlap in UMAP plots (FIG. 11A). In contrast, a distinct cell cluster that was highly enriched in IPF samples and did not overlap with either AEC1s or AEC2s was found (FIG. 11B). These cells were previously annotated by their marker gene expression as KRT5-KRT17+. Notably, analysis of differential gene expression revealed a striking resemblance of transcripts—including Sfn, Sox4 and Fn1, and also S100A2, PTGS2, KRT17, KRT8, CALS1, CLDN4, MMP7, PRSS2, IGFBP7, COLIA1, MDK, TAGLN, GDF15, TM4SF1, and CTSE—between the IPF-enriched cell cluster and PATS cells from the murine organoids and injury model. The human IPF-specific cluster was therefore named as 'PATS-like' cells (FIG. 11A and FIG. 11B). Other transcripts that were highly enriched in the PATS-like population are CALD1, PRSS2, MMP7 and S100A2. To validate the scRNA-seq data, immunofluorescence analysis was performed on healthy human and fibrotic and non-fibrotic regions of lungs with IPF (FIG. 11C). Co-immunofluorescence analysis of PATS-like cells (SFN, CLDN4 and KRT17), AEC2s (SFTPC and HTII-280), AEC1s (AGER) and myofibroblasts (ACTA2) revealed the expression of PATS-like markers specifically in the fibrotic regions of IPF lungs but not in the healthy controls and regions of IPF lungs with a healthy appearance (FIG. 11D, FIG. 11E, FIG. 11F, FIG. 11G, FIG. 11H, FIG. 11I). Interestingly, KRT17 has been recently shown to be expressed in basal cells of the normal lung and basaloid-like cells in IPF lungs (Habermann et al., 2019, doi.org/10.1101/753806; Adams et al., 2019, doi.org/10.1101/759902). A similar expression pattern of TP63, another marker for basal cells, specifically in the fibrotic, but not in non-fibrotic, regions of the IPF lungs was also found (FIG. 11H, FIG. 11I). It was found that PATS-like markers are highly enriched in regions of severe fibrosis (FIG. 11D-FIG. 11I), coinciding with high levels of COL1A1 and accumulation of myofibroblasts (FIG. 7D). Quantification of PATS markers (SFN, CLDN4, KRT17 and TP63) further supported these findings (FIG. 11E, FIG. 11G, and FIG. 11I). Moreover, it was observed that PATS cells acquired an elongated morphology in IPF lungs as opposed to the cuboidal AEC2s in healthy lungs (FIG. 11D, FIG. 11F, and FIG. 11G). Note that AGER expression was absent in regions in IPF lungs with many PATS-like cells (FIG. 11F). Gene ontology and pathway analysis revealed an enrichment for components of p53 signaling (CDKN1A, CDKN2A, and MDM2, as well as CCND1, CCND1, SNF, GADD45A, BID, BAX PMAIP1, BBC3, BCL2L1, PERP, ZMAT3, IGFBP3, CD82, thbs1, SERPINB5, RRM2B, SESN3, STEAP3, TP73), DNA-damage checkpoint (RPS27L and PLK3, as well as BRSK1, HMGA2, PEA15, PLK2, PRKDC, SOX4, TRIAP1) and cellular senescence (TGFβ2 and HIPK2, as well as CDKN2B, CXCL8, EIF4EBP1, ES1, NFATC1, SERPINE1, TGFB1, ZFP36L1); FIG. 11J). Moreover, the PATS-like cluster was enriched for components of focal adhesion, tight junction and regulation of the actin cytoskeleton, indicating a remarkable resemblance between PATS-like cells in IPF and those in organoids and regenerating alveoli. A significant enrichment for AREG, TGFB1, TGFβ2 and TIMP1—known regulators of fibrosis—were found in PATS-like cells (FIG. 11K). Next, markers of cell senescence (β-galactosidase activity and CDKN1A) and DNA-damage response (γH2AX) were analyzed in IPF and healthy lungs. The data revealed specific expression of these markers in the PATS-like population in IPF but not in healthy lungs (FIG. 11L and FIG. 11M). Together, the analysis revealed similarities between PATS cells from regenerating tissues and PATS-like cells that are specific to pathological fibrotic lungs.

Discussion

Figure 12:
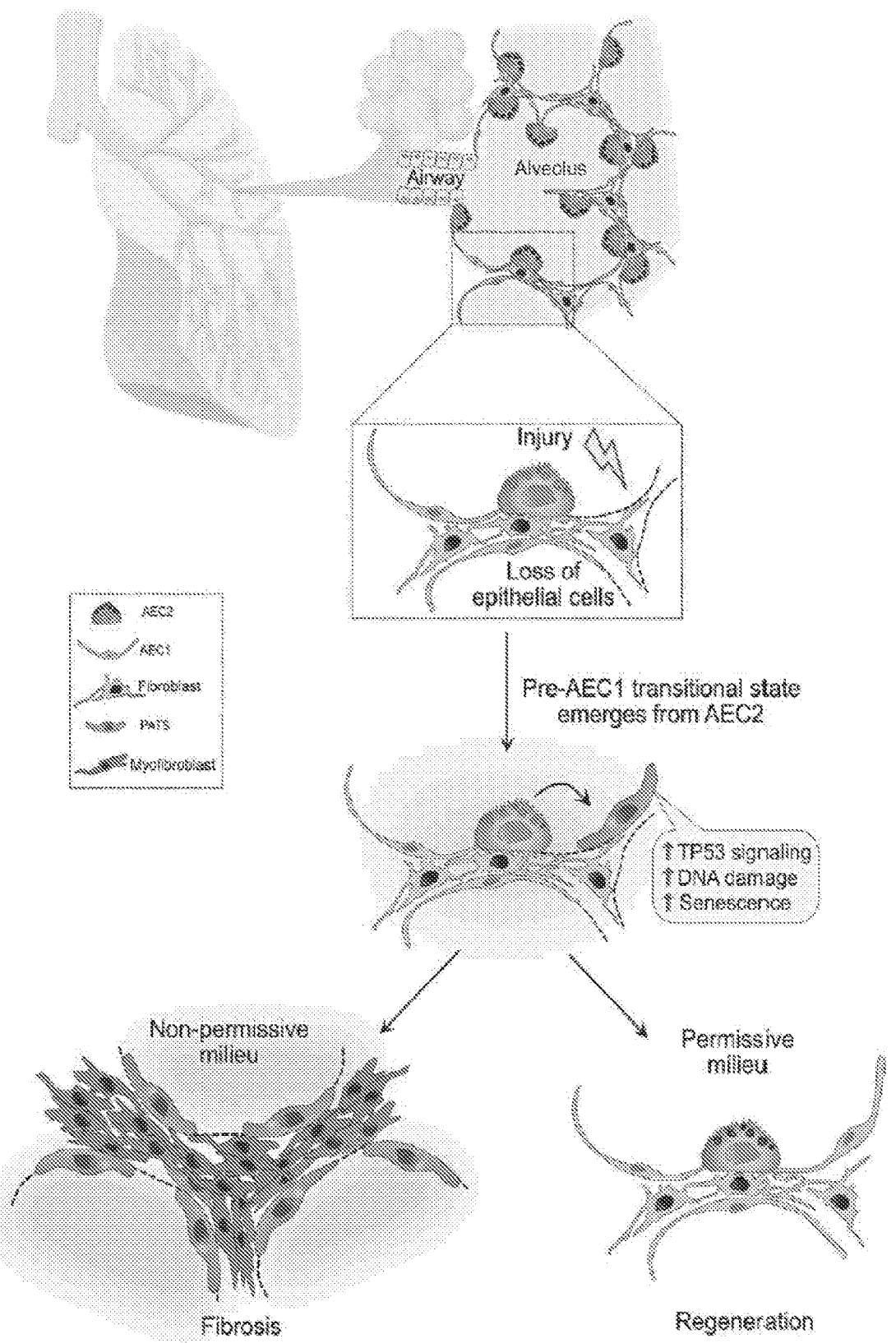
FIG. 12 is a schematic describing emergence of a novel transitional cell state in alveolar stem cell-mediated epithelial regeneration and its persistence in disease pathogenesis. Alveolar stem cells replicate in response to damage and generate a novel transitional cell state which normally matures into functional alveolar type-1 epithelial cells. The previously unappreciated transitional state is directly regulated by TP53 signaling, vulnerable to DNA damage and undergoes a transient senescent state. This state is enriched in human fibrotic lungs.

This study uncovered a previously unknown transitional state (PATS) that traverses between AEC2 and AEC1 and has a specific gene expression signature. Fate-mapping studies demonstrate a clear lineage relationship from AEC2 to PATS to AEC1. Therefore, with the addition of these transitional cell states, this work revises the hierarchy of alveolar epithelial cells. Specific gene-expression signatures indicate that PATS are not merely undergoing a gradual loss of AEC2 characteristics but represent a unique transitional population (FIG. 12). These cells are enriched for pathways—including TP53, NF-κB, YAP, TGFβ and HIF1 previously shown to be important for lung regeneration (La-Canna, et al., 2019, J. Clin. Invest. 129, 2107-2122; Riemondy et al., 2019, JCI Insight 5, e123637; Cheng et al., 2007, J. Immunol. 178, 6504-6513; McConnell et al., 2016, Cell Rep. 17, 2173-2182). Enrichment for transcripts associated with cell-cycle arrest, senescence and SOX4 were observed, a known regulator of epithelial-mesenchymal transition and cell adhesion in other tissues33. Through genetic and pharmacological modulation, these data demonstrate that TP53 signaling is necessary and sufficient to promote AEC2 differentiation into AEC1 involving PATS in regenerating tissues. Analysis by ChIP revealed a direct control of PATS genes by TP53. This study provides direct evidence for binding of TP53 to numerous cytoskeletal genes. Moreover, TP53 binding was observed on genes that are implicated in DNA-damage pathways (Nupr1 and Sox4).

The above analysis of human lungs has identified PATS-like cells that are specifically present in the fibrotic regions of IPF lungs. Similar to murine PATS cells, PATS-like cells in human lungs are characterized by enrichment for genes associated with cellular senescence, TP53 signaling and TGFβ-regulated genes all of which are known to be involved in fibrosis in multiple organs, including the lung (Zhang et al., 2015, Cell Death Dis. 6, e1847; Lipson et al., 2012, Fibrogenesis Tissue Repair 5, S24). In contrast, some differences were found in gene-expression signatures between murine and human IPF-specific PATS-like cells. These include TP63, KRT17 and COL1A1, which are found only in human PATS-like cells. The RNA-velocity projections from human scRNA-seq data suggest that these KRT17+TP63+ cells originate from AEC2s. Immunofluorescence for KRT17 and TP63 further suggested that these cells are surrounded by PATS-like cells within the same alveoli.

The findings showed that PATS cells undergo extensive stretching during AEC2 differentiation into thin and large AEC1s, which makes them vulnerable to DNA damage, a feature associated with most degenerative lung diseases-notably pulmonary fibrosis and cancers (Kropski et al., 2013, Dis. Models Mechanisms 6, 9-17; da Silva, et al., 2013, BMC Med. Genet. 14, 93). Previous studies revealed that cell stretching causes DNA damage when they migrate or squeeze through narrow spaces (McGregor et al., 2016, Curr. Opin. Cell Biol. 40, 32-40). The injury models and 2D culture indeed suggest that AEC2s undergo extensive stretching during differentiation into AEC1s. Therefore, the transitional cell state has clinical implications, notably in lung diseases associated with DNA damage (da Silva, et al., 2013, BMC Med. Genet. 14, 93; Sauler et al., 2018, Eur. Respir. J. 52, 1701994). Interestingly, the PATS population is enriched for SOX4 (known to regulate cytoskeletal genes), which is induced following DNA damage and is critical in TP53 stabilization and function. Together, these data support a model in which cells evolved co-transcriptional programs to combat DNA damage, which can occur when cells undergo stretching. In addition, genome-wide studies have identified mutations in DNA-damage-repair components—such as XRCC-family genes, LIG4, TERC, PARP and RTEL1—with emphysema and pulmonary fibrosis40. Thus, the newly identified transitional state implicates cell-shape changes and associated vulnerabilities accompanying alveolar stem cell differentiation in the lung pathogenesis.

Senescence is often seen as an age-associated pathological state in which cells acquire an abnormal and irreversible state. As described herein, it was found that alveolar stem cell differentiation involves a transitional state that exhibits cardinal features of senescence in normal tissue regeneration. Previous studies have indeed found senescent cells in developing limb bud tissues (Storer et al., 2013, Cell, 115, 1119-1130). Therefore, senescence may not necessarily occur exclusively in aged tissues but can be a reversible transient state accompanying tissue regeneration. This study thus redefines senescence as a state that can occur as part of normal tissue-maintenance programs and can be derailed in human diseases.

In conclusion, using alveolar organoid and in vivo injury-repair models, a pre-AEC1 transitional state in lung regeneration has been identified. This unique state is associated with cellular senescence and enrichment for defective alveolar regeneration pathways (FIG. 12). These results strongly suggest that prolonged senescence and stress-mediated pathways in transitional cell states can lead to diseases such as fibrosis.

Example 11: A Novel and Tunable Lung Injury Model Recapitulates Transient Fibrosis in Vivo Pulmonary fibrosis is a complex disease, involving alterations in the epithelial, mesenchymal, and immune populations, all in turn resulting in dramatic extracellular matrix changes and tissue remodeling. As a result of these complex interactions, the initiation of fibrosis is poorly understood, and has been assumed to be a result of a combination of all of these individual factors. Yet, it is still unknown whether damage to a single cell type can result in fibrotic initiation.

Figure 13A:
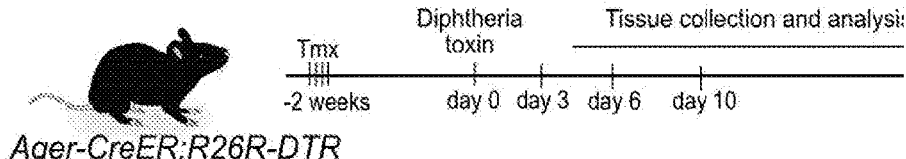
FIG. 13A is a schematic of AEC1 specific ablation model.
Figure 13B:
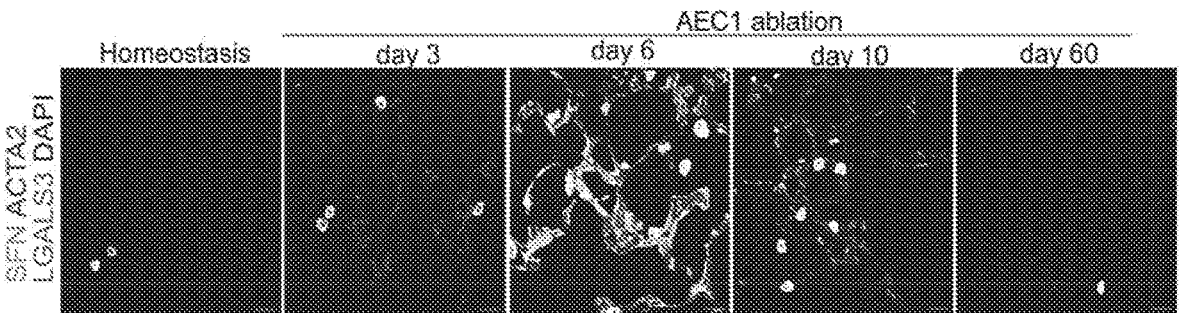
FIG. 13B are images showing immunostaining for SFN, ACTA2, LGALS3, and DAPI for cells that had undergone four rounds of AEC1 ablation and analyzed on day 3, day 6, day 10, and day 60.

To address this, cell type specific epithelial ablation models were developed (FIG. 13A), and it was found that ablation of a single cell type, AEC1s, results in rapid activation of alpha smooth muscle actin (aSMA or ACTA2, a marker of tissue fibrosis) in resident Pdgfra+ lipofibroblasts, while maintaining expression of Pdgfra and the stellate shape characteristic of lipofibroblasts. As these cells do not exhibit the morphological changes normally seen in myofibroblasts, they are termed "fibromyocytes" (FIG. 13B). Notably, following a single round of AEC1 ablation, fibromyocytes are transient, and as epithelial homeostasis is restored, ACTA2 expression gradually decreases. Moreover, specific ablation of AEC1 cells resulted in an intermediate PATS state, with rapid activation by day 3, and peaking at day 6. Intriguingly, PATS and fibromyocytes co-occurred, with PATS directly overlying the fibromyocyte-converted mesenchyme. PATS did not exist in significant numbers by day 10, suggesting that epithelial tissues resolve rapidly following this cell-type specific injury.

Figure 14A:
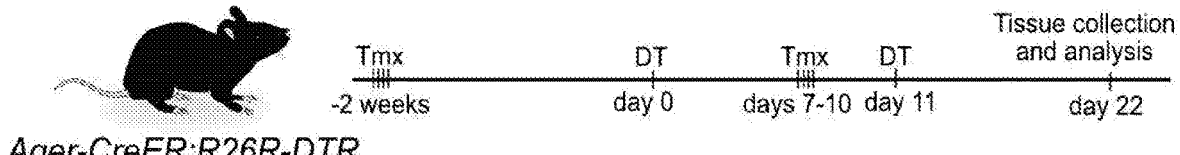
FIG. 14A is a schematic of repeated AEC1 ablation.
Figure 14B:
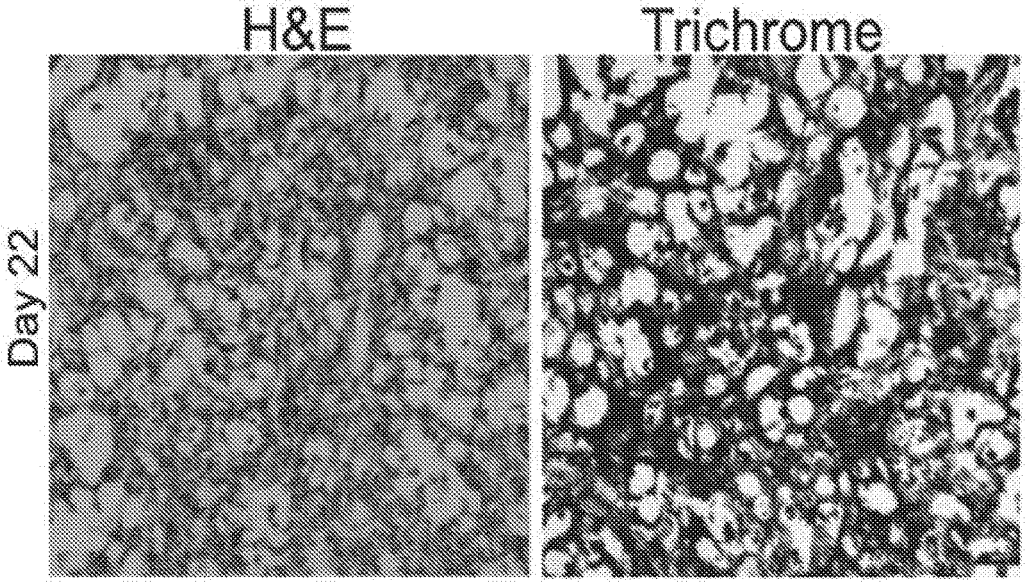
FIG. 14B are images showing H&E and trichome after 22 days.
Figure 14C:
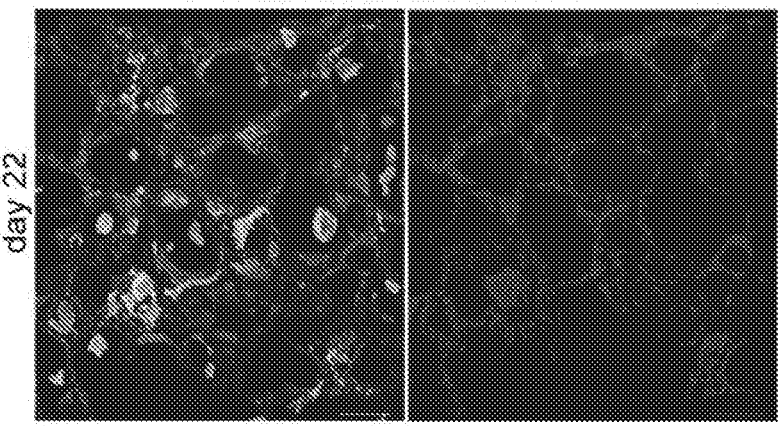
FIG. 14C are images showing immunostaining for LGALS3, ACTA2, and DAPI of ablated tissue after 22 days.
Figure 14D:
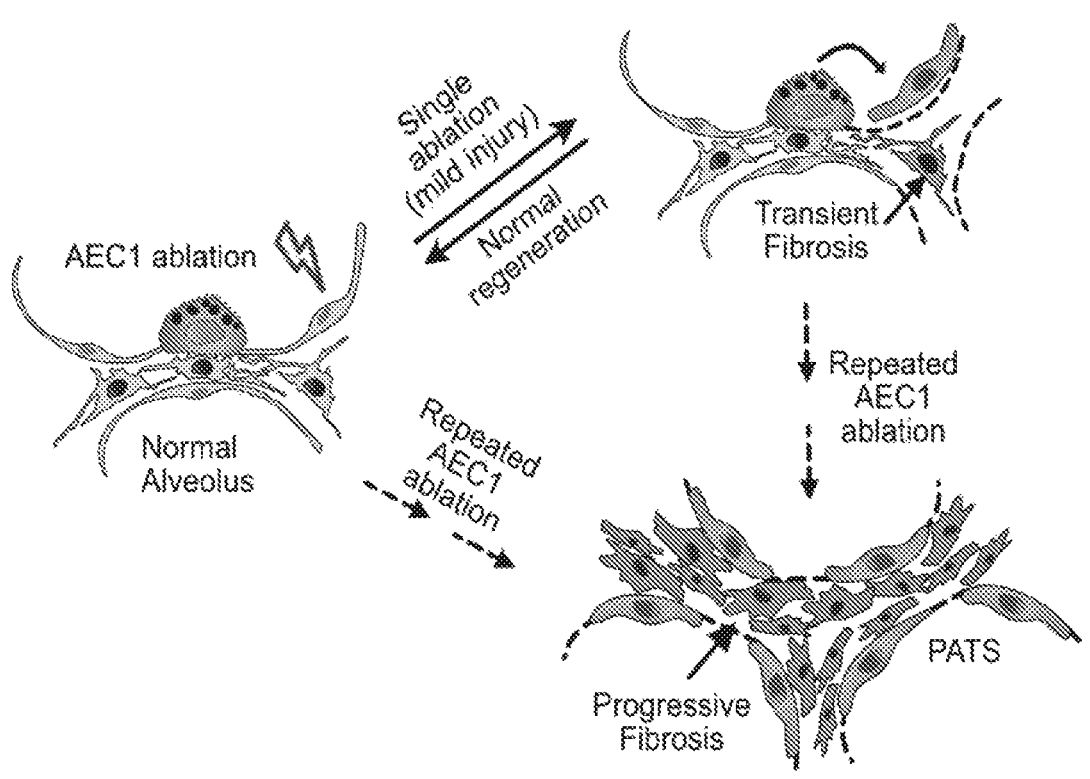
FIG. 14D is a schematic showing morphological changes with repeated AEC1 ablation.

Example 12: Persistence of PATS Drives Lipofibroblasts to Myofibroblasts In Vivo Considering that a single round of AEC1 ablation resulted in only transient, reversible fibrosis, fibromyocyte transition, and no myofibroblasts, it was thought that repeated AEC1 ablation (a surrogate for repeated alveolar injury) may further drive fibrosis (FIG. 14A). The preliminary histological analysis of mouse lungs after repeat AEC1 ablation indeed revealed increased ACTA2 expression in the alveoli, as well as morphological changes in ACTA2+ cells from a stellate to a "banded" morphology (FIG. 14B, FIG. 14C, and FIG. 14D). Additionally, repeated ablation enabled identification of fibrotic foci and Masson's trichrome analysis demonstrated an increase in ECM production in these lungs.

Figure 14E:
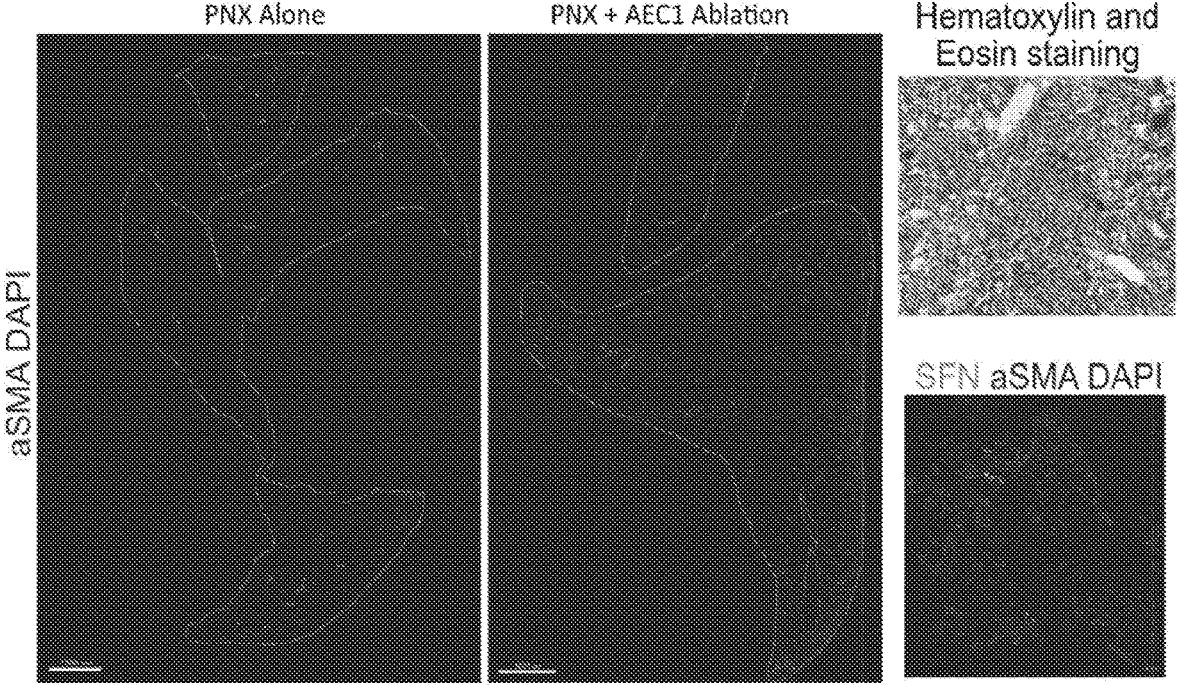
FIG. 14E are images showing widespread fibrosis in single ablation of AEC1 in combination with pneumonectomy induced injury.

While repeat ablation increases the amount of time PATS are present, as a result of a recurrent need for differentiation and therefore PATS accumulation, it was also hypothesized that a single, severely damaging injury would similarly result in increased PATS and fibrosis. To demonstrate this, two distinct injury models were combined, pneumonectomy and AEC1 ablation. Importantly, the two injuries were timed such that PATS would accumulate at the same time in these two injuries. Under these conditions, severe fibrosis and myofibrogenesis was extended from the periphery of the lung to throughout the lung, as indicated by aSMA staining (FIG. 14E). Notably, in this dual injury model, thick myofibroblast bands, fibrotic foci, as well as residual PATS presence was observed in these myofibroblast-dominated regions.

Example 13: A Scalable Co-Culture Model Recapitulates Lung Fibrosis Ex Vivo

Figure 15:
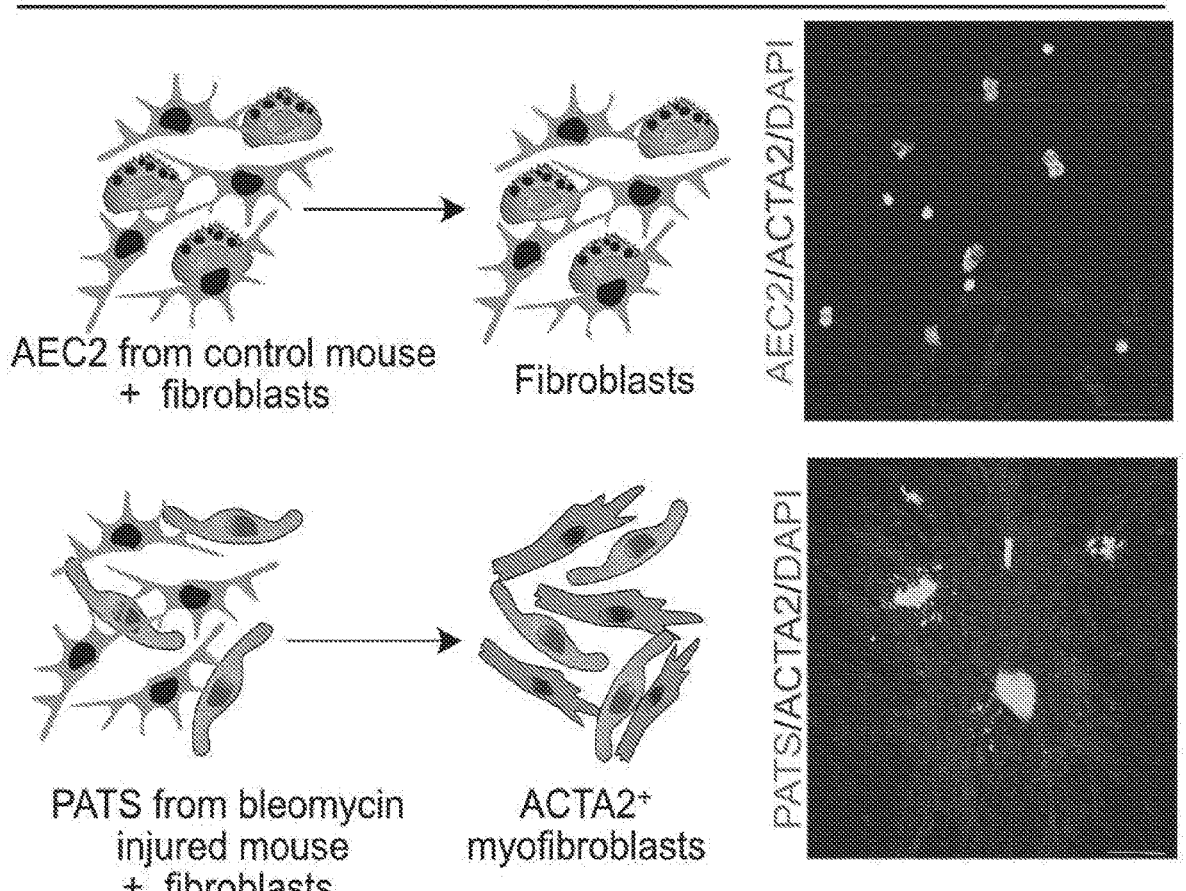
FIG. 15 is a schematic and coculture of PATS or AEC2s with lipofibroblasts. The data on the right demonstrates that coculture of PATS but not AEC2s induces the conversion of lipofibroblasts into myofibroblasts.

Collectively, the in vivo data suggested that PATS play a direct role in myofibroblast conversion. To definitively demonstrate this inter-cellular communication, culture conditions were established that would support the growth of both epithelial and lipofibroblasts and maintain their normal phenotype. Lipofibroblasts were then co-cultured with AEC2 cells (derived from SFTPC-GFP mice) or with PATS (isolated from CTGF-GFP mice (GFP$^+$/EpCAM$^+$) cells following bleomycin injury) for seven days and analyzed by immunostaining. Under these conditions, lipofibroblasts spontaneously expressed ACTA2 only in the presence of PATS but not with AEC2s. These data further suggest that PATS produce pro-fibrotic factors and induce the conversion of lipofibroblasts into myofibroblasts (FIG. 15).

Example 14: Lipofibroblast Identity is Maintained by Tonic, AEC1-Derived PDGFA Signaling However, while the data from these three injury models suggested that the presence of PATS drives further fibrogenesis, in single AEC1 ablation, it was observed that aSMA expression in native mesenchyme precedes PATS appearance. This suggested that loss of an AEC1 in isolation is sufficient to induce a lipofibroblast to myofibroblast transition, and it was hypothesized that AEC1s thus maintain lipofibroblast identity via intercellular communication.

Figure 16:
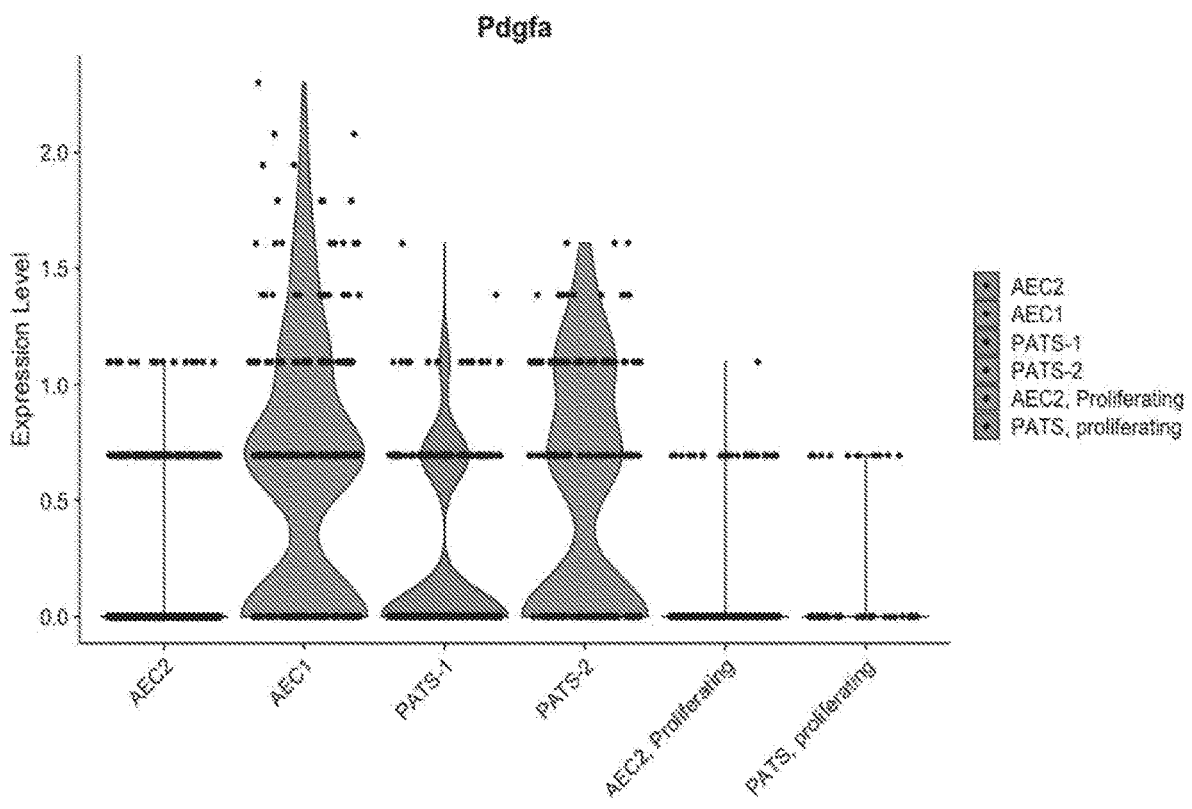
FIG. 16 is a violin plot showing that PDGFA is predominantly expressed in AEC1. In addition, PDGFA transcripts are also observed in the transition cells during AEC2s differentiation into AEC1.

To further probe the interactions between AEC1 and fibroblasts, epithelial-mesenchymal ligand-receptor expression data was examined from homeostatic single-cell data using Cellphone DB. Notably, of the two epithelial cells found in homeostasis, AEC1s, as compared to AEC2s, were predicted to have more numerous and stronger communication interactions with lipofibroblasts. Interestingly, it was found that AEC1s directly secrete the PDGFA ligand, for which the cognate receptor, PDGFRA, is expressed solely by lipofibroblasts in the lung mesenchyme. Importantly, PDGFA expression increases as cells transition from AEC2s, through the PATS state, and finally to AEC1s, suggesting that PDGFA is an important signal for epithelial-mesenchymal homeostatic maintenance (FIG. 16). Thus, it was hypothesized that PDGFA maintains lipofibroblast identity, and loss of AEC1 and resulting loss of PDGFA is a cue for lipo-to-myofibroblast initiation. As AEC2s differentiate into AEC1s, PDGFA expression is restored, and this subsequently returns fibromyocytes to their native lipofibroblast state.

Figure 17:
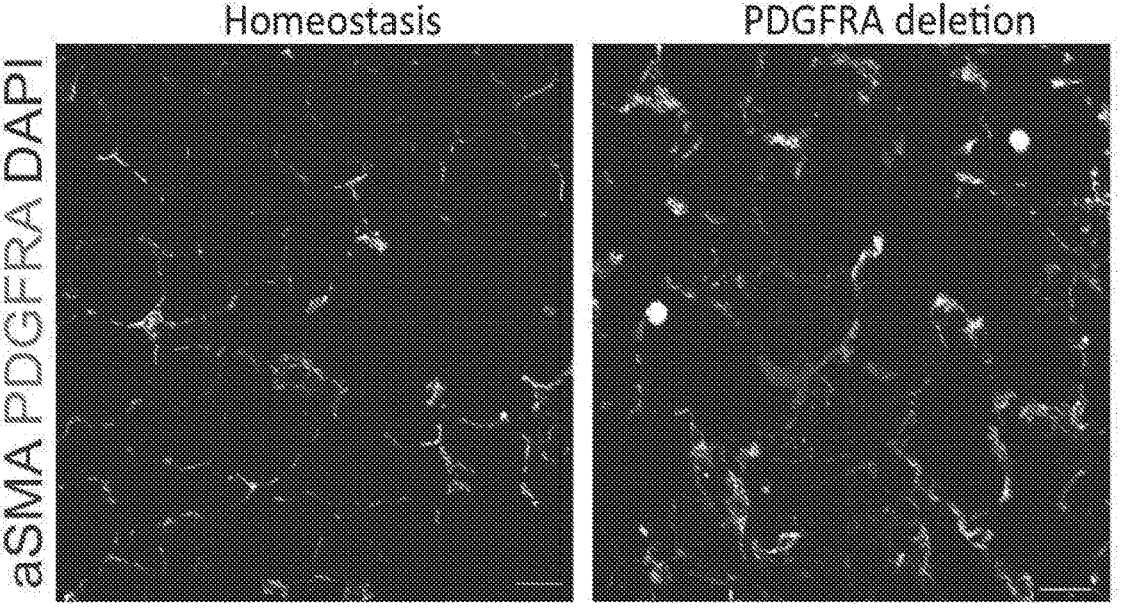
FIG. 17 are images showing immunostaining for aSMA, PDGFRA, and DAPI in control and PDGFRA-CreER/PDG-FRA^{flox} mice. These data demonstrate that loss of PDGFRA in fibroblasts is sufficient to induce their conversion into myofibroblasts.

Example 15: Disruption of PDGFA Signaling is Sufficient for Initiation of Myofibrogenesis To test whether loss of the PDGFA signaling axis is sufficient for myofibroblast conversion, a cell-type specific conditional knockout model of PDGFRA, PDGFRA-CreER/PDGFRA$^{flox}$ was generated. This mouse line only has a single functional allele of PDGFRA, and upon tamoxifen administration, results in complete loss of PDGFRA expression exclusively in PDGFRA+ cells. Notably, after just two days following PDGFRA deletion, these mice began to express aSMA in the lung mesenchyme, indicative of rapid myofibroblast conversion upon loss of the PDGFRA signaling axis (FIG. 17). Based on these data, it was hypothesized that PDGFA is necessary and sufficient for maintenance of lipofibroblasts.

Figure 18:
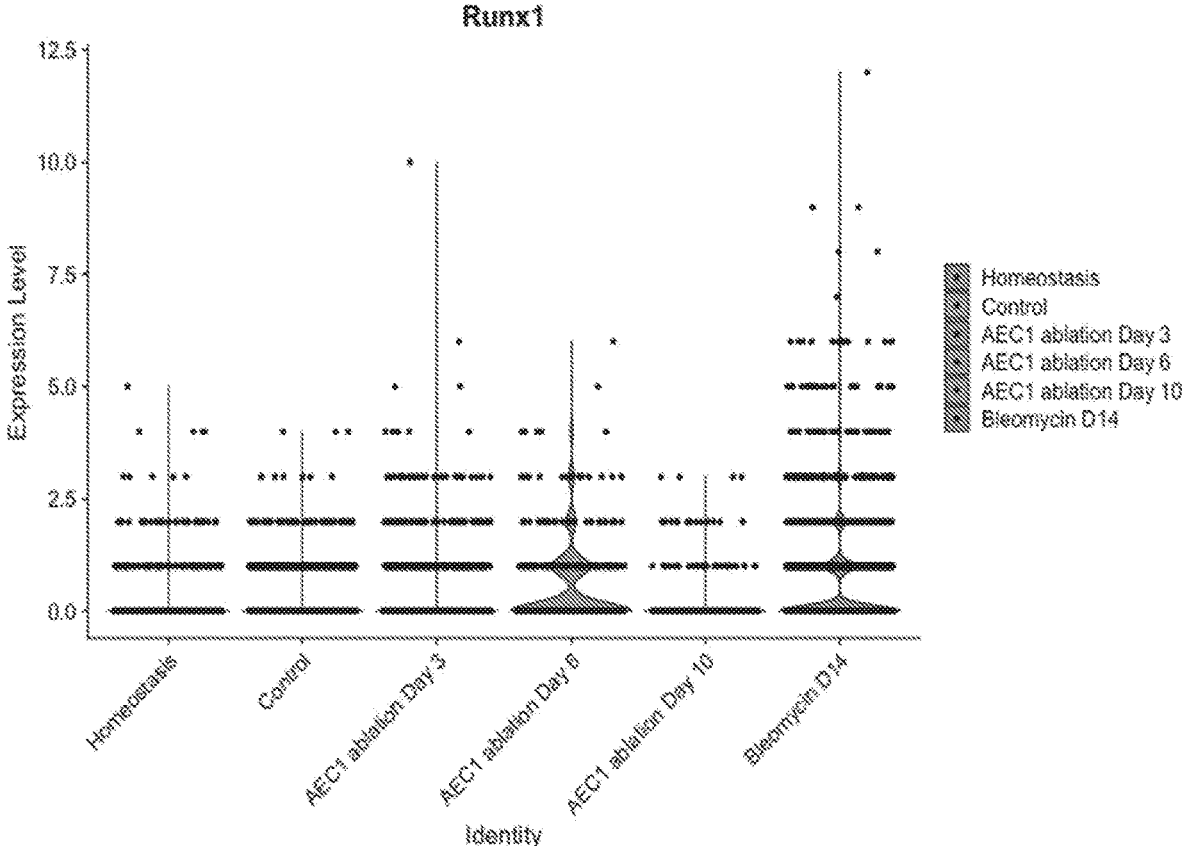
FIG. 18 is a violin plot showing that Runx1 is upregulated in fibroblasts post-AEC1 ablation and following bleomycin injury.
Figure 19:
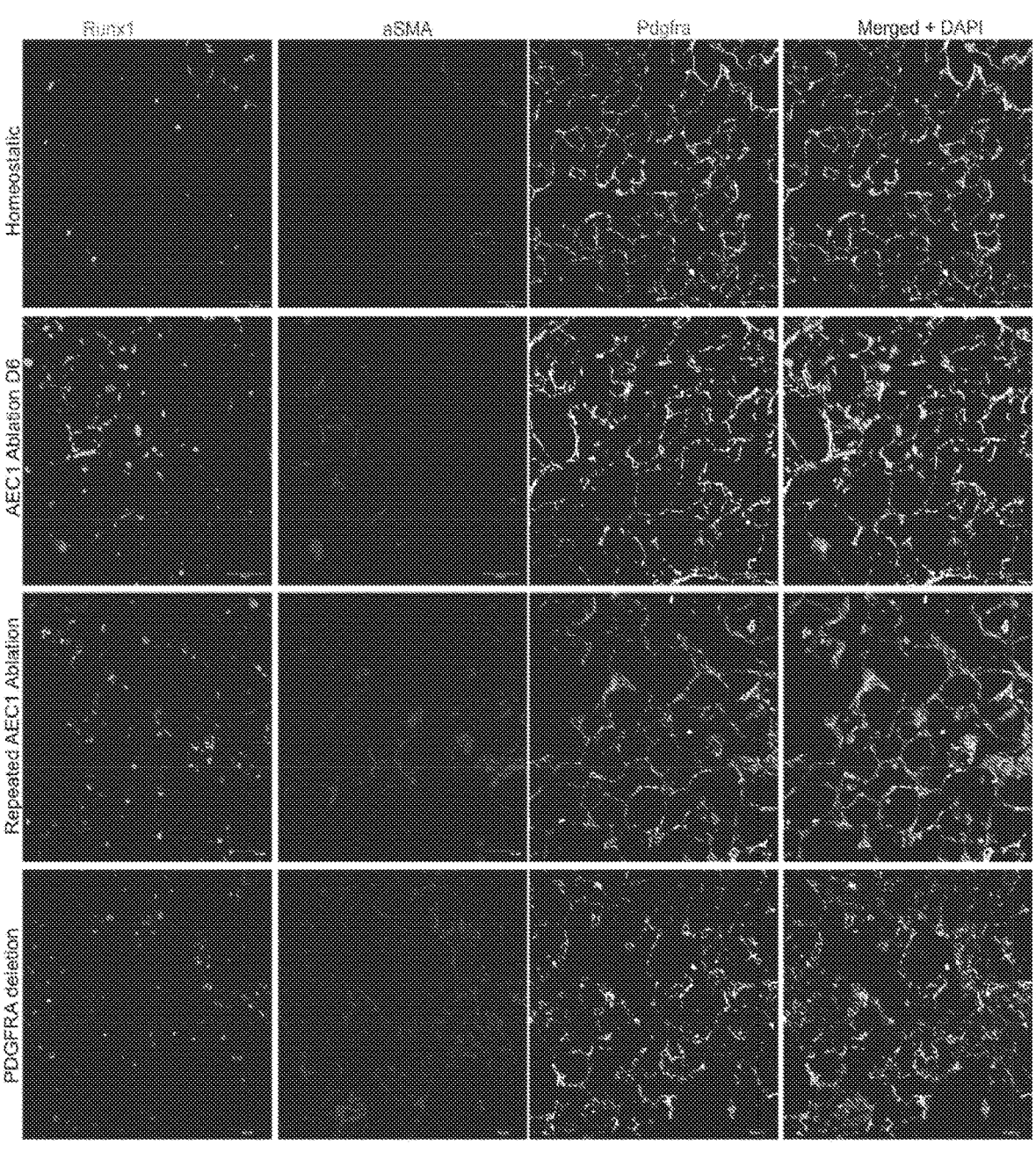
FIG. 19 are images showing immunostaining for Runx1, aSMA, Pdgfa, and DAPI on the AEC1 ablation model, repeated AEC1 ablation model, and PDGFRA deletion. These data demonstrate that RUNX1 expression is increased in single and repeat AEC1 ablation mouse models as well as in targeted loss of PDGFRA in fibroblasts.

Example 16: Runx1 is a Master Transcriptional Regulator of Myofibrogenic Fate In order to determine master regulators effecting lipofibroblast to myofibroblast transitions, transcription factors were interrogated that are preferentially upregulated in post-injury conditions. Runx1, a transcription factor known to be linked to fibrotic progression in multiple organs, was found to be strongly upregulated post-AEC1 ablation and following bleomycin injury (FIG. 18). Importantly, Runx1 expression increases across all models of fibrotic injury models described here, including AEC1 ablation, repeated AEC1 ablation, and PDGFRA deletion (FIG. 19).

Figure 20A:
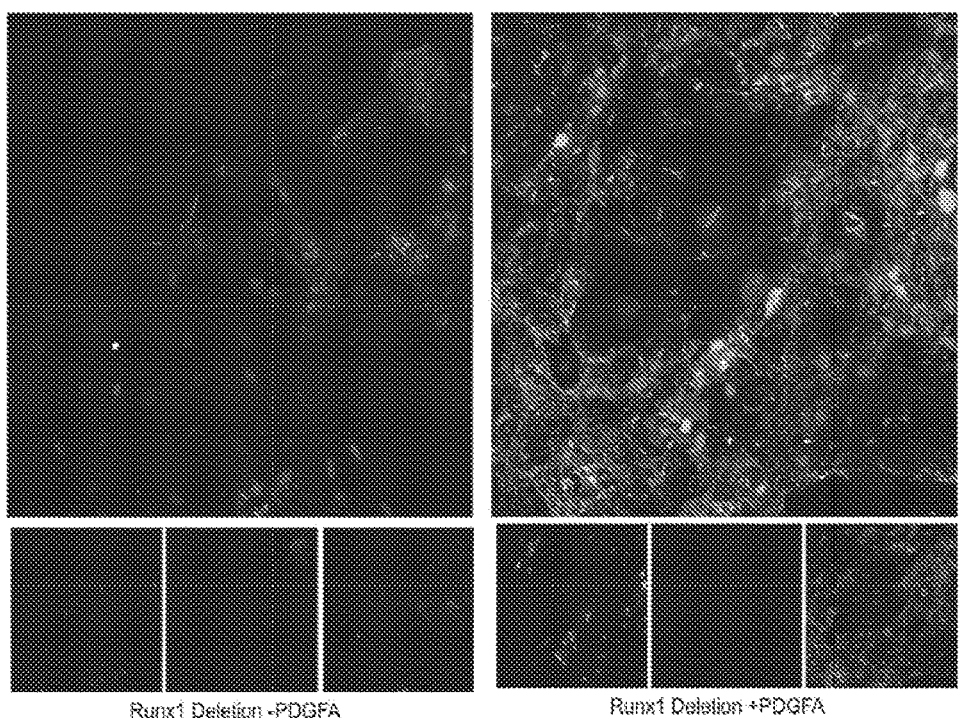
FIG. 20A are images showing immunostaining for GFP, aSMA, Pdgfa, and DAPI in RUNX1 deficient cells.
Figure 20B:
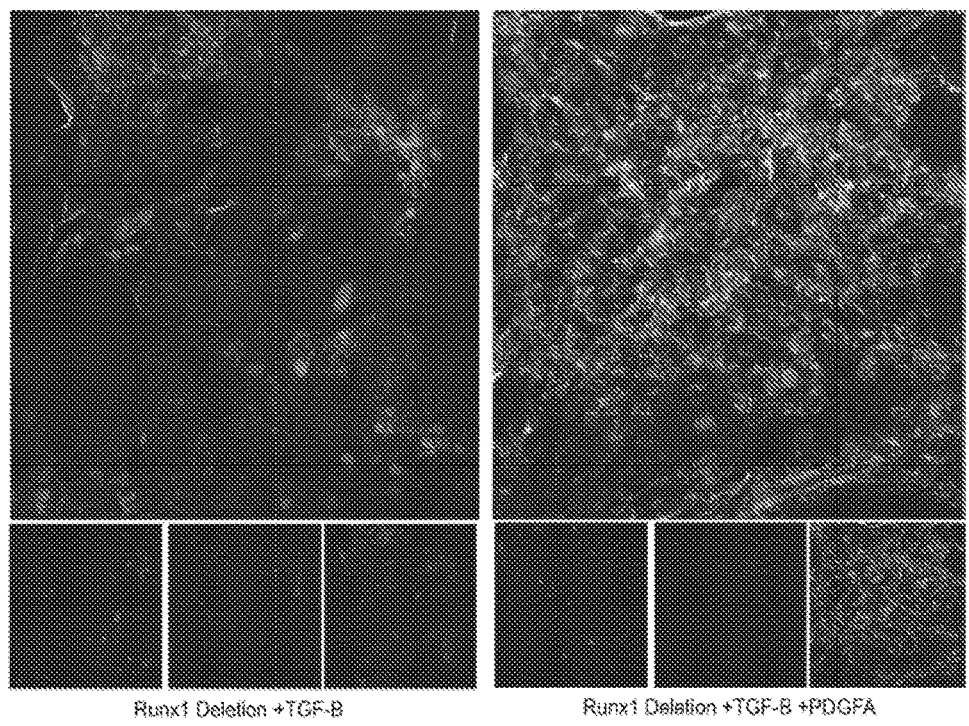
FIG. 20B are images showing immunostaining for GFP, aSMA, Pdgfa, and DAPI in RUNX1 deficient cells containing TGF-B. These data demonstrate that loss of RUNX1 blocks fibroblasts conversion into myofibroblasts.

Example 17: Genetic and Pharmacological Inhibition of RUNX1 Blocks TGFb Induced Fibrogenesis Using the culture system, the direct role of Runx1 in myofibrogenesis was determined. Wild-type lipofibroblasts treated with TGF-B in culture express aSMA and down-regulate PDGFRA. Lipofibroblasts from Runx1$^{flow/flox}$ mice were cultured and administered Adeno-Cre-GFP virus, resulting in efficient Runx1 deletion in culture (FIG. 20A). Following Runx1 deletion, myofibrogenesis was induced using TGF-B. However, unlike wild-type fibroblasts, Runx1 deleted fibroblasts did not express aSMA, and maintained PDGFRA expression, indicating that Runx1 is necessary for myofibrogenesis (FIG. 20B). In addition to genetic deletion, these experiments were repeated with Runx1 pharmacologic inhibition, with the drug Ro 5-3335. Lipofibroblasts were cultured in the presence of Ro 5-3335 and TGF-B for 48 hours. As with Runx1 deletion, Ro 5-3335 treated lipofibroblasts maintained PDGFRA expression and their stellate shape, with virtually no aSMA expression and myofibrotic conversion.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise.

The present disclosure shall control in the event there are any disparities between any definitions and/or description found in the cited references.

The invention claimed is:

1. A method for drug screening on a lung injury organoid model, the method comprising:
   providing in a culture medium a co-culture of cells comprising pre-alveolar type-1 transitional cell state (PATS) cells and alveolar fibroblasts; and
   screening a drug for a biological effect by
      contacting the culture medium with a drug; and
      measuring accumulation of PATS cells and/or expression of at least one marker of PATS cells.

2. The method of claim 1, wherein the PATS cells are isolated from diseased tissue.

3. The method of claim 2, wherein the diseased tissue is chronic obstructive pulmonary disease (COPD) lung tissue, pulmonary fibrosis lung tissue, idiopathic pulmonary fibrosis lung tissue, emphysema lung tissue, lung cancer tissue, Sarcoidosis lung tissue, interstitial pneumonia lung tissue, sepsis lung tissue, lung tissue having viral and bacterial infections, acute respiratory distress syndrome lung tissue, and bronchopulmonary dysplasia lung tissue.

4. The method of claim 1, wherein the PATS cells are generated by exposing lung epithelial cells to an injury-causing agent in vivo or in vitro.

5. The method of claim 4, wherein the injury-causing agent is bleomycin, diphtheria toxin (DT), tamoxifen, irradiation, a virus, a bacterium, or a fungus.

6. The method of claim 1, wherein the alveolar fibroblasts are lipofibroblasts.

7. The method of claim 1, wherein the culture medium comprises a platelet-derived growth factor receptor (PDGFR) ligand or an agent that is capable of maintaining platelet-derived growth factor receptor A (PDGFRA) expression.

8. The method of claim 7, wherein the PDGFR ligand is platelet-derived growth factor subunit A (PDGFA), platelet-derived growth factor subunit B (PDGFB), platelet-derived growth factor subunit C (PDGFC), and/or platelet-derived growth factor subunit D (PDGFD).

9. The method of claim 2, wherein the agent is Ro 5-3335, AI-10-49 or other molecules that regulate runt-related transcription factor (RUNX) or core binding factor (CBF) proteins.

10. The method of claim 1, wherein the at least one marker of PATS cells comprises CLDN4, KRT19, SFN, LGALS3, SOX4, S100A2, PTGS2, KRT17, KRT8, CALS1, MMP7, PRSS2, IGFBP7, COL1A1, MDK, TAGLN, GDF15, TM4SF1 TP63, and/or CTSE.

11. The method of claim 10, wherein the one or more markers is CLDN4, LGALS3, and LGALS3.

12. The method of claim 10, wherein the one or more markers is CLDN4, KRT19, and SFN, or wherein the one or more markers is CALD1, PRSS2, MMP7, and S100A2.

13. The method of claim 1, wherein the accumulation of PATS cells and/or the expression of at least one marker of PATS cells are measured relative to a control cell culture medium, wherein the control cell culture medium has not been contacted by the drug.

14. The method of claim 13, wherein an increase of the accumulation of PATS cells and/or an increase in the expression of at least one marker of PATS cells relative to a control cell culture medium indicates the presence or persistence of fibrosis.

15. The method of claim 13, wherein a decrease of the accumulation of PATS cells and/or a decrease in the expression of at least one marker of PATS cells indicates that the drug can treat fibrosis.

* * * * *